(12) United States Patent
Hamner et al.

(10) Patent No.: US 11,331,480 B2
(45) Date of Patent: May 17, 2022

(54) SYSTEMS, METHODS AND DEVICES FOR PERIPHERAL NEUROMODULATION FOR TREATING DISEASES RELATED TO OVERACTIVE BLADDER

(71) Applicant: Cala Health, Inc., Burlingame, CA (US)

(72) Inventors: Samuel Richard Hamner, San Francisco, CA (US); Serena HanYing Wong, Palo Alto, CA (US); Kathryn H. Rosenbluth, San Francisco, CA (US); Peter Lin, San Jose, CA (US); Shahid Mallick, Burlingame, CA (US); Erika Kristine Ross, San Mateo, CA (US)

(73) Assignee: Cala Health, Inc., San Mateo, CA (US)

( * ) Notice: Subject to any disclaimer, the term of this patent is extended or adjusted under 35 U.S.C. 154(b) by 110 days.

(21) Appl. No.: 16/500,377

(22) PCT Filed: Apr. 2, 2018

(86) PCT No.: PCT/US2018/025752
§ 371 (c)(1),
(2) Date: Oct. 2, 2019

(87) PCT Pub. No.: WO2018/187241
PCT Pub. Date: Oct. 11, 2018

(65) Prior Publication Data
US 2021/0101007 A1    Apr. 8, 2021

Related U.S. Application Data

(60) Provisional application No. 62/534,074, filed on Jul. 18, 2017, provisional application No. 62/481,006, filed on Apr. 3, 2017.

(51) Int. Cl.
*A61N 1/36* (2006.01)
*A61N 1/04* (2006.01)

(52) U.S. Cl.
CPC ....... *A61N 1/36007* (2013.01); *A61N 1/0456* (2013.01); *A61N 1/36034* (2017.08); *A61N 1/0484* (2013.01); *A61N 1/0492* (2013.01)

(58) Field of Classification Search
CPC ................. A61N 1/36007; A61N 1/36034
(Continued)

(56) References Cited

U.S. PATENT DOCUMENTS

| 3,204,637 A | 9/1965 | Frank et al. |
| 3,870,051 A | 3/1975 | Brindley |

(Continued)

FOREIGN PATENT DOCUMENTS

| DE | 102008042373 | 4/2010 |
| DE | 102009004011 | 7/2010 |

(Continued)

OTHER PUBLICATIONS

U.S. Appl. No. 16/071,056, filed Jul. 18, 2018, Wong et al.
(Continued)

*Primary Examiner* — Nadia A Mahmood
(74) *Attorney, Agent, or Firm* — Knobbe Martens Olson & Bear, LLP

(57) ABSTRACT

In some embodiments, systems and methods can include a wearable device with an electrically conductive skin interface that excites the underlying nerves from a transcutaneous surface stimulator. The device may be sized for a range of user sizes with stimulation electrodes positioned to target the appropriate nerves, such as the saphenous and/or tibial nerves. The stimulation could include burst stimulation, and involve receiving an input relating to autonomic nervous system activity of the patient, and modifying at least one
(Continued)

brain or spinal cord autonomic feedback loop relating to bladder function based on the input to balance parasympathetic and sympathetic nervous system activity of the patient.

19 Claims, 41 Drawing Sheets

(58) Field of Classification Search
USPC .................................................. 607/41
See application file for complete search history.

(56) References Cited

U.S. PATENT DOCUMENTS

| | | | |
|---|---|---|---|
| 4,300,575 A | 11/1981 | Wilson | |
| 4,458,696 A | 7/1984 | Larimore | |
| 4,461,075 A | 7/1984 | Bailey | |
| 4,539,996 A | 9/1985 | Engel | |
| 4,569,351 A | 2/1986 | Tang | |
| 4,582,049 A | 4/1986 | Ylvisaker | |
| 4,729,377 A | 3/1988 | Granek et al. | |
| 4,739,764 A | 4/1988 | Lue et al. | |
| 4,763,659 A | 8/1988 | Dunseath, Jr. | |
| 4,771,779 A | 9/1988 | Tanagho et al. | |
| 4,981,146 A | 1/1991 | Bertolucci | |
| 4,982,432 A | 1/1991 | Clark et al. | |
| 5,003,978 A | 4/1991 | Dunseath, Jr. | |
| 5,052,391 A | 10/1991 | Silverstone et al. | |
| 5,070,862 A | 12/1991 | Berlant | |
| 5,137,507 A | 8/1992 | Park | |
| 5,330,516 A | 7/1994 | Nathan | |
| 5,397,338 A | 3/1995 | Grey et al. | |
| 5,514,175 A | 5/1996 | Kim et al. | |
| 5,540,235 A | 7/1996 | Wilson | |
| 5,562,707 A | 10/1996 | Prochazka et al. | |
| 5,562,717 A | 10/1996 | Tippey et al. | |
| 5,573,011 A | 11/1996 | Felsing | |
| 5,575,294 A | 11/1996 | Perry et al. | |
| 5,606,968 A | 3/1997 | Mang | |
| 5,643,173 A | 7/1997 | Welles | |
| 5,775,331 A | 7/1998 | Raymond et al. | |
| 5,833,709 A | 11/1998 | Rise et al. | |
| 5,833,716 A | 11/1998 | Bar-Or et al. | |
| 5,899,922 A | 5/1999 | Loos | |
| 6,016,449 A | 1/2000 | Fischell et al. | |
| 6,081,744 A | 6/2000 | Loos | |
| 6,161,044 A | 12/2000 | Silverstone | |
| 6,178,352 B1 | 1/2001 | Gruzdowich et al. | |
| 6,351,674 B2 | 2/2002 | Silverstone | |
| 6,366,813 B1 | 4/2002 | DiLorenzo | |
| 6,445,955 B1 | 9/2002 | Michelson et al. | |
| 6,449,512 B1 | 9/2002 | Boveja | |
| 6,505,074 B2 | 1/2003 | Boveja et al. | |
| 6,546,290 B1 | 4/2003 | Shloznikov | |
| 6,564,103 B2 | 5/2003 | Fischer et al. | |
| 6,579,270 B2 | 6/2003 | Sussman et al. | |
| 6,652,449 B1 | 11/2003 | Gross et al. | |
| 6,704,603 B1 | 3/2004 | Gesotti | |
| 6,731,987 B1 | 5/2004 | McAdams et al. | |
| 6,735,474 B1 | 5/2004 | Loeb et al. | |
| 6,735,480 B2 | 5/2004 | Giuntoli et al. | |
| 6,788,976 B2 | 9/2004 | Gesotti | |
| 6,819,956 B2 | 11/2004 | DiLorenzo | |
| 6,829,510 B2 | 12/2004 | Nathan et al. | |
| 6,836,684 B1 | 12/2004 | Rijkhoff et al. | |
| 6,862,480 B2 | 3/2005 | Cohen et al. | |
| 6,892,098 B2 | 5/2005 | Ayal et al. | |
| 6,937,905 B2 | 8/2005 | Carroll et al. | |
| 6,959,215 B2 | 10/2005 | Gliner et al. | |
| 6,959,216 B2 | 10/2005 | Faghri | |
| 6,988,005 B2 | 1/2006 | McGraw et al. | |
| 7,010,352 B2 | 3/2006 | Hogan | |
| 7,089,061 B2 | 8/2006 | Grey | |
| 7,146,220 B2 | 12/2006 | Dar et al. | |
| 7,162,305 B2 | 1/2007 | Tong et al. | |
| 7,171,266 B2 | 1/2007 | Gruzdowich et al. | |
| 7,177,694 B2 | 2/2007 | Elbaum | |
| 7,177,703 B2 | 2/2007 | Boveja et al. | |
| 7,209,787 B2 | 4/2007 | DiLorenzo | |
| 7,228,178 B2 | 6/2007 | Carroll et al. | |
| 7,231,254 B2 | 6/2007 | DiLorenzo | |
| 7,236,830 B2 | 6/2007 | Gliner | |
| 7,254,444 B2 | 8/2007 | Moore et al. | |
| 7,277,758 B2 | 10/2007 | DiLorenzo | |
| 7,324,851 B1 | 1/2008 | DiLorenzo | |
| 7,326,235 B2 | 2/2008 | Edwards | |
| 7,328,068 B2 | 2/2008 | Spinelli et al. | |
| 7,349,739 B2 | 3/2008 | Harry et al. | |
| 7,353,064 B2 | 4/2008 | Gliner et al. | |
| 7,369,896 B2 | 5/2008 | Gesotti | |
| 7,499,747 B2 | 3/2009 | Kieval et al. | |
| 7,529,582 B1 | 5/2009 | DiLorenzo | |
| 7,558,610 B1 | 7/2009 | Odderson | |
| 7,636,602 B2 | 12/2009 | Baru Fassio et al. | |
| 7,643,880 B2 | 1/2010 | Tanagho et al. | |
| 7,643,882 B2 | 1/2010 | Boston | |
| 7,647,112 B2 | 1/2010 | Tracey et al. | |
| 7,650,190 B2 | 1/2010 | Zhou et al. | |
| 7,742,820 B2 | 6/2010 | Wyler et al. | |
| 7,761,166 B2 | 7/2010 | Giftakis et al. | |
| 7,769,464 B2 | 8/2010 | Gerber et al. | |
| 7,857,771 B2 | 12/2010 | Alwan et al. | |
| 7,899,556 B2 | 3/2011 | Nathan et al. | |
| 7,917,201 B2 | 3/2011 | Gozani et al. | |
| 7,930,034 B2 | 4/2011 | Gerber | |
| 7,949,403 B2 | 5/2011 | Palermo et al. | |
| 7,957,814 B2 | 6/2011 | Goetz et al. | |
| 7,974,696 B1 | 7/2011 | DiLorenzo | |
| 7,974,698 B2 | 7/2011 | Tass et al. | |
| 7,996,088 B2 | 8/2011 | Marrosu et al. | |
| 7,998,092 B2 | 8/2011 | Avni | |
| 8,000,796 B2 | 8/2011 | Tass | |
| 8,025,632 B2 | 9/2011 | Einarsson | |
| 8,046,083 B2 | 10/2011 | Tegenthoff et al. | |
| 8,075,499 B2 | 12/2011 | Nathan et al. | |
| 8,086,318 B2 | 12/2011 | Strother et al. | |
| 8,121,694 B2 | 2/2012 | Molnar et al. | |
| 8,145,316 B2 | 3/2012 | Deem et al. | |
| 8,165,668 B2 | 4/2012 | Dacey, Jr. et al. | |
| 8,175,718 B2 | 5/2012 | Wahlgren et al. | |
| 8,187,209 B1 | 5/2012 | Guiffrida et al. | |
| 8,219,188 B2 | 7/2012 | Craig | |
| 8,233,988 B2 | 7/2012 | Errico et al. | |
| 8,260,439 B2 | 9/2012 | Diubaldi et al. | |
| 8,301,215 B2 | 10/2012 | Lee | |
| 8,306,624 B2 | 11/2012 | Gerber et al. | |
| 8,313,443 B2 | 11/2012 | Tom | |
| 8,343,026 B2 | 1/2013 | Gardiner et al. | |
| 8,364,257 B2 | 1/2013 | Van Den Eerenbeemd et al. | |
| 8,374,701 B2 | 2/2013 | Hyde et al. | |
| 8,380,314 B2 | 2/2013 | Panken et al. | |
| 8,382,688 B2 | 2/2013 | Dar et al. | |
| 8,391,970 B2 | 3/2013 | Tracey et al. | |
| 8,396,556 B2 | 3/2013 | Libbus et al. | |
| 8,409,116 B2 | 4/2013 | Wang et al. | |
| 8,412,338 B2 | 4/2013 | Faltys | |
| 8,414,507 B2 | 4/2013 | Asada | |
| 8,428,719 B2 | 4/2013 | Napadow | |
| 8,435,166 B2 | 5/2013 | Burnett et al. | |
| 8,447,411 B2 | 5/2013 | Skelton et al. | |
| 8,452,410 B2 | 5/2013 | Emborg et al. | |
| 8,463,374 B2 | 6/2013 | Hudson et al. | |
| 8,473,064 B2 | 6/2013 | Castel et al. | |
| 8,548,594 B2 | 10/2013 | Thimineur et al. | |
| 8,571,687 B2 | 10/2013 | Libbus et al. | |
| 8,581,731 B2 | 11/2013 | Purks et al. | |
| 8,583,238 B1 | 11/2013 | Heldman et al. | |
| 8,588,884 B2 | 11/2013 | Hegde et al. | |
| 8,588,917 B2 | 11/2013 | Whitehurst et al. | |
| 8,608,671 B2 | 12/2013 | Kinoshita et al. | |
| 8,626,305 B2 | 1/2014 | Nielsen et al. | |
| 8,639,342 B2 | 1/2014 | Possover | |
| 8,644,904 B2 | 2/2014 | Chang et al. | |
| 8,644,938 B2 | 2/2014 | Craggs | |

(56) References Cited

U.S. PATENT DOCUMENTS

| | | |
|---|---|---|
| 8,660,656 B2 | 2/2014 | Moser et al. |
| 8,666,496 B2 | 3/2014 | Simon et al. |
| 8,679,038 B1 | 3/2014 | Giuffrida |
| 8,682,441 B2 | 3/2014 | De Ridder |
| 8,688,220 B2 | 4/2014 | Degiorgio et al. |
| 8,694,104 B2 | 4/2014 | Libbus et al. |
| 8,694,110 B2 | 4/2014 | Nathan et al. |
| 8,702,584 B2 | 4/2014 | Rigaux et al. |
| 8,702,629 B2 | 4/2014 | Giuffrida et al. |
| 8,706,241 B2 | 4/2014 | Firlik et al. |
| 8,718,780 B2 | 5/2014 | Lee |
| 8,740,825 B2 | 6/2014 | Ehrenreich et al. |
| 8,744,587 B2 | 6/2014 | Miesel et al. |
| 8,755,892 B2 | 6/2014 | Amurthur et al. |
| 8,768,452 B2 | 7/2014 | Gerber |
| 8,788,045 B2 | 7/2014 | Gross et al. |
| 8,788,049 B2 | 7/2014 | Lasko et al. |
| 8,792,977 B2 | 7/2014 | Kakei et al. |
| 8,798,698 B2 | 8/2014 | Kim et al. |
| 8,821,416 B2 | 9/2014 | Johansson et al. |
| 8,825,163 B2 | 9/2014 | Grill et al. |
| 8,825,165 B2 | 9/2014 | Possover |
| 8,843,201 B1 | 9/2014 | Heldman et al. |
| 8,845,494 B2 | 9/2014 | Whitall et al. |
| 8,845,557 B1 | 9/2014 | Giuffrida et al. |
| 8,855,775 B2 | 10/2014 | Leyde |
| 8,862,238 B2 | 10/2014 | Rahimi et al. |
| 8,862,247 B2 | 10/2014 | Schoendorf et al. |
| 8,868,177 B2 | 10/2014 | Simon et al. |
| 8,874,227 B2 | 10/2014 | Simon et al. |
| 8,880,175 B2 | 11/2014 | Simon |
| 8,886,321 B2 | 11/2014 | Rohrer et al. |
| 8,892,200 B2 | 11/2014 | Wagner et al. |
| 8,897,870 B2 | 11/2014 | De Ridder |
| 8,903,494 B2 | 12/2014 | Goldwasser et al. |
| 8,920,345 B2 | 12/2014 | Greenberg et al. |
| 8,923,970 B2 | 12/2014 | Bar-Yoseph et al. |
| 8,948,876 B2 | 2/2015 | Gozani et al. |
| 8,961,439 B2 | 2/2015 | Yang et al. |
| 8,972,017 B2 | 3/2015 | Dar et al. |
| 8,989,861 B2 | 3/2015 | Su et al. |
| 9,002,477 B2 | 4/2015 | Burnett |
| 9,005,102 B2 | 4/2015 | Burnett et al. |
| 9,008,781 B2 | 4/2015 | Ahmed |
| 9,011,310 B2 | 4/2015 | Ahmed |
| 9,017,273 B2 | 4/2015 | Burbank et al. |
| 9,026,216 B2 | 5/2015 | Rossi et al. |
| 9,042,988 B2 | 5/2015 | Dilorenzo |
| 9,060,747 B2 | 6/2015 | Salorio |
| 9,089,691 B2 | 7/2015 | Libbus et al. |
| 9,095,351 B2 | 8/2015 | Sachs et al. |
| 9,095,417 B2 | 8/2015 | Dar et al. |
| 9,107,614 B2 | 8/2015 | Halkias et al. |
| 9,119,964 B2 | 9/2015 | Marnfeldt |
| 9,155,885 B2 | 10/2015 | Wei et al. |
| 9,155,890 B2 | 10/2015 | Guntinas-Lichius et al. |
| 9,162,059 B1 | 10/2015 | Lindenthaler |
| 9,168,374 B2 | 10/2015 | Su |
| 9,174,045 B2 | 11/2015 | Simon et al. |
| 9,186,095 B2 | 11/2015 | Machado et al. |
| 9,192,763 B2 | 11/2015 | Gerber et al. |
| 9,220,895 B2 | 12/2015 | Siff et al. |
| 9,227,056 B1 | 1/2016 | Heldman et al. |
| 9,238,142 B2 | 1/2016 | Heldman et al. |
| 9,242,085 B2 | 1/2016 | Hershey et al. |
| 9,248,285 B2 | 2/2016 | Haessler |
| 9,248,286 B2 | 2/2016 | Simon et al. |
| 9,248,297 B2 | 2/2016 | Hoyer et al. |
| 9,254,382 B2 | 2/2016 | Ahmad et al. |
| 9,259,577 B2 | 2/2016 | Kaula et al. |
| 9,265,927 B2 | 2/2016 | Yonce et al. |
| 9,282,928 B1 | 3/2016 | Giffrida |
| 9,289,607 B2 | 3/2016 | Su et al. |
| 9,301,712 B2 | 4/2016 | McNames et al. |
| 9,302,046 B1 | 4/2016 | Giuffrida et al. |
| 9,314,190 B1 | 4/2016 | Giuffrida et al. |
| 9,314,622 B2 | 4/2016 | Embrey et al. |
| 9,332,918 B1 | 5/2016 | Buckley et al. |
| 9,339,641 B2 | 5/2016 | Rajguru et al. |
| 9,345,872 B2 | 5/2016 | Groteke |
| 9,364,657 B2 | 6/2016 | Kiani et al. |
| 9,364,672 B2 | 6/2016 | Marnfeldt |
| 9,375,570 B2 | 6/2016 | Kiani et al. |
| 9,408,683 B2 | 8/2016 | St. Anne et al. |
| 9,414,776 B2 | 8/2016 | Sillay et al. |
| 9,452,287 B2 | 9/2016 | Rosenbluth et al. |
| 9,468,753 B2 | 10/2016 | Fisher et al. |
| 9,474,898 B2 | 10/2016 | Gozani et al. |
| 9,549,872 B2 | 1/2017 | Chen et al. |
| 9,586,038 B1 | 3/2017 | Kosierkiewicz |
| 9,597,509 B2 | 3/2017 | Hoffer et al. |
| 9,675,800 B2 | 6/2017 | Li et al. |
| 9,782,584 B2 | 10/2017 | Cartledge et al. |
| 9,802,041 B2 | 10/2017 | Wong et al. |
| 9,861,283 B1 | 1/2018 | Giuffrida |
| 9,877,679 B1 | 1/2018 | Giuffrida |
| 9,877,680 B1 | 1/2018 | Giuffrida et al. |
| 9,924,899 B2 | 3/2018 | Pracar et al. |
| 9,974,478 B1 | 5/2018 | Brokaw et al. |
| 9,980,659 B2 | 5/2018 | Sadeghian-Motahar et al. |
| 10,004,900 B2 | 6/2018 | Kent et al. |
| 10,022,545 B1 | 7/2018 | Giuffrida |
| 10,028,695 B2 | 7/2018 | Machado et al. |
| 10,130,809 B2 | 11/2018 | Cartledge et al. |
| 10,173,060 B2 | 1/2019 | Wong et al. |
| 10,179,238 B2 | 1/2019 | Wong et al. |
| 10,213,602 B2 | 2/2019 | Ironi et al. |
| 10,549,093 B2 | 2/2020 | Wong et al. |
| 10,561,839 B2 | 2/2020 | Wong et al. |
| 10,603,482 B2 | 3/2020 | Hamner et al. |
| 10,625,074 B2 | 4/2020 | Rosenbluth et al. |
| 2002/0161415 A1 | 10/2002 | Cohen et al. |
| 2002/0165586 A1 | 11/2002 | Hill et al. |
| 2002/0177882 A1 | 11/2002 | DiLorenzo |
| 2003/0032992 A1 | 2/2003 | Thacker et al. |
| 2003/0045922 A1 | 3/2003 | Northrop |
| 2003/0088294 A1 | 5/2003 | Gesotti |
| 2003/0093098 A1 | 5/2003 | Heitzmann et al. |
| 2003/0149457 A1 | 8/2003 | Tcheng et al. |
| 2003/0181959 A1 | 9/2003 | Dobak, III |
| 2003/0187483 A1 | 10/2003 | Grey et al. |
| 2003/0195583 A1 | 10/2003 | Gruzdowich et al. |
| 2004/0015094 A1 | 1/2004 | Manabe et al. |
| 2004/0088025 A1 | 5/2004 | Gessotti |
| 2004/0093093 A1 | 5/2004 | Andrews |
| 2004/0127939 A1 | 7/2004 | Grey et al. |
| 2004/0133249 A1 | 7/2004 | Gesotti |
| 2004/0167588 A1 | 8/2004 | Bertolucci |
| 2004/0249416 A1 | 12/2004 | Yun et al. |
| 2004/0267331 A1 | 12/2004 | Koeneman et al. |
| 2005/0021103 A1 | 1/2005 | DiLorenzo |
| 2005/0055063 A1 | 3/2005 | Loeb et al. |
| 2005/0065553 A1 | 3/2005 | Ben Ezra et al. |
| 2005/0075502 A1 | 4/2005 | Shafer |
| 2005/0171577 A1 | 8/2005 | Cohen et al. |
| 2005/0234309 A1 | 10/2005 | Klapper |
| 2006/0047326 A1 | 3/2006 | Wheeler |
| 2006/0052726 A1 | 3/2006 | Weisz et al. |
| 2006/0095088 A1 | 5/2006 | De Ridder |
| 2006/0161218 A1 | 7/2006 | Danilov |
| 2006/0173509 A1 | 8/2006 | Lee et al. |
| 2006/0184059 A1 | 8/2006 | Jadidi |
| 2006/0217781 A1 | 9/2006 | John |
| 2006/0224191 A1 | 10/2006 | DiLorenzo |
| 2006/0229678 A1 | 10/2006 | Lee |
| 2006/0253167 A1 | 11/2006 | Kurtz et al. |
| 2006/0276853 A1 | 12/2006 | Tass |
| 2006/0293723 A1 | 12/2006 | Whitehurst et al. |
| 2007/0027486 A1 | 2/2007 | Armstrong |
| 2007/0073361 A1 | 3/2007 | Goren et al. |
| 2007/0123951 A1 | 5/2007 | Boston |
| 2007/0123952 A1 | 5/2007 | Strother et al. |
| 2007/0142862 A1 | 6/2007 | DiLorenzo |
| 2007/0156179 A1 | 7/2007 | Karashurov |

(56) References Cited

U.S. PATENT DOCUMENTS

| | | |
|---|---|---|
| 2007/0156182 A1 | 7/2007 | Castel et al. |
| 2007/0156183 A1 | 7/2007 | Rhodes |
| 2007/0156200 A1 | 7/2007 | Kornet et al. |
| 2007/0173899 A1 | 7/2007 | Levin et al. |
| 2007/0173903 A1 | 7/2007 | Goren et al. |
| 2007/0203533 A1 | 8/2007 | Goren et al. |
| 2007/0207193 A1 | 9/2007 | Zasler et al. |
| 2007/0282228 A1 | 12/2007 | Einav et al. |
| 2008/0004672 A1 | 1/2008 | Dalal et al. |
| 2008/0009772 A1 | 1/2008 | Tyler et al. |
| 2008/0021505 A1 | 1/2008 | Hastings et al. |
| 2008/0027507 A1 | 1/2008 | Bijelic et al. |
| 2008/0033259 A1 | 2/2008 | Manto et al. |
| 2008/0033504 A1 | 2/2008 | Bertolucci |
| 2008/0051839 A1 | 2/2008 | Libbus et al. |
| 2008/0058773 A1 | 3/2008 | John |
| 2008/0058893 A1 | 3/2008 | Noujokat |
| 2008/0147146 A1 | 6/2008 | Wahlgren et al. |
| 2008/0177398 A1 | 7/2008 | Gross et al. |
| 2008/0195007 A1 | 8/2008 | Podrazhansky et al. |
| 2008/0208288 A1 | 8/2008 | Podrazhansky et al. |
| 2008/0216593 A1 | 9/2008 | Jacobsen et al. |
| 2008/0288016 A1 | 11/2008 | Amurthur et al. |
| 2008/0312520 A1 | 12/2008 | Rowlandson et al. |
| 2009/0018609 A1 | 1/2009 | DiLorenzo |
| 2009/0076565 A1 | 3/2009 | Surwit |
| 2009/0105785 A1 | 4/2009 | Wei et al. |
| 2009/0112133 A1 | 4/2009 | Deisseroth et al. |
| 2009/0157138 A1 | 6/2009 | Errico et al. |
| 2009/0187121 A1 | 7/2009 | Evans |
| 2009/0216294 A1 | 8/2009 | Ewing et al. |
| 2009/0247910 A1 | 10/2009 | Klapper |
| 2009/0299435 A1 | 12/2009 | Gliner et al. |
| 2009/0318986 A1 | 12/2009 | Alo et al. |
| 2009/0326595 A1 | 12/2009 | Brockway et al. |
| 2009/0326607 A1 | 12/2009 | Castel et al. |
| 2010/0010381 A1 | 1/2010 | Skelton et al. |
| 2010/0010572 A1 | 1/2010 | Skelton et al. |
| 2010/0057154 A1 | 3/2010 | Dietrich et al. |
| 2010/0099963 A1 | 4/2010 | Kilger |
| 2010/0107657 A1 | 5/2010 | Vistakula |
| 2010/0125220 A1 | 5/2010 | Seong |
| 2010/0152817 A1 | 6/2010 | Gillbe |
| 2010/0174342 A1 | 7/2010 | Boston et al. |
| 2010/0222630 A1 | 9/2010 | Mangrum et al. |
| 2010/0227330 A1 | 9/2010 | Fink et al. |
| 2010/0249637 A1 | 9/2010 | Walter et al. |
| 2010/0292527 A1 | 11/2010 | Schneider et al. |
| 2010/0298905 A1 | 11/2010 | Simon |
| 2010/0324611 A1 | 12/2010 | Deming et al. |
| 2011/0009920 A1 | 1/2011 | Whitehurst et al. |
| 2011/0021899 A1 | 1/2011 | Arps et al. |
| 2011/0040204 A1 | 2/2011 | Ivorra et al. |
| 2011/0054358 A1 | 3/2011 | Kim et al. |
| 2011/0071590 A1 | 3/2011 | Mounaim et al. |
| 2011/0098780 A1 | 4/2011 | Graupe et al. |
| 2011/0118805 A1 | 5/2011 | Wei et al. |
| 2011/0125212 A1 | 5/2011 | Tyler |
| 2011/0137375 A1 | 6/2011 | McBride |
| 2011/0184489 A1 | 7/2011 | Nicolelis et al. |
| 2011/0202107 A1 | 8/2011 | Sunagawa et al. |
| 2011/0213278 A1 | 9/2011 | Horak et al. |
| 2011/0224571 A1 | 9/2011 | Pascual-Leone et al. |
| 2011/0230701 A1 | 9/2011 | Simon et al. |
| 2011/0245734 A1 | 10/2011 | Wagner et al. |
| 2011/0250297 A1 | 10/2011 | Oronsky et al. |
| 2011/0282412 A1 | 11/2011 | Glukhovsky et al. |
| 2011/0301663 A1 | 12/2011 | Wang et al. |
| 2012/0010492 A1 | 1/2012 | Thramann et al. |
| 2012/0053491 A1 | 3/2012 | Nathan et al. |
| 2012/0078319 A1 | 3/2012 | De Ridder |
| 2012/0088986 A1 | 4/2012 | David et al. |
| 2012/0092178 A1 | 4/2012 | Callsen et al. |
| 2012/0109013 A1 | 5/2012 | Everett et al. |
| 2012/0136410 A1 | 5/2012 | Rezai et al. |
| 2012/0158094 A1 | 6/2012 | Kramer et al. |
| 2012/0184801 A1 | 7/2012 | Simon et al. |
| 2012/0185020 A1 | 7/2012 | Simon et al. |
| 2012/0220812 A1 | 8/2012 | Mishelevich |
| 2012/0239112 A1 | 9/2012 | Muraoka |
| 2012/0259255 A1 | 10/2012 | Tomlinson et al. |
| 2012/0277621 A1 | 11/2012 | Gerber et al. |
| 2012/0302821 A1 | 11/2012 | Burnett |
| 2012/0310298 A1 | 12/2012 | Besio et al. |
| 2012/0310303 A1 | 12/2012 | Popovic et al. |
| 2012/0330182 A1 | 12/2012 | Alberts et al. |
| 2013/0006322 A1 | 1/2013 | Tai |
| 2013/0060124 A1 | 3/2013 | Zietsma |
| 2013/0066388 A1 | 3/2013 | Bernhard et al. |
| 2013/0066395 A1 | 3/2013 | Simon et al. |
| 2013/0085317 A1 | 4/2013 | Feinstein |
| 2013/0090519 A1 | 4/2013 | Tass |
| 2013/0116606 A1 | 5/2013 | Cordo |
| 2013/0123568 A1 | 5/2013 | Hamilton et al. |
| 2013/0123666 A1 | 5/2013 | Giuffrida et al. |
| 2013/0131484 A1 | 5/2013 | Pernu |
| 2013/0158624 A1 | 6/2013 | Bain et al. |
| 2013/0158627 A1 | 6/2013 | Gozani et al. |
| 2013/0231713 A1 | 9/2013 | De Ridder et al. |
| 2013/0236867 A1 | 9/2013 | Avni et al. |
| 2013/0238049 A1 | 9/2013 | Simon et al. |
| 2013/0245486 A1 | 9/2013 | Simon et al. |
| 2013/0245713 A1 | 9/2013 | Tass |
| 2013/0253299 A1 | 9/2013 | Weber et al. |
| 2013/0267759 A1 | 10/2013 | Jin |
| 2013/0281890 A1 | 10/2013 | Mishelevich |
| 2013/0289647 A1 | 10/2013 | Bhadra et al. |
| 2013/0296967 A1 | 11/2013 | Skaribas et al. |
| 2013/0297022 A1 | 11/2013 | Pathak |
| 2013/0331907 A1 | 12/2013 | Sumners et al. |
| 2013/0333094 A1 | 12/2013 | Rogers et al. |
| 2013/0338726 A1 | 12/2013 | Machado |
| 2014/0025059 A1 | 1/2014 | Kerr |
| 2014/0031605 A1 | 1/2014 | Schneider |
| 2014/0039573 A1 | 2/2014 | Jindra |
| 2014/0039575 A1 | 2/2014 | Bradley |
| 2014/0046423 A1 | 2/2014 | Rajguru et al. |
| 2014/0058189 A1 | 2/2014 | Stubbeman |
| 2014/0067003 A1 | 3/2014 | Vase et al. |
| 2014/0078694 A1 | 3/2014 | Wissmar |
| 2014/0081345 A1 | 3/2014 | Hershey |
| 2014/0094675 A1 | 4/2014 | Luna et al. |
| 2014/0094873 A1 | 4/2014 | Emborg et al. |
| 2014/0128939 A1 | 5/2014 | Embrey et al. |
| 2014/0132410 A1 | 5/2014 | Chang |
| 2014/0142654 A1 | 5/2014 | Simon et al. |
| 2014/0148873 A1 | 5/2014 | Kirn |
| 2014/0163444 A1 | 6/2014 | Ingvarsson |
| 2014/0171834 A1 | 6/2014 | DeGoede et al. |
| 2014/0214119 A1 | 7/2014 | Greiner et al. |
| 2014/0228927 A1 | 8/2014 | Ahmad et al. |
| 2014/0236258 A1 | 8/2014 | Carroll et al. |
| 2014/0249452 A1 | 9/2014 | Marsh et al. |
| 2014/0257047 A1 | 9/2014 | Sillay et al. |
| 2014/0257129 A1 | 9/2014 | Choi et al. |
| 2014/0276194 A1 | 9/2014 | Osorio |
| 2014/0277220 A1 | 9/2014 | Brennan et al. |
| 2014/0296752 A1 | 10/2014 | Edgerton et al. |
| 2014/0296934 A1 | 10/2014 | Gozani et al. |
| 2014/0296935 A1 | 10/2014 | Ferree et al. |
| 2014/0300490 A1 | 10/2014 | Kotz et al. |
| 2014/0309709 A1 | 10/2014 | Gozanl et al. |
| 2014/0316484 A1 | 10/2014 | Edgerton et al. |
| 2014/0324118 A1 | 10/2014 | Simon et al. |
| 2014/0330068 A1 | 11/2014 | Partsch et al. |
| 2014/0330335 A1 | 11/2014 | Errico et al. |
| 2014/0336003 A1 | 11/2014 | Franz et al. |
| 2014/0336722 A1 | 11/2014 | Rocon De Lima et al. |
| 2014/0343462 A1 | 11/2014 | Burnet |
| 2014/0350436 A1 | 11/2014 | Nathan et al. |
| 2014/0358040 A1 | 12/2014 | Kim et al. |
| 2014/0364678 A1 | 12/2014 | Harry et al. |
| 2015/0004656 A1 | 1/2015 | Tang et al. |

(56) References Cited

U.S. PATENT DOCUMENTS

| | | |
|---|---|---|
| 2015/0005852 A1* | 1/2015 | Hershey ............ A61N 1/36021 607/72 |
| 2015/0012067 A1 | 1/2015 | Bradley et al. |
| 2015/0038886 A1 | 2/2015 | Snow |
| 2015/0044656 A1 | 2/2015 | Eichhorn et al. |
| 2015/0057506 A1 | 2/2015 | Luna et al. |
| 2015/0073310 A1 | 3/2015 | Pracar et al. |
| 2015/0080979 A1 | 3/2015 | Lasko et al. |
| 2015/0100004 A1 | 4/2015 | Goldman et al. |
| 2015/0100104 A1 | 4/2015 | Kiani et al. |
| 2015/0100105 A1 | 4/2015 | Kiani et al. |
| 2015/0148866 A1 | 5/2015 | Bulsen et al. |
| 2015/0148878 A1* | 5/2015 | Yoo .................. A61N 1/0456 607/118 |
| 2015/0157274 A1 | 6/2015 | Ghassemzadeh et al. |
| 2015/0164377 A1 | 6/2015 | Nathan et al. |
| 2015/0164401 A1 | 6/2015 | Toth et al. |
| 2015/0190085 A1 | 7/2015 | Nathan et al. |
| 2015/0190634 A1 | 7/2015 | Rezai et al. |
| 2015/0202444 A1 | 7/2015 | Franke et al. |
| 2015/0208955 A1 | 7/2015 | Smith |
| 2015/0216475 A1 | 8/2015 | Luna et al. |
| 2015/0230733 A1 | 8/2015 | Heo et al. |
| 2015/0230756 A1 | 8/2015 | Luna et al. |
| 2015/0277559 A1 | 10/2015 | Vescovi et al. |
| 2015/0321000 A1 | 11/2015 | Rosenbluth et al. |
| 2015/0335882 A1 | 11/2015 | Gross |
| 2016/0001096 A1 | 1/2016 | Mishelevich |
| 2016/0008620 A1 | 1/2016 | Stubbeman |
| 2016/0016014 A1 | 1/2016 | Wagner et al. |
| 2016/0022987 A1 | 1/2016 | Zschaeck et al. |
| 2016/0022989 A1 | 1/2016 | Pfeifer |
| 2016/0038059 A1 | 2/2016 | Asada et al. |
| 2016/0045140 A1 | 2/2016 | Kitamura et al. |
| 2016/0089045 A1 | 3/2016 | Sadeghian-Motahar et al. |
| 2016/0106344 A1 | 4/2016 | Nazari |
| 2016/0121110 A1 | 5/2016 | Kent et al. |
| 2016/0128621 A1 | 5/2016 | Machado et al. |
| 2016/0129248 A1 | 5/2016 | Creasey et al. |
| 2016/0158542 A1 | 6/2016 | Ahmed |
| 2016/0158565 A1 | 6/2016 | Lee |
| 2016/0198998 A1 | 7/2016 | Rahimi et al. |
| 2016/0220836 A1 | 8/2016 | Parks |
| 2016/0262685 A1 | 9/2016 | Wagner et al. |
| 2016/0287879 A1 | 10/2016 | Denison et al. |
| 2016/0039239 A1 | 11/2016 | Yoo et al. |
| 2016/0339239 A1 | 11/2016 | Yoe et al. |
| 2017/0014625 A1 | 1/2017 | Rosenbluth et al. |
| 2017/0027812 A1 | 2/2017 | Hyde et al. |
| 2017/0056238 A1 | 3/2017 | Yi et al. |
| 2017/0079597 A1 | 3/2017 | Horne |
| 2017/0080207 A1 | 3/2017 | Perez et al. |
| 2017/0266443 A1 | 9/2017 | Rajguru et al. |
| 2017/0274208 A1 | 9/2017 | Nagel et al. |
| 2017/0287146 A1 | 10/2017 | Pathak et al. |
| 2017/0312505 A1 | 11/2017 | Ahmed |
| 2018/0049676 A1 | 2/2018 | Griffiths et al. |
| 2018/0064344 A1 | 3/2018 | Nguyen |
| 2018/0064944 A1 | 3/2018 | Grill et al. |
| 2018/0168905 A1 | 6/2018 | Goodall et al. |
| 2018/0169400 A1 | 6/2018 | Wong et al. |
| 2018/0214694 A1 | 8/2018 | Parramon |
| 2018/0221620 A1 | 8/2018 | Metzger |
| 2018/0235500 A1 | 8/2018 | Lee et al. |
| 2018/0264263 A1 | 9/2018 | Rosenbluth et al. |
| 2019/0001117 A1 | 1/2019 | Ben-David et al. |
| 2019/0001129 A1 | 1/2019 | Rosenbluth et al. |
| 2019/0134393 A1 | 5/2019 | Wong et al. |
| 2020/0093400 A1 | 3/2020 | Hamner et al. |

FOREIGN PATENT DOCUMENTS

| | | |
|---|---|---|
| EP | 0000759 | 2/1979 |
| EP | 0725665 | 1/1998 |
| EP | 1062988 | 12/2000 |
| EP | 1558333 | 5/2007 |
| EP | 2383014 | 11/2011 |
| EP | 2801389 | 11/2014 |
| EP | 3020448 | 5/2016 |
| ES | 2222819 | 3/2006 |
| ES | 2272137 | 6/2008 |
| GB | 2496449 | 5/2013 |
| JP | 2002/200178 | 7/2002 |
| JP | 2003-501207 | 1/2003 |
| JP | 2006-503658 | 2/2006 |
| JP | 2008/018235 | 1/2008 |
| JP | 2009/34328 | 2/2009 |
| JP | 2009/529352 | 8/2009 |
| JP | 2010/506618 | 3/2010 |
| JP | 2010/512926 | 4/2010 |
| JP | 2012/005596 | 1/2012 |
| JP | 2012/055650 | 3/2012 |
| JP | 2013/017609 | 1/2013 |
| JP | 2013/094305 | 5/2013 |
| JP | 54-39921 | 3/2014 |
| WO | WO1994/000187 | 1/1994 |
| WO | WO1994/017855 | 8/1994 |
| WO | WO1996/032909 | 10/1996 |
| WO | WO1998/043700 | 10/1998 |
| WO | WO1999/019019 | 4/1999 |
| WO | WO2000/015293 | 3/2000 |
| WO | WO2002/017987 | 3/2002 |
| WO | WO2005/122894 | 12/2005 |
| WO | WO2007/112092 | 10/2007 |
| WO | WO2009/153730 | 12/2009 |
| WO | WO2010/111321 | 9/2010 |
| WO | WO2010/141155 | 12/2010 |
| WO | WO2011/119224 | 9/2011 |
| WO | WO2011/144883 | 11/2011 |
| WO | WO2012/040243 | 3/2012 |
| WO | WO2013/071307 | 5/2013 |
| WO | WO2013/074809 | 5/2013 |
| WO | WO2014/043757 | 3/2014 |
| WO | WO2014/053041 | 4/2014 |
| WO | WO2014/113813 | 7/2014 |
| WO | WO2014/146082 | 9/2014 |
| WO | WO2014/151431 | 9/2014 |
| WO | WO2014/153201 | 9/2014 |
| WO | WO2014/207512 | 12/2014 |
| WO | WO2015/033152 | 3/2015 |
| WO | WO2015/039206 | 3/2015 |
| WO | WO2015/039244 | 3/2015 |
| WO | WO2015/042365 | 3/2015 |
| WO | WO2015/079319 | 6/2015 |
| WO | WO2015/095880 | 6/2015 |
| WO | WO2015/128090 | 9/2015 |
| WO | WO2015/164706 | 10/2015 |
| WO | WO2015/187712 | 12/2015 |
| WO | WO2016/007093 | 1/2016 |
| WO | WO2016/019250 | 2/2016 |
| WO | WO2016/094728 | 6/2016 |
| WO | WO2016/102958 | 6/2016 |
| WO | WO2016/110804 | 7/2016 |
| WO | WO2016/128985 | 8/2016 |
| WO | WO2016/149751 | 9/2016 |
| WO | WO2016/166281 | 10/2016 |
| WO | WO2016/179407 | 11/2016 |
| WO | WO2016/189422 | 12/2016 |
| WO | WO2016/195587 | 12/2016 |
| WO | WO2016/201366 | 12/2016 |
| WO | WO2017/004021 | 1/2017 |
| WO | WO2017/010930 | 1/2017 |
| WO | WO2017/023864 | 2/2017 |
| WO | WO2017/053847 | 3/2017 |
| WO | WO2017/062994 | 4/2017 |
| WO | WO2017/086798 | 5/2017 |
| WO | WO2017/088573 | 6/2017 |
| WO | WO2017/132067 | 8/2017 |
| WO | WO2017/199026 | 11/2017 |
| WO | WO2017/208167 | 12/2017 |
| WO | WO2017/209673 | 12/2017 |
| WO | WO2017/210729 | 12/2017 |
| WO | WO2017/221037 | 12/2017 |

(56) References Cited

FOREIGN PATENT DOCUMENTS

| WO | WO2018/009680 | 1/2018 |
|---|---|---|
| WO | WO2018/028170 | 2/2018 |
| WO | WO2018/028220 | 2/2018 |
| WO | WO2018/028221 | 2/2018 |
| WO | WO2018/039458 | 3/2018 |
| WO | WO2018/093765 | 5/2018 |
| WO | WO2018/112164 | 6/2018 |
| WO | WO2018/187241 | 10/2018 |
| WO | WO2019/005774 | 1/2019 |
| WO | WO2019/014250 | 1/2019 |
| WO | WO2019/028000 | 2/2019 |
| WO | WO 2019/143790 | 7/2019 |
| WO | WO 2019/213433 | 11/2019 |
| WO | WO 2020/006048 | 1/2020 |
| WO | WO2020/086726 | 4/2020 |

OTHER PUBLICATIONS

U.S. Appl. No. 16/327,780, filed Feb. 22, 2019, Hamner et al.
U.S. Appl. No. 16/833,388, filed Mar. 27, 2020, Hamner et al.
U.S. Appl. No. 16/780,758, filed Feb. 3, 20202, Wong et al.
Apartis; Clinical neurophysiology in movement disorders. Handb Clin Neurol; 111; Pediatric Neurology Pt. 1; pp. 87-92;Apr. 2013.
Barbaud et al.; Improvement in essential tremor after pure sensory stroke due to thalamic infarction; European neurology; 46; pp. 57-59; Jul. 2001.
Barrios et al.: BCI algorithms for tremor identification, characterization and tracking; Seventh Framework Programme, EU; Contract No. FP7-ICT-2007-224051 (v3.0); 57 pgs.; Jul. 10, 2011.
Bartley et al.; Neuromodulation for overactive bladder; Nature Reviews Urology; 10; pp. 513-521; Sep. 2013.
Benabid et al.; A putative generalized model of the effects and mechanism of action of high frequency electrical stimulation of the central nervous system; Acta Neural Belg; 105(3); pp. 149-157; Sep. 2005.
Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.
Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.
Bijelic et al.: E Actitrode®: The New Selective Stimulation Interface for Functional Movements in Hemiplegic Patients; Serbian Journal of Electrical Engineering; 1(3); pp. 21-28; Nov. 2004.
Birdno et al.; Pulse-to-pulse changes in the frequency of deep brain stimulation affect tremor and modeled neuronal activity.; Journal of Neurophysiology; 98; pp. 1675-1684; Jul. 2007.
Birdno et al.; Response of human thalamic neurons to high-frequency stimulation.; PloS One; 9(5); 10 pgs.; May 2014.
Birgersson et al.; Non-invasive bioimpedance of intact skin: mathematical modeling and experiments; Physiological Measurement; 32(1); pp. 1-18; Jan. 2011.
Bohling et al.; Comparison of the stratum corneum thickness measured in vivo with confocal Raman spectroscopy and confocal reflectance microscopy; Skin research and Technology; 20(1); pp. 50-47; Feb. 2014.
Bonaz, B., V. Sinniger, and S. Pellissier. "Vagus nerve stimulation: a new promising therapeutic tool in inflammatory bowel disease." Journal of internal medicine 282.1 (2017): 46-63.
Bowman et al.; Effects of waveform parameters on comfort during transcutaneous neuromuscular electrical stimulation; Annals of Biomedical Engineering; 13(1); pp. 59-74; Jan. 1985.
Bratton et al.; Neural regulation of inflammation: no neural connection from the vagus to splenic sympathetic neurons; Exp Physiol 97.11 (2012); pp. 1180-1185.
Brittain et al.; Tremor suppression by rhythmic transcranial current stimulation; Current Biology; 23; pp. 436-440; Mar. 2013.

Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.
Buschbacher et al.; Manual of nerve conduction series; 2nd edition; Demos Medical Publishing, LLC; 2006 (part 1, Title to p. #142).
Buschbacher et al.; Manual of nerve conduction series; 2nd edition; Demos Medical Publishing, LLC; 2006 (part 2, p. #143 to #299).
Cagnan et al.; Phase dependent modulation of tremor amplitude in essential tremor through thalamic stimulation; Brain; 136(10); pp. 3062-3075; Oct. 2013.
Campero et al.; Peripheral projections of sensory fasicles in the human superificial radial nerve; Brain; 128(Pt 4); pp. 892-895; Apr. 2005.
Chen et al.; A web-based system for home monitoring of patients with Parkinson's disease using wearable sensors; IEEE Trans on Bio-Medical Engineering; 58(3); pp. 831-836; Mar. 2011.
Choi, Jong Bo, et al. "Analysis of heart rate variability in female patients with overactive bladder." Urology 65.6 (2005): 1109-1112.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem.; 26; pp. 337-353; 1975; presented at IFSCC Vilith Int'l Congresson Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs.; Jan. 2012.
Deuschl et at; Consensus statement of the Movement Disorder Society on Tremor. Ad Hoc Scientific Committee., Movement Disorders, vol. 13 Suppl 3, pp. 2-23; (year of pub. sufficiently earlier than effective US filing date and any foreign priority date)1998.
Di Giovangiulio et al.; The Neuromodulation of the intestinal immune system and its relevance in inflammatory bowel disease; Fronteir's in Immunology; vol. 6; Article 590; Nov. 2015.
Dideriksen et al.; EMG-based characterization of pathological tremor using the iterated Hilbert transform; IEEE transactions on Bio-medical Engineering; 58(10); pp. 2911-2921; Oct. 2011.
Dosen et al.: Tremor suppression using electromyography and surface sensory electrical stimulation; Converging Clinical and Engineering Research on Neurorehabilitation; vol. 1 (Siosystems & Biorobotics Series); pp. 539-543; Feb. 2013.
Doucet et al.; Neuromuscular electrical stimulation for skeletal muscle function; The Yale Journal of Biology and Medicine; 85(2); pp. 201-215; Jun. 2012.
Extended European Search Report dated Jul. 29, 2019 in European Application No. 17744724.0 in 6 pages.
Fuentes et al.; Restoration of locomotive function in Parkinson's disease by spinal cord stimulation: mechanistic approach, Eur J Neurosci, vol. 32, pp. 1100-1108; Oct. 2010 (author manuscript; 19 pgs.).
Fuentes et al.; Spinal cord stimulation restores locomotion in animal models of Parkinson's disease; Science; 323; pp. 1578-1582; Mar. 2009.
Gallego et al.; A neuroprosthesis for tremor management through the control of muscle co-contraction; Journal of Neuroengineering and Rehabilitation; vol. 10; 36; (13 pgs); Apr. 2013.
Gallego et al.; A soft wearable robot for tremor assessment and suppression; 2011 IEEE International Conference on Robotics and Automation; Shanghai International Conference Center; pp. 2249-2254; May 9-13, 2011.
Gallego et al.; Real-time estimation of pathological tremor parameters from gyroscope data.; Sensors; 10(3); pp. 2129-2149; Mar. 2010.
Gao; Analysis of amplitude and frequency variations of essential and Parkinsonian tremors; Medical & Biological Engineering & Computing; 42(3); pp. 345-349; May 2004.

(56) References Cited

OTHER PUBLICATIONS

Garcia et al.; Modulation of brainstem activity and connectivity by respiratory-gated auricular vagal afferent nerve stimulation in migraine patients; PAIN; International Association for the Study of Pain; 2017.
Garcia-Rill, E., et al. "Arousal, motor control, and Parkinson's disease." Translational neuroscience 6.1 pp. 198-207 (2015).
Giuffridda et al.; Clinically deployable Kinesia technology for automated tremor assessment.; Movement Disorders; 24(5); pp. 723-730; Apr. 2009.
Gracanin et al.; Optimal stimulus parameters for minimum pain in the chronic stimulatin of innervated muscle; Archives of Physical Medicine and Rehabilitation; 56(6); pp. 243-249; Jun. 1975.
Haeri et al.; Modeling the Parkinson's tremor and its treatments; Journal of Theorectical Biology; 236(3); pp. 311-322; Oct. 2005.
Halon En et al.; Contribution of cutaneous and muscle afferent fibres to cortical SEPs following median and radial nerve stimulation in man; Electroenceph. Clin. Neurophysiol.; 71(5); pp. 331-335; Sep.-Oct. 1988.
Hao et al.; Effects of electrical stimulation of cutaneous afferents on corticospinal transmission of tremor signals in patients with Parkinson's disease; 6th International Conference on Neural Engineering; San Diego, CA; pp. 355-358; Nov. 2013.
Hauptmann et al.; External trial deep brain stimulation device for the application of desynchronizing stimulation techniques; Journal of Neural Engineering; 6; 12 pgs.; Oct. 2009.
Heller et al.; Automated setup of functional electrical stimulation for drop foot using a novel 64 channel prototype stimulator and electrode array: Results from a gait-lab based study; Medical Engineering & Physic; 35(1); pp. 74-81; Jan. 2013.
Henry Dreyfuss Associates; The Measure of Man and Woman: Human Factors in Design (Revised Edition); John Wiley & Sons, New York; pp. 10-11 and 22-25; Dec. 2001.
Hernan, Miguel, et al. "Alcohol Consumption and the Incidence of Parkinson's Disease." May 15, 2003. Annals of Neurology. vol. 54. pp. 170•175.
Hua et al.; Posture-related oscillations in human cerebellar thalamus in essential tremor are enabled by voluntary motor circuits; J Neurophysiol; 93(1); pp. 117-127; Jan. 2005.
Huang, et al.; Theta burst stimulation report of the human motor cortex; Neuron, vol. 45, 201-206, Jan. 20, 2005.
Hubeaux, Katelyne, et al. "Autonomic nervous system activity during bladder filling assessed by heart rate variability analysis in women with idiopathic overactive bladder syndrome or stress urinary incontinence." The Journal of urology 178.6 (2007): 2483-2487.
Hubeaux, Katelyne, et al. "Evidence for autonomic nervous system dysfunction in females with idiopathic overactive bladder syndrome." Neurourology and urodynamics 30.8 (2011): 1467-1472.
Inoue, Masahiro, Katsuaki Suganuma, and Hiroshi Ishiguro. "Stretchable human interface using a conductive silicone elastomer containing silver fillers." Consumer Electronics, 2009. ISCE'09. IEEE 13th International Symposium on. IEEE, 2009.
Jacks et al.; Instability in human forearm movements studied with feed-back-controlled electrical stimulation of muscles; Journal of Physiology; 402; pp. 443-461; Aug. 1988.
Jobges et al.; Vibratory proprioceptive stimulation affects Parkinsonian tremor; Parkinsonism & Related Disorders; 8(3); pp. 171-176; Jan. 2002.
Joundi et al.; Rapid tremor frequency assessment with the iPhone accelerometer.; Parkinsonism & Related Disorders; 17(4); pp. 288-290; May 2011.
Kim et al.: Adaptive control of movement for neuromuscular stimulation-assisted therapy in a rodent model; IEEE Trans on Biomedical Engineering,; 56(2); pp. 452-461; Feb. 2009.
Krauss et al.; Chronic spinal cord stimulation in medically intractable orthostatic tremor; J Neurol Neurosurg Psychiatry; 77(9); pp. 1013-1016; Sep. 2006.

Kuhn et al.; Array electrode design for transcutaneous electrical stimulation a simulation study; Medical Engineering & Physics; 31 (8); pp. 945-951; Oct. 2009.
Kuhn et al.; The Influence of Electrode Size on Selectivity and Comfort in Transcutaneous Electrical Stimulation of the Forearm; Neural Systems and Rehabilitation Engineering, IEEE Transactions on; 18(3); pp. 255-262; Jun. 2010.
Kunz, Patrik, et al. "5 kHz transcranial alternating current stimulation: lack of cortical excitability changes when grouped in a theta burst pattern." Frontiers in Human Neuroscience 10 (2016): 683.
Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.
Laroy et al.; The sensory innervation pattern of the fingers; J. Neurol.; 245 (5); pp. 294-298; May 1998.
Lee et al.; Resetting of tremor by mechanical perturbations: A comparison of essential tremor and parkinsonian tremor; Annals of Nuerology; 10(6); pp. 523-531; Dec. 1981.
Legon et al.; Pulsed ultrasound differentially stimulates somatosensory circuits in humans as indicated by EEG and fMRI; PLoS ONE; 7(12); e51177; 14 pgs.; Dec. 2012.
Liao, Wen-Chien, et al. "A noninvasive evaluation of autonomic nervous system dysfunction in women with an overactive bladder." International Journal of Gynecology & Obstetrics 110.1 (2010): 12-17.
Lourenco et al.; Effects produced in human arm and forearm motoneurones after electrical stimulation of ulnar and median nerves at wrist level; Experimental Brain Research; 178(2); pp. 267-284; Apr. 2007.
Malek et al.; The utility of electromyography and mechanomyography for assessing neuromuscular function: a noninvasive approach; Phys Med Rehabil in N Am; 23(1); pp. 23-32; Feb. 2012.
Mamorita et al.; Development of a system for measurement and analysis of tremor using a three-axis accelerometer; Methods Inf Med; 48(6); pp. 589-594; epub Nov. 2009.
Maneski et al.; Electrical Stimulation for suppression of pathological tremor; Med Biol Eng Comput; 49(10); pp. 1187-1193; Oct. 2011.
Marsden et al.; Coherence between cerebellar thalamus, cortex and muscle in man; Brain; 123; pp. 1459-1470; Jul. 2000.
Marshall, Ryan, et al. "Bioelectrical stimulation for the reduction of inflammation in inflammatory bowel disease." Clinical Medicine Insights: Gastroenterology 8 (2015): CGast-S31779.
McAuley et al.; Physiological and pathological tremors and rhythmic central motor control; Brain; 123(Pt 8); pp. 1545-1567; Aug. 2000.
McIntyre et al.; Finite element analysis of current-density and electric field generated by metal microelectrodes; Annals of Biomedical Engineering; 29(3); pp. 227-235; Mar. 2001.
Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.
Mehnert, Ulrich, et al. "Heart rate variability: an objective measure of autonomic activity and bladder sensations during urodynamics." Neurourology and urodynamics 28.4 (2009): 313-319.
Miguel et al.; Alcohol consumption and the incidence of Parkinson's disease; Ann. Neurol.; 54(2); pp. 170-175; May 15, 2003.
Miller et al.; Multiplexed microneedle-based biosensor array for characterization of metabolic acidosis; Talanta; 88; pp. 739-742; Jan. 2012 (author manuscript; 13 pgs.).
Miller et al.; Neurostimulation in the treatment of primary headaches; Pract Neurol; Apr. 11, 2016;16:pp. 362-375.
Milne et al.; Habituation to repeated in painful and non-painful cutaneous stimuli: A quantitative psychophysical study; Experimental Brain Research; 87(2); pp. 438-444; Nov. 1991.
Mommaerts et al.; Excitation and nerve conduction; in Comprehensive Human Physiology; Springer Berlin Heidelberg; Chap. 13; pp. 283-294; Mar. 1996.
Mones et al.; The response of the tremor of patients with Parkinsonism to peripheral nerve stimulation; J Neurology, Neurosurgery, and Psychiatry; 32(6); pp. 512-518; Dec. 1969.

(56) References Cited

OTHER PUBLICATIONS

Morgante et al.: How many parkinsonian patients are suitable candidates for deep brain stimulation of subthalamic nucleus?; Results of a Questionnaire, Partkinsonism Relat Disord; 13; pp. 528-531; Dec. 2007.
Munhoz et al.; Acute effect of transcutaneous electrical nerve stimulation on tremor; Movement Disorders; 18(2); pp. 191-194; Feb. 2003.
Nardone et al.; Influences of transcutaneous electrical stimulation of cutaneous and mixed nerves on subcortical somatosensory evoked potentials; Electroenceph. Clin. Neurophysiol.; 74(1); pp. 24-35; Jan.-Feb. 1989.
Nonis et al.; Evidence of activation of vagal afferents by non-invasive vagus nerve stimulation: An electrophysiological study in healthy volunteers; Cephalalgia; pp. 1285-1293; vol. 37(13); Mar. 28, 2017.
PCT Search Report and Written Opinion in PCT Application No. PCT/US2017/014431 dated Sep. 7, 2017 in 19 pages.
PCT Search Report and Written Opinion in PCT Application No. PCT/US2018/025752 dated Jun. 21, 2018 in 21 pages.
Perez et al.; Patterned Sensory Stimulation Induces Plasticity in Reciprocal Ia Inhibition in Humans; The Journal of Neuroscience; 23(6); pp. 2014-2018; Mar. 2003.
Perlmutter et al.; Deep brain stimulation; Ann Rev Neurosci; 29; pp. 229-257; Jul. 2006.
Popović-Bijelić, Ana, et al. "Multi-field surface electrode for selective electrical stimulation." Artificial organs 29.6 (2005): 448-452.
Popovi Maneski et al.; Electrical stimulation for the suppression of pathological tremor; Medical & Biological Engineering & Computing; 49(10); pp. 1187-1193; Oct. 2011.
Prochazka et al.; Attenuation of pathological tremors by functional electrical stimulation I: Method; Annals of Biomedical Engineering; 20(2); pp. 205-224; Mar. 1992.
Pulliam et al.; Continuous in-home monitoring of essential tremor; Parkinsonism Relat Disord; 20(1); pp. 37-40; Jan. 2014.
Quattrini et al.; Understanding the impact of painful diabetic neuropathy; Diabetes/Metabolism Research and Reviews; 19, Suppl. 1; pp. S2-8; Jan.-Feb. 2003.
Rocon et al.; Design and validation of a rehabilitation robotic exoskeleton for tremor assessment and suppression; IEEE Trans Neural Sys and Rehab Eng.; 15(3); pp. 367-378; Sep. 2007.
Silverstone et al.; Non-Invasive Neurostimulation In The Control of Familial Essential Tremor Using The Synaptic Neuromodulator; Conference Proceedings, International Functional Electrical Stimulation Society (IFES); Ed. Paul Meadows; 3 pgs.; May 1999.
Singer et al.; The effect of EMG triggered electrical stimulation plus task practice on arm function in chronic stroke patients with moderate-severe arm deficits; Restor Neurol Neurosci; 31(6); pp. 681-691; Oct. 2013.
Straube et al.; Treatment of chronic migraine with transcutaneous stimulation of the auricular branch of the vagal nerve (auricular t-VNS): a randomized, monocentric clinical trial; The Journal of Headache and Pain (2015) 16:63.
Takanashi et al.; A functional MRI study of somatotopic representation of somatosensory stimulation in the cerebellum; Neuroradiology; 45(3); pp. 149-152; Mar. 2003.

Tass et al.; Coordinated reset has sustained aftereffects in Parkinsonian monkeys; Ann Neurol; 72(5); pp. 816-820; Nov. 2012.
Tass et al.; Counteracting tinnitus by acoustic coordinated reset neuromodulation; Restorative neurology and Neuroscience; 30(2); pp. 137-159; Apr. 2012.
Tass; A Model of desynchronizing deep brain stimulation with a demand-controlled coordinated reset of neural subpopulations; Bioi Cybern; 89(2); pp. 81-88; Aug. 2003.
Thomas et al.; A review of posterior tibial nerve stimulation for faecal incontinence; Colorectal Disease; 2012 The Association of Coloproctology of Great Britain and Ireland. 15, pp. 519-526; Jun. 25, 2012.
Toloso et al.; Essential tremor: treatment with propranolol; Neurology; 25(11); pp. 1041; Nov. 1975.
Tracey; The inflammatory reflex; Nature; vol. 420; pp. 853-859; Dec. 19/26, 2002.
Treager; Interpretation of skin impedance measurements; Nature; 205; pp. 600-601; Feb. 1965.
Valente; Novel methods and circuits for field shaping in deep brain stimulation; Doctoral thesis, UCL (University College London); 222 pgs.; 2011.
Vitton et al.; Transcutaneous posterior tibial nerve stimulation for fecalIncontinence in inflammatory bowel disease patients: a therapeutic option?; Inflamm Bowel Dis; vol. 15, No. 3, Mar. 2009; pp. 402-405.
Von Lewinski et al.; Efficacy of EMG-triggered electrical arm stimulation in chronic hemiparetic stroke patients; Restor Neurol Neurosci; 27(3); pp. 189-197; Jun. 2009.
Wardman et al.; Subcortical, and cerebellar activation evoked by selective stimulation of muscle and cataneous afferents: an fMRI study; Physiol. Rep.; 2(4); pp. 1-16; Apr. 2014.
Wiestler et al.; Integration of sensory and motor representations of single fingers in the human; J. Neurophysiol.; 105(6); pp. 3042-3053; Jun. 2011.
Woldag et al.; Evidence-based physiotherapeutic concepts for improving arm and hand function in stroke patients R A review; J Neurol; 249(5); pp. 518-528; May 2002.
Woolf et al.; Peripheral nerve injury triggers central sprouting of myelinated afferents; Nature; 355(6355); pp. 75-78; Jan. 1992.
Yarnitsky et al.; Nonpainful remote electrical stimulation alleviates episodic migraine pain; Neurology 88; pp. 1250-1255; Mar. 28, 2017.
Yeh, Kuei-Lin, Po-Yu Fong, and Ying-Zu Huang. "Intensity sensitive modulation effect of theta burst form of median nerve stimulation on the monosynaptic spinal reflex." Neural plasticity 2015 (2015) in 8 pages.
Yilmaz, Ozlem O., et al. "Efficacy of EMG-biofeedback in knee osteoarthritis." Rheumatology international 30.7 (2010): 887-892.
Zhang et al.; Neural oscillator based control for pathological tremor suppression via functional electrical stimulation; Control Engineering Practice; 19(1); pp. 74-88; Jan. 2011.
Zorba et al.; Overactive bladder and the pons; Rize University, Medical Faculty, Department of Urology; 123-124; Undated.
Zwarts et al.; Multichannel surface EMG: basic aspects and clinical utility; Muscle Nerve; 28(1); pp. 1-17; Jul. 2003.

\* cited by examiner

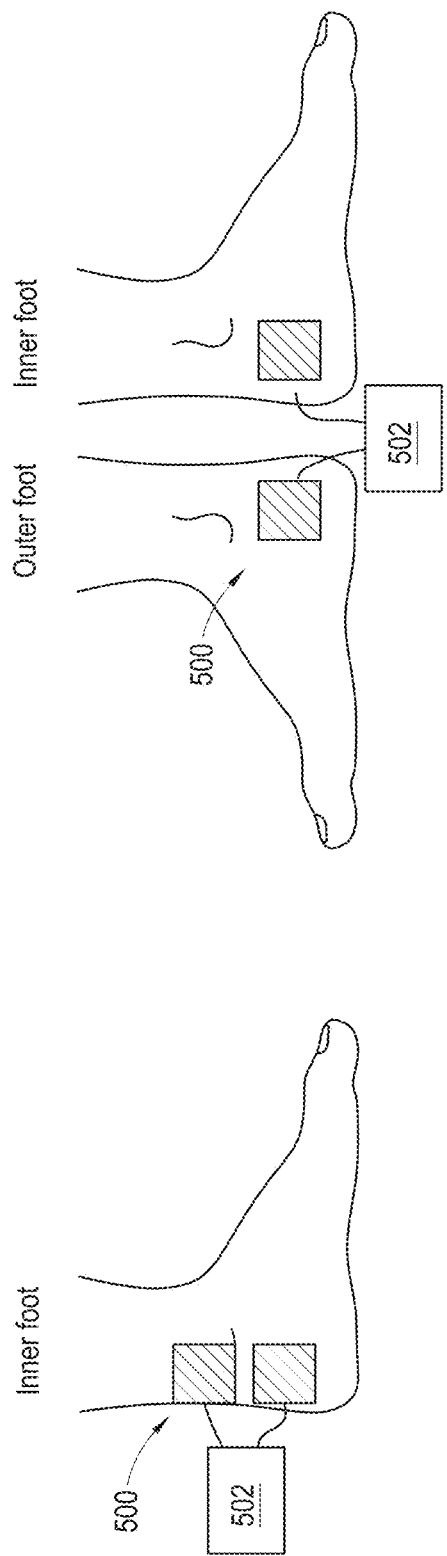
FIG. 5A
FIG. 5B
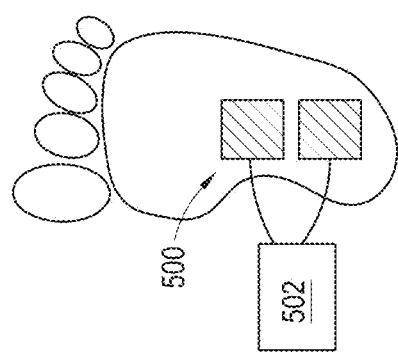
FIG. 5C

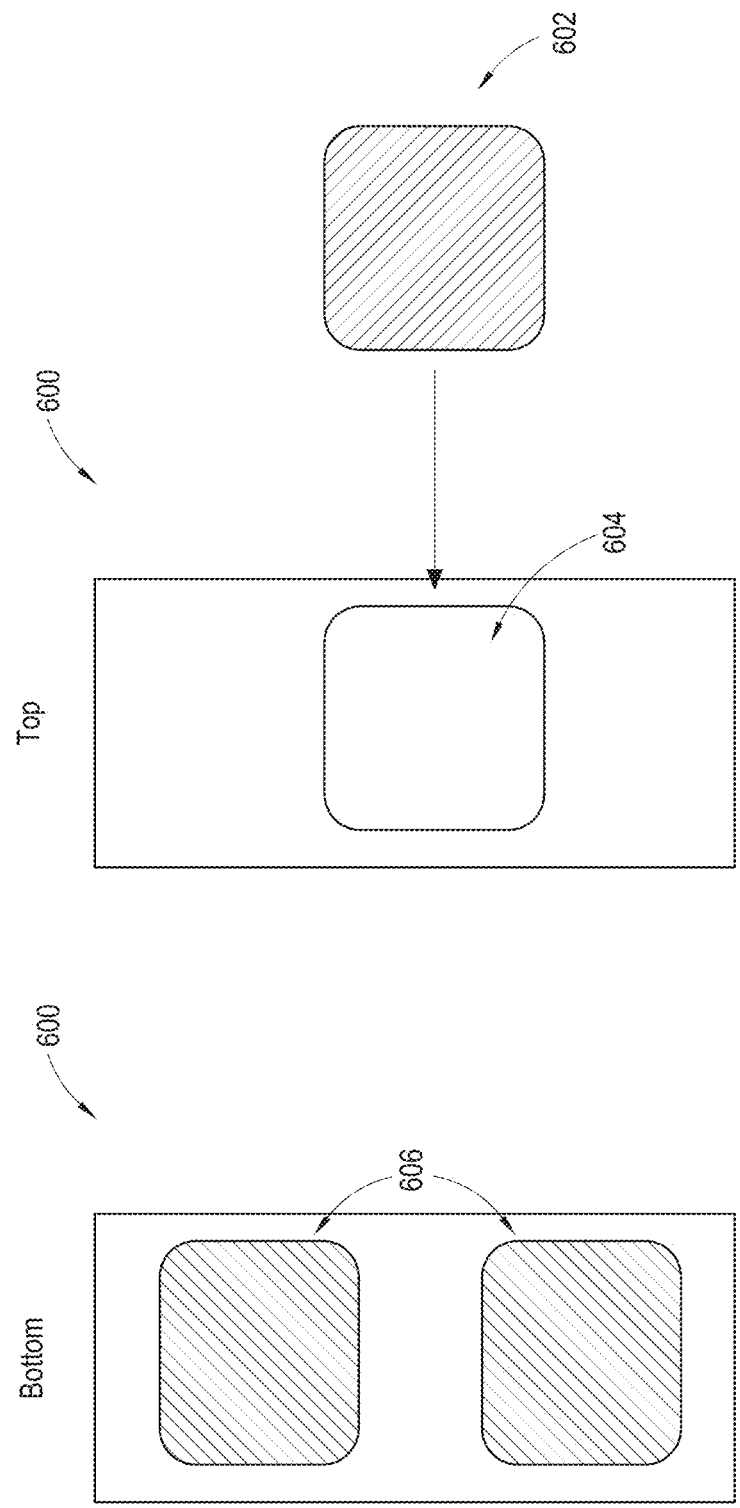

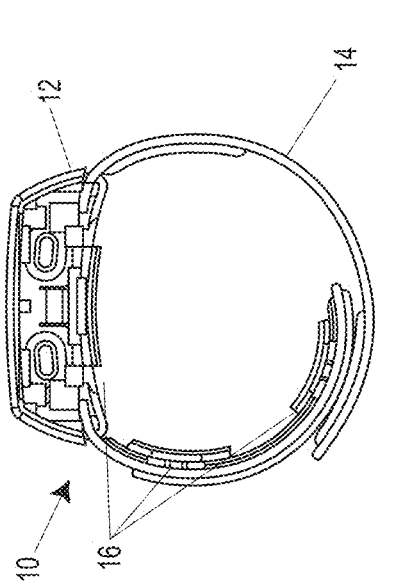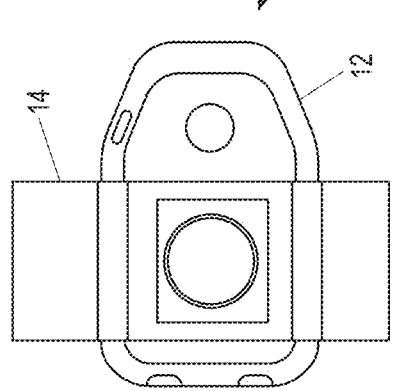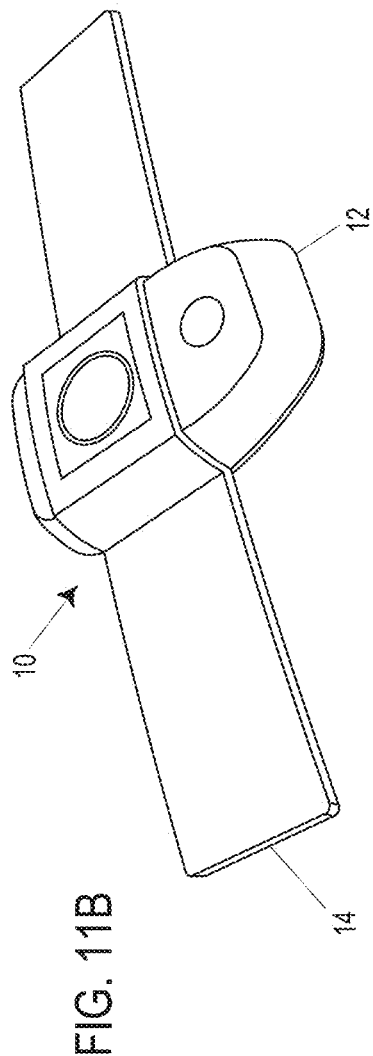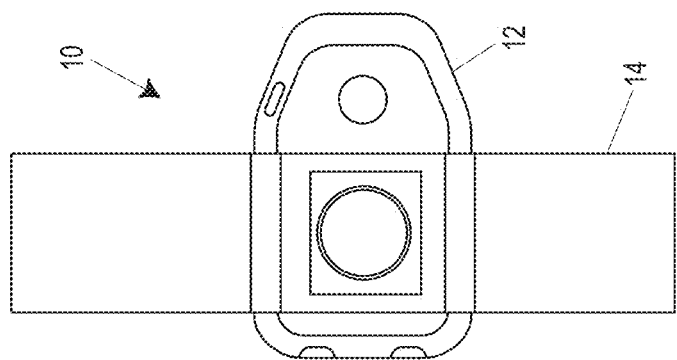

Subject baseline parameters

| Age (years) | 73.5 (±8.4) N = 4 |
|---|---|
| OAB-V8 Score* | 21.5 (±7.5) |
| Frequency (Episodes/24 hours) | 11.7 (±0.5) |
| Incontinence (Episodes/24 hours) | 2.4 (±1.0) |
| Nocturia | 2.7 (±2.0) |

* OAB-V8 Score > 8 is consistent with overactive bladder

FIG. 17A

Responder rate

| | Nocturia | Incontinence | Frequency |
|---|---|---|---|
| Responder rate | 4/4 (100%) | 2/3 (67%)* | 3/4 (75%) |

Responder rate: > 30% improvement in symptom parameter; for nocturia and incontinence, improvement was 50% in all subjects seen

* One subject with no urinary incontinence

FIG. 17B

Improvement in Urinary Parameters

|  | Baseline | Post Stimulation (4 weeks) |
|---|---|---|
| Frequency (Episodes/24 hours) | 11.7 (±0.5) | 8.9 (±2.0) |
| Incontinence (Episodes/24 hours) | 2.4 (±1.0) | 1.3 (±0.3) |
| Nocturia | 2.7 (±2.0) | 1.4 (±0.4) |

SYSTEMS, METHODS AND DEVICES FOR PERIPHERAL NEUROMODULATION FOR TREATING DISEASES RELATED TO OVERACTIVE BLADDER

INCORPORATION BY REFERENCE

This application is the U.S. National Stage under 37 C.F.R. § 371 of PCT App. No. PCT/US2018/025752 filed on Apr. 2, 2018, which in turn claims the benefit under 35 U.S.C. 119(e) as a nonprovisional application of U.S. Prov. App. No. 62/481,006 filed on Apr. 3, 2017 and U.S. Prov. App. No. 62/534,074 filed on Jul. 18, 2017, both of which are incorporated by reference in their entireties. This application is also related to PCT App. No. PCT/US2017/014431 filed on Jan. 20, 2017, which is a nonprovisional application that claims the benefit under 35 U.S.C. § 119(e) of U.S. Prov. App. No. 62/281,606 filed on Jan. 21, 2016, U.S. Prov. App. No. 62/352,462 filed on Jun. 20, 2016, and U.S. Prov. App. No. 62/365,326 filed on Jul. 21, 2016, each of which are hereby incorporated by reference in their entireties.

BACKGROUND

Field of the Invention

The invention relates in some aspects to systems and methods for treating overactive bladder and related conditions.

Description of the Related Art

Overactive bladder (OAB) is a common urinary syndrome affecting men and women with an estimated prevalence of 16% of the population. The total annual cost burden of OAB is projected to be up to US$3.9 billion across six countries (Canada, Germany, Italy, Spain, Sweden, and the UK). Symptoms of overactive bladder include the uncontrollable desire to urinate immediately, known as urgency, which may or may not be followed by the involuntary loss of urine (incontinence), increased frequency of urination during the day, and/or increased frequency of waking up from sleep due to a sense of urgency, also known as nocturia. Nocturia is a medical condition that results in the need to wake up two, three, or more times during the night to urinate. Lower urinary tract (LUT) dysfunction may be secondary to a variety of non-neurologic or neurologic causes, including stroke, spinal cord injury, multiple sclerosis or neurodegenerative conditions such as Parkinson's disease. Standard medical treatment options for overactive bladder include behavioral strategies such as restricting fluid intake, timed voiding, or pelvic muscle exercises, or pharmacologic therapies such as antimuscarinic medications or botulinum toxin injections into the bladder. However, oral medications can be incompletely effective and carry a high risk of adverse side effects leading to intolerance and frequent discontinuation. Efficacious therapies with reduced side effects are needed.

SUMMARY

In some embodiments, disclosed herein is a method of treating urinary symptoms in a patient with dual transcutaneous stimulation of a saphenous nerve and a tibial nerve. The method can include, in some embodiments, any number of the following: positioning a first peripheral nerve effector on the patient's skin to stimulate the saphenous nerve of the patient; positioning a second peripheral nerve effector on the patient's skin to stimulate the tibial nerve of the patient; delivering a first electrical nerve stimulation signal transcutaneously to the saphenous nerve through the first peripheral nerve effector; delivering a second electrical nerve stimulation signal transcutaneously to the tibial nerve through the second peripheral nerve effector; receiving an input relating to autonomic nervous system activity of the patient; and modifying at least one brain or spinal cord autonomic feedback loop relating to bladder function based on the input to balance parasympathetic and sympathetic nervous system activity of the patient. In some embodiments, the method does not utilize any implantable components, and only involves transcutaneous stimulation. The first peripheral nerve effector and the second peripheral nerve effector can be both positioned proximate the knee of the patient. The first electrical stimulation signal can be different from the second electrical stimulation signal. The first electrical stimulation signal can have a first frequency different from a second frequency of the second electrical stimulation signal. The first electrical stimulation signal can have an amplitude different from the second electrical stimulation signal. The first or second frequency can be, for example, from about 10 Hz to about 20 Hz. The first or second frequency can be, for example, from about 5 Hz to about 30 Hz. Receiving an input relating to autonomic nervous system activity of the patient can include any number of the following: receiving data from a sensor that measures autonomic nervous system activity of the patient; receiving data from a sensor that measures heart rate variability of the patient; receiving heart rate variability data from an optical sensor measuring blood flow characteristics and disposed proximate a vessel proximate a knee of the patient; receiving data from a sensor that measures galvanic skin response of the patient; receiving data relating to urinary symptoms of the patient; and/or receiving data relating to nocturia episodes of the patient.

Also disclosed herein is a wearable device for dual transcutaneous stimulation of the saphenous nerve and tibial nerve and for treating urinary symptoms in a patient. The device can include, in some embodiments, any number of the following features: a controller; a first peripheral nerve effector, comprising at least one stimulation electrode configured to be positioned to transcutaneously modulate the saphenous nerve; a second peripheral nerve effector, comprising at least one stimulation electrode configured to be positioned to transcutaneously modulate the tibial nerve; and at least one biomedical sensor or data input source configured to provide feedback information. The controller can include a processor and a memory for receiving the feedback information from the sensor that, when executed by the processor, cause the device to adjust one or more parameters of a first electrical stimulus and a second electrical stimulus based at least in part on the feedback information; and/or deliver the first electrical stimulus to the saphenous nerve through the first peripheral nerve effector and deliver the second electrical stimulus to the tibial nerve through the second peripheral nerve effector to reduce urinary symptoms by modifying a brain or spinal cord autonomic feedback loop relating to bladder function and balancing sympathetic nerve and parasympathetic nerve activity. In some embodiments, the device is not configured for implantation within the patient. The feedback information can include real-time feedback information. The first electrical stimulus can have a frequency of, for example, between about 10 Hz and about 20 Hz. The second electrical stimulus can have a frequency of, for example, between about 5 Hz and about 30 Hz. The feedback information can include autonomic nervous system activity of the patient. The feedback information can include heart rate variability. The feedback information can also include information relating to nocturia events of the patient. The feedback information can also include information relating to patient sleep state.

In some embodiments, disclosed herein is a method of treating urinary symptoms in a patient. The method can include any number of the following: positioning a first electrode at a first location on a skin surface relative to a first afferent peripheral nerve; positioning a second electrode at a second location on the skin surface relative to a second afferent peripheral nerve; positioning a third electrode at a third location on the skin surface spaced apart from the first electrode and the second electrode; delivering a first stimulus to the first peripheral nerve through the first electrode; and delivering a second stimulus to the second peripheral nerve through the second electrode. In some embodiments, the third electrode is a single common return electrode (which can be referred to as a counter electrode or ground electrode) to the first electrode and the second electrode. In some embodiments, the first electrode, second electrode, and third electrode are positioned such that electric fields between the first electrode and the third electrode pass through the first afferent peripheral nerve to preferentially stimulate the first afferent peripheral nerve, and electric fields between the second electrode and the third electrode pass through the second afferent peripheral nerve to preferentially stimulate the second afferent peripheral nerve. The first stimulus and the second stimulus can modify at least one brain or spinal cord autonomic feedback loop relating to bladder function. In some embodiments, the first afferent peripheral nerve comprises the tibial nerve. In some embodiments, the second afferent peripheral nerve comprises the saphenous nerve. The symptoms can include, for example, overactive bladder, nocturia, urinary urgency, urinary incontinence, and/or urinary frequency. In some embodiments, the first electrode, second electrode, and third electrode are all connected on a wearable device and positioned on the calf proximate to, and distal to the patient's knee, ankle, and/or foot.

In some embodiments, disclosed herein is a method of treating urinary symptoms in a patient. The method can include any number of the following: positioning a first pair of electrodes comprising an anode and a cathode at a first location on a skin surface relative to a first peripheral nerve; positioning a second pair of electrodes comprising an anode and a cathode at a second location on the skin surface relative to a second peripheral nerve; delivering a first stimulus to the first peripheral nerve through the first pair of electrodes; and delivering a second stimulus to the second peripheral nerve through the second pair of electrodes. In some embodiments, the first pair of electrodes and second pair of electrodes are positioned such that electric fields between the first pair of electrodes pass through the first peripheral nerve, and electric fields between the second pair of electrodes pass through the second peripheral nerve. The first stimulus and the second stimulus can modify at least one brain or spinal cord autonomic feedback loop relating to bladder function.

Also disclosed herein is a system of treating urinary symptoms in a patient, that can include in some embodiments any number of the following: a wearable housing configured to be positioned on a patient's calf proximate the knee or ankle of the patient; a first electrode configured to be positioned at a first location on a skin surface relative to a first afferent peripheral nerve; a second electrode configured to be positioned at a second location on the skin surface relative to a second afferent peripheral nerve; a third electrode configured to be positioned at a third location on the skin surface spaced apart from the first electrode and the second electrode; a controller configured to deliver a first stimulus to the first peripheral nerve through the first electrode; and a second stimulus to the second peripheral nerve through the second electrode to modify at least one brain or spinal cord autonomic feedback loop relating to bladder function. The third electrode can be a single common return electrode to the first electrode and the second electrode. The first electrode, second electrode, and third electrode can be configured to be positioned such that electric fields between the first electrode and the third electrode pass through the first afferent peripheral nerve, and electric fields between the second electrode and the third electrode pass through the second afferent peripheral nerve. The wearable housing can be attached to each of the first electrode, the second electrode, and the third electrode. In some embodiments, the first afferent peripheral nerve is the tibial nerve, and the second afferent peripheral nerve is the saphenous nerve.

Also disclosed herein is a system of treating urinary symptoms in a patient, the system including any number of the following: a first pair of electrodes comprising an anode and a cathode and configured to be positioned at a first location on a skin surface relative to a first afferent peripheral nerve; a second pair of electrodes comprising an anode and a cathode and configured to be positioned at a second location on the skin surface relative to a second afferent peripheral nerve; a controller configured to deliver a first stimulus to the first peripheral nerve through the first pair of electrodes; and a second stimulus to the second peripheral nerve through the pair of second electrodes to modify at least one brain or spinal cord autonomic feedback loop relating to bladder function. The first pair of electrodes and second pair of electrodes can be configured to be positioned such that electric fields between the first pair of electrodes pass through the first peripheral nerve, and electric fields between the second pair of electrodes pass through the second peripheral nerve.

In some embodiments, disclosed herein is a wearable device for treating urinary symptoms in a patient. The device can include any number of the following: a controller; a first peripheral nerve effector, comprising at least one stimulation electrode configured to be positioned to transcutaneously modulate a first afferent nerve pathway associated with bladder function; and a second peripheral nerve effector, comprising at least one stimulation electrode configured to be positioned to transcutaneously modulate a second afferent nerve pathway associated with bladder function; and at least one input source configured to provide feedback information. The controller can include a processor and a memory for receiving the real-time feedback information from the input source that, when executed by the processor, cause the device to adjust one or more parameters of a first electrical stimulus based at least in part on the feedback information; adjust one or more parameters of a second electrical stimulus based at least in part on the feedback information independent from the first electrical stimulus; deliver the first electrical stimulus to a first afferent nerve pathway through the first peripheral nerve effector to reduce urinary symptoms by modifying a first brain or spinal cord autonomic feedback loop relating to bladder function; and deliver the second electrical stimulus to a second afferent nerve pathway through the second peripheral nerve effector to reduce urinary symptoms by modifying a second brain or spinal cord autonomic feedback loop relating to bladder function. Adjusting the one or more parameters of the first electrical stimulus and the second electrical stimulus can contribute to balancing sympathetic and parasympathetic nervous system activity.

In some embodiments, systems and methods can include a wearable device with an electrically conductive skin interface that excite the underlying nerves from a transcutaneous surface stimulator. The device may be sized for a range of user sizes with stimulation electrodes positioned to target the appropriate nerves, as in the device described in, for example, U.S. Pat. No. 9,452,287 to Rosenbluth et al., PCT Pub. No. WO 2015/187712 to Wong et al., and PCT App. No. PCT/US2016/037080, each of which is incorporated by reference in their entireties.

This invention describes, in some embodiments, a wearable system that uses transcutaneous sensory stimulation in order to improve symptoms of overactive bladder and urinary incontinence. In some embodiments, key factors of this system enable chronic, home-use to improve the efficacy of peripheral nerve stimulation by avoiding the inconvenience of frequent office visits and invasive aspects of using percutaneous tibial neuromodulation or sacral nerve stimulation. Some embodiments can advantageously utilize transcutaneous neuromodulation of peripheral afferent nerve pathways to non-invasively affect brain or spinal cord pathways associated with physiologic regulation, such as bladder function.

Chronic peripheral nerve stimulation in a wearable form that can be integrated easily into an individual's life, allowing full mobility and ease of use, can improve the efficacy of urinary neuromodulation. However, home use of a percutaneous system can be inconvenient and technically difficult for the patient. Transcutaneous neuromodulation is a more suitable modality for home use but is currently limited by the form factor depending on the needs for chronic daily use. Furthermore, adding aspects of responsiveness and more frequent use could greatly improve the effectiveness and comfort of such a chronic use device.

The effects of peripheral nerve stimulation on bladder function may occur only during the period of active stimulation or may outlast the stimulation period after stimulation has ceased. Different mechanisms such as the modulation of urinary reflexes or induction of brain or spinal plasticity can be responsible for these experimental and clinical observations. Furthermore, the onset of the effects of stimulation may occur acutely (e.g., during or immediately following therapy) or only after several stimulation sessions in a chronic manner. For example, the effect of transcutaneous tibial and/or saphenous nerve stimulation on patient related outcomes is estimated to be up to 4-6 weeks after the initiation of weekly stimulation sessions. Depending on the underlying mechanisms and the time course of beneficial effects, stimulation may require delivery in a continuous fashion such as in sacral nerve stimulation, in discrete scheduled sessions such as once per day, or in an on-demand, conditional manner. Conditional stimulation may either rely on patient control to identify the sense of urinary urge or automated detection of an involuntary detrusor contraction (IDC) which is responsible for urgency symptoms or evolution to frank incontinence.

Several peripheral nerves can be selected as targets for urinary neuromodulation, including the tibial, pudendal, and dorsal genital nerve, with demonstrated acute and chronic effects on bladder function in animal and human experimental studies. The saphenous nerve can acutely reduce bladder hyperexcitability. The saphenous nerve is a purely sensory nerve that innervates the skin on the medial lower leg. Its proximity to the skin surface makes it an advantageous target for transcutaneous stimulation. Selective stimulation of the tibial and saphenous nerve can reduce symptoms of overactive bladder. In some embodiments, disclosed herein is a wearable device for inducing neural plasticity in a user with transcutaneous electrical stimulation of an afferent peripheral nerve. The device can include any number of a controller; a first peripheral nerve effector, comprising at least one stimulation electrode configured to be positioned to transcutaneously modulate a first afferent peripheral nerve; and at least one biomedical sensor or data input source configured to provide feedback information. The controller can include a processor and a memory for receiving the feedback information from the sensor, that when executed by the processor, cause the device to adjust one or more parameters of a first electrical stimulus based at least in part on the feedback information; and/or deliver the first electrical stimulus to the first afferent peripheral nerve to the first peripheral nerve effector. The first electrical stimulus can include patterned, such as burst (e.g., theta burst) electrical stimulation configured to induce neural plasticity. The stimulation can be continuous, intermittent, or intermediate theta burst stimulation in some embodiments. The device can also be configured to deliver a priming electrical nerve stimulation signal prior to the first electrical stimulation signal, which can be a non-theta burst stimulation signal. The device can further include a second peripheral nerve effector, including at least one stimulation electrode configured to be positioned to transcutaneously modulate a second afferent peripheral nerve, and is configured to deliver a second electrical nerve stimulation signal transcutaneously to the afferent peripheral nerve of the user. The signal can include, for example, electrical theta burst stimulation. Also disclosed herein is a method for treating overactive bladder, that can include assessing at least one of sympathetic and parasympathetic activity of a subject and determining the presence of sympathetic or parasympathetic overactivity in the subject; and not to be limited by theory, stimulating the saphenous nerve sufficient to have a therapeutic effect on overactive bladder if abnormal sympathetic activity is present; and/or stimulating the tibial nerve sufficient to have a therapeutic effect on overactive bladder if abnormal parasympathetic activity is present. In some embodiments, stimulating comprises only electrical transcutaneous stimulation. The stimulation can include inhibiting or exciting nerve activity of either or both of the saphenous nerve, tibial nerve, sacral nerve, peroneal nerve, or other target nerves. Sympathetic and parasympathetic activity of a subject can include measuring heart rate variability (HRV), such as via a wrist-worn device. Other parameters such as heart rate and electrodermal activity can be measured in addition or alternatively. HRV can be measured during a bladder filling procedure, such as urodynamic cystography, either prior to and/or after the initial stimulation. Also disclosed herein in some embodiments is a method for treating overactive bladder, that can include electrically stimulating a first nerve associated with bladder function; assessing at least one of sympathetic and parasympathetic activity of a subject and determining the presence or absence of sympathetic or parasympathetic overactivity in the subject; assessing symptomatology of overactive bladder; and adjusting the electrical stimulation based upon assessing the at least one of sympathetic and parasympathetic activity and the symptomatology of overactive bladder. Adjusting the electrical stimulation can include, for example, identifying sympathetic or parasympathetic overactivity in the patient, and adjusting the frequency of stimulation of the first nerve;

and/or discontinuing electrical stimulation of the first nerve associated with bladder function; and initiating electrical stimulation of a second nerve associated with bladder function. In some embodiments, the first electrical stimulation includes a randomized stimulation parameter including one or more of: pulse width, frequency, and amplitude.

In some embodiments, also disclosed herein is method of treating urinary symptoms in a patient with dual transcutaneous stimulation of a first afferent lower extremity nerve and a second afferent lower extremity nerve. The method can include any number of the following: positioning a first peripheral nerve effector on the patient's skin to stimulate the first afferent lower extremity nerve of the patient; positioning a second peripheral nerve effector on the patient's skin to stimulate the second afferent lower extremity nerve of the patient; delivering a first electrical nerve stimulation signal transcutaneously to the first afferent lower extremity nerve through the first peripheral nerve effector; delivering a second electrical nerve stimulation signal transcutaneously to the second afferent lower extremity nerve through the second peripheral nerve effector; receiving an input relating to autonomic nervous system activity of the patient; and modifying at least one brain or spinal cord autonomic feedback loop relating to bladder function based on the input to balance parasympathetic and sympathetic nervous system activity of the patient. The method does or does not in some cases utilize any implantable components. In some embodiments, the method involves transcutaneous stimulation. The first electrical stimulation signal and the second electrical stimulation signal can include burst electrical stimulation signals, wherein the burst electrical stimulation signals induce neural plasticity. The burst stimulation signals can include, for example, alpha, delta, or theta burst stimulation, e.g., continuous, intermittent, or intermediate theta burst stimulation. The first electrical stimulation can include a stimulation parameter modulated within a range from a first lower predetermined value to a second higher predetermined value, wherein the stimulation parameter is selected from the group consisting of pulse width, frequency, and amplitude. The first peripheral nerve effector can be physically connected, or not physically connected to the second peripheral nerve effector. The first electrical stimulation signal can be stimulatory or inhibitory to the first afferent lower extremity peripheral nerve. In some cases, the first electrical stimulation signal can be stimulatory to the first afferent lower extremity peripheral nerve, and the second electrical stimulatory signal can be inhibitory to the second afferent lower extremity peripheral nerve. The method can also include delivering a priming electrical nerve stimulation signal prior to the first electrical stimulation signal. The priming electrical nerve stimulation signal can be a non-theta burst stimulation signal. The method can also include alternating the first electrical nerve stimulation signal to the first afferent lower extremity peripheral nerve and the second peripheral nerve signal to the second afferent lower extremity peripheral nerve. The first afferent lower extremity peripheral nerve can be, for example, one of the saphenous nerve and a tibial nerve. The method can treat a variety of conditions, including overactive bladder, nocturia, or stress incontinence of the user. The method can also include delivering brain stimulation to induce oscillatory activity in the brain; and synchronizing the first electrical nerve stimulation signal to the first afferent lower extremity peripheral nerve with the oscillatory activity in the brain. The method can also include delivering noninvasive transcranial direct current stimulation or noninvasive transcranial magnetic stimulation to the brain; and synchronizing the transcranial stimulation with the first electrical nerve stimulation signal to the first afferent lower extremity peripheral nerve. The method can further include delivering a priming stimulus prior to the first electrical stimulation signal. Delivering the priming stimulus can include delivering noninvasive transcranial direct current stimulation and/or noninvasive transcranial magnetic stimulation to the brain. The first peripheral nerve effector and the second peripheral nerve effector can be both positioned below the knee of the patient and/or above the ankle of the patient. The first electrical stimulation signal can be the same as, or different from the second electrical stimulation signal. The first electrical stimulation signal has a first frequency, pulse width, amplitude, and/or other parameter different from a second parameter of the second electrical stimulation signal. The first frequency can be in some cases from about 5 Hz to about 30 Hz. The second frequency can be in some cases from about 10 Hz to about 20 Hz. Receiving an input relating to autonomic nervous system activity of the patient an include receiving data from a sensor that measures autonomic nervous system activity of the patient, such as heart rate variability of the patient. Heart rate variability data can be received from an optical sensor measuring blood flow characteristics and disposed proximate a vessel proximate a knee of the patient. Data can also be received from a sensor that measures galvanic skin response of the patient. The input could also be urinary symptoms of the patient, and/or nocturia episodes of the patient.

Also disclosed in some embodiments is a wearable device for dual transcutaneous stimulation of a first afferent lower extremity nerve and a second afferent lower extremity nerve and for treating urinary symptoms in a patient. The device could include any of the following: a controller; a first peripheral nerve effector, comprising at least one stimulation electrode configured to be positioned to transcutaneously modulate the saphenous nerve; a second peripheral nerve effector, comprising at least one stimulation electrode configured to be positioned to transcutaneously modulate the tibial nerve; and at least one biomedical sensor or data input source configured to provide feedback information. The controller can include a processor and a memory for receiving the feedback information from the sensor that, when executed by the processor, cause the device to: adjust one or more parameters of a first electrical stimulus and a second electrical stimulus based at least in part on the feedback information; and/or deliver the first electrical stimulus to the first afferent lower extremity nerve through the first peripheral nerve effector and deliver the second electrical stimulus to the second afferent lower extremity nerve through the second peripheral nerve effector to reduce urinary symptoms by modifying a brain or spinal cord autonomic feedback loop relating to bladder function and balancing sympathetic nerve and parasympathetic nerve activity. The device could be, or in some cases not configured for implantation within the patient. The first electrical stimulus and the second electrical stimulus can both include burst stimulation, such as, for example, continuous, intermittent, and/or intermediate theta burst stimulation. The first peripheral nerve effector may not in some cases be physically connected to the second peripheral nerve effector. The first electrical stimulus could be stimulatory or inhibitory to the first afferent lower extremity peripheral nerve. In some cases, the first electrical stimulation signal is stimulatory to the first afferent lower extremity peripheral nerve, and the second electrical stimulatory signal is inhibitory to the second afferent lower extremity peripheral nerve. The device could be further configured to deliver a priming electrical nerve stimulus prior to delivering the first electrical stimulus, such as a non-theta burst stimulus. The device can also be further configured to alternate the first electrical nerve stimulation signal to the first afferent lower extremity peripheral nerve and the second peripheral nerve signal to the second afferent lower extremity peripheral nerve. The feedback information can in some cases be real-time feedback information. The first electrical stimulus can have a frequency of, for example, between about 5 Hz and about 30 Hz. The second electrical stimulus can have a frequency of, for example, between about 10 Hz and about 20 Hz. The feedback information could include any number of: autonomic nervous system activity of the patient; heart rate variability; nocturia events of the patient; and/or information relating to patient sleep state.

In some embodiments, disclosed herein is a method of treating urinary symptoms in a patient with dual transcutaneous stimulation of a first afferent lower extremity nerve and a second afferent lower extremity nerve. The method can include providing a wearable device including any number of elements disclosed herein; positioning the first peripheral nerve effector on the patient's skin to stimulate the first afferent lower extremity nerve of the patient; positioning the second peripheral nerve effector on the patient's skin to stimulate the second afferent lower extremity nerve of the patient; delivering a first electrical nerve stimulation signal transcutaneously to the saphenous nerve through the first peripheral nerve effector; delivering a second electrical nerve stimulation signal transcutaneously to the tibial nerve through the second peripheral nerve effector; receiving an input relating to autonomic nervous system activity of the patient; and modifying at least one brain or spinal cord autonomic feedback loop relating to bladder function based on the input to balance parasympathetic and sympathetic nervous system activity of the patient. In some embodiments, the method does not utilize any implantable components, and only involves transcutaneous stimulation. The first electrical stimulation signal and the second electrical stimulation signal can include burst electrical stimulation signals, wherein the burst electrical stimulation signals induce neural plasticity. In some embodiments, use of a device including any number of features disclosed herein can modify at least one brain or spinal cord autonomic feedback loop relating to bladder function based on the input to balance parasympathetic and sympathetic nervous system activity of the patient and induce neural plasticity in the patient.

Also disclosed herein is a wearable system for treating urinary symptoms in a patient. The device can include any number of: a first controller and a second controller configured to operably communicate with each other, the first controller and the second controller not in physical communication with each other; a first peripheral nerve effector, comprising at least one stimulation electrode configured to be positioned to transcutaneously modulate a first afferent nerve pathway associated with bladder function; a second peripheral nerve effector, comprising at least one stimulation electrode configured to be positioned to transcutaneously modulate a second afferent nerve pathway associated with bladder function; and at least one input source configured to provide feedback information. The first controller and the second controller each can include a processor and a memory for receiving the real-time feedback information from the input source that, when executed by the processor, cause the device to: adjust one or more parameters of a first electrical stimulus based at least in part on the feedback information; adjust one or more parameters of a second electrical stimulus based at least in part on the feedback information independent from the first electrical stimulus; deliver the first electrical stimulus to a first afferent nerve pathway through the first peripheral nerve effector to reduce urinary symptoms by modifying a first brain or spinal cord autonomic feedback loop relating to bladder function; and/or deliver the second electrical stimulus to a second afferent nerve pathway through the second peripheral nerve effector to reduce urinary symptoms by modifying a second brain or spinal cord autonomic feedback loop relating to bladder function. Adjusting the one or more parameters of the first electrical stimulus and the second electrical stimulus can contribute to balancing sympathetic and parasympathetic nervous system activity. The first electrical stimulus and the second electrical stimulus both can include burst stimulation.

In some embodiments, also disclosed herein is a method of treating urinary symptoms in a patient with dual transcutaneous stimulation of a first afferent lower extremity nerve and a second afferent lower extremity nerve. The method can include any number of: positioning a first peripheral nerve effector on the patient's skin to stimulate the first afferent lower extremity nerve of the patient; positioning a second peripheral nerve effector on the patient's skin to stimulate the second afferent lower extremity nerve of the patient; delivering a first electrical nerve stimulation signal transcutaneously to the first afferent lower extremity nerve through the first peripheral nerve effector; delivering a second electrical nerve stimulation signal transcutaneously to the second afferent lower extremity nerve through the second peripheral nerve effector; receiving an input relating to autonomic nervous system activity of the patient, wherein the input comprises both heart rate variability and electrodermal activity of the patient; and modifying at least one brain or spinal cord autonomic feedback loop relating to bladder function based on the input to balance parasympathetic and sympathetic nervous system activity of the patient. The heart rate variability and electrodermal activity inputs can be received from a wrist-worn device on the patient, a device on the patient's lower extremity, from an ear-worn device, or other site. The first electrical stimulus and the second electrical stimulus can both include burst stimulation, such as, for example, continuous, intermittent, and/or intermediate theta burst stimulation. The first peripheral nerve effector may not in some cases be physically connected to the second peripheral nerve effector. The first electrical stimulus could be stimulatory or inhibitory to the first afferent lower extremity peripheral nerve. In some cases, the first electrical stimulation signal is stimulatory to the first afferent lower extremity peripheral nerve, and the second electrical stimulatory signal is inhibitory to the second afferent lower extremity peripheral nerve. The device could be further configured to deliver a priming electrical nerve stimulus prior to delivering the first electrical stimulus, such as a non-theta burst stimulus. The device can also be further configured to alternate the first electrical nerve stimulation signal to the first afferent lower extremity peripheral nerve and the second peripheral nerve signal to the second afferent lower extremity peripheral nerve. The feedback information can in some cases be real-time feedback information. The first electrical stimulus can have a frequency of, for example, between about 5 Hz and about 30 Hz. The second electrical stimulus can have a frequency of, for example, between about 10 Hz and about 20 Hz. The feedback information could include any number of: autonomic nervous system activity of the patient; heart rate variability; nocturia events of the patient; and/or information relating to patient sleep state.

In some embodiments, also disclosed herein is a wearable device for dual transcutaneous stimulation of a first afferent lower extremity nerve and a second afferent lower extremity nerve and for treating urinary symptoms in a patient. The device can include a controller; a first peripheral nerve effector that includes at least one stimulation electrode configured to be positioned to transcutaneously modulate the first afferent lower extremity nerve; a second peripheral nerve effector, comprising at least one stimulation electrode configured to be positioned to transcutaneously modulate the second afferent lower extremity nerve; and at least one biomedical sensor or data input source configured to provide feedback information, the feedback information comprising autonomic nervous system activity comprising both heart rate variability information and electrodermal activity information of the patient. The controller can include a processor and a memory for receiving the feedback information from the sensor that, when executed by the processor, cause the device to adjust one or more parameters of a first electrical stimulus and a second electrical stimulus based at least in part on the feedback information; and/or deliver the first electrical stimulus to the first afferent lower extremity nerve through the first peripheral nerve effector and deliver the second electrical stimulus to the second afferent lower extremity nerve through the second peripheral nerve effector to reduce urinary symptoms by modifying a brain or spinal cord autonomic feedback loop relating to bladder function and balancing sympathetic nerve and parasympathetic nerve activity. The device can be configured for implantation within the patient. The first electrical stimulus and the second electrical stimulus can both include burst stimulation, such as, for example, continuous, intermittent, and/or intermediate theta burst stimulation. The first peripheral nerve effector may not in some cases be physically connected to the second peripheral nerve effector. The first electrical stimulus could be stimulatory or inhibitory to the first afferent lower extremity peripheral nerve. In some cases, the first electrical stimulation signal is stimulatory to the first afferent lower extremity peripheral nerve, and the second electrical stimulatory signal is inhibitory to the second afferent lower extremity peripheral nerve. The device could be farther configured to deliver a priming electrical nerve stimulus prior to delivering the first electrical stimulus, such as a non-theta burst stimulus. The device can also be further configured to alternate the first electrical nerve stimulation signal to the first afferent lower extremity peripheral nerve and the second peripheral nerve signal to the second afferent lower extremity peripheral nerve. The feedback information can in some cases be real-time feedback information. The first electrical stimulus can have a frequency of, for example, between about 5 Hz and about 30 Hz. The second electrical stimulus can have a frequency of, for example, between about 10 Hz and about 20 Hz. The feedback information could include any number of: autonomic nervous system activity of the patient; heart rate variability; nocturia events of the patient; and/or information relating to patient sleep state.

Also disclosed herein in some embodiments is a method of treating urinary symptoms in a patient with dual stimulation of a first afferent lower extremity nerve and a second afferent lower extremity nerve. The method can include any of the following: positioning a first peripheral nerve effector on the patient to stimulate the first afferent lower extremity nerve of the patient; positioning a second peripheral nerve effector on the patient to stimulate the second afferent lower extremity nerve of the patient; delivering a first electrical nerve stimulation signal to the first afferent lower extremity nerve through the first peripheral nerve effector; delivering a second electrical nerve stimulation signal to the second afferent lower extremity nerve through the second peripheral nerve effector; receiving an input relating to autonomic nervous system activity of the patient; and modifying at least one brain or spinal cord autonomic feedback loop relating to bladder function based on the input to balance parasympathetic and sympathetic nervous system activity of the patient. In some embodiments, the first electrical stimulation signal and the second electrical stimulation signal comprise burst electrical stimulation signals. The burst electrical stimulation signals can induce neural plasticity.

Also disclosed herein in some embodiments of a method for treating overactive bladder. The method can include any of the following: assessing at least one of sympathetic and parasympathetic activity of a subject and determining the presence of sympathetic or parasympathetic overactivity in the subject; stimulating a first lower extremity afferent nerve sufficient to have a therapeutic effect on overactive bladder only if abnormal sympathetic activity is present; and stimulating a second lower extremity afferent nerve sufficient to have a therapeutic effect on overactive bladder only if abnormal parasympathetic activity is present. Stimulating can include only electrical transcutaneous stimulation in some cases. Stimulating can involve exciting and/or inhibiting nerve activity of the first lower extremity afferent nerve or the second lower extremity afferent nerve. In some embodiments, the second lower extremity afferent nerve can be on a different (e.g., contralateral) extremity with respect to the first lower extremity afferent nerve. Stimulating can involve exciting nerve activity of the first lower extremity afferent nerve or the second lower extremity afferent nerve if one or both abnormal sympathetic activity and abnormal parasympathetic activity are present. Assessing at least one of sympathetic and parasympathetic activity of a subject can include measuring HRV in the subject, such as via a wrist-worn or other device. The method can also include measuring heart rate, and/or electrodermal activity in the subject. HRV can be measured during a bladder filling procedure, e.g., urodynamic cystography, which can be performed prior to or after the initial stimulation.

Also disclosed herein is a method for treating overactive bladder, including any number of electrically stimulating a first nerve associated with bladder function; assessing at least one of sympathetic and parasympathetic activity of a subject and determining the presence or absence of sympathetic or parasympathetic overactivity in the subject; assessing symptomatology of overactive bladder; and/or adjusting the electrical stimulation based upon assessing the at least one of sympathetic and parasympathetic activity and the symptomatology of overactive bladder. Adjusting the electrical stimulation can include identifying sympathetic or parasympathetic overactivity in the patient; discontinuing electrical stimulation of the first nerve associated with bladder function; and/or initiating electrical stimulation of a second nerve associated with bladder function. The first and/or second nerve could be, for example, the saphenous, tibial, peroneal, or sacral nerves. Stimulating can include, for example, only electrical transcutaneous stimulation. Assessing at least one of sympathetic and parasympathetic activity of a subject can include measuring HRV in the subject, such as via a wrist-worn device. The method can also include measuring heart rate and/or electrodermal activity in the subject. HRV can be measured during a bladder filling procedure, e.g., urodynamic cystography, which can be performed prior to or after the initial stimulation.

Disclosed herein is a method of treating urinary symptoms in a patient with transcutaneous stimulation of an afferent lower extremity nerve. The method can include, for example, positioning a first peripheral nerve effector on the patient's skin to stimulate the afferent lower extremity nerve of the patient; delivering a first electrical nerve stimulation signal transcutaneously to the afferent lower extremity nerve through the first peripheral nerve effector; receiving an input relating to autonomic nervous system activity of the patient; and modifying at least one brain or spinal cord autonomic feedback loop relating to bladder function based on the input to balance parasympathetic and sympathetic nervous system activity of the patient. The method can in some cases not utilize any implantable components, and only involves transcutaneous stimulation. The first electrical stimulation signal can include burst electrical stimulation signals that can induce neural plasticity.

The stimulation can be continuous, intermittent, or intermediate theta burst stimulation in some embodiments. The device can also be configured to deliver a priming electrical nerve stimulation signal prior to the first electrical stimulation signal, which can be a non-theta burst stimulation signal. The device can further include a second peripheral nerve effector, including at least one stimulation electrode configured to be positioned to transcutaneously modulate a second afferent peripheral nerve, and is configured to deliver a second electrical nerve stimulation signal transcutaneously to the afferent peripheral nerve of the user. The signal can include, for example, electrical theta burst stimulation. Also disclosed herein is a method for treating overactive bladder, that can include assessing at least one of sympathetic and parasympathetic activity of a subject and determining the presence of sympathetic or parasympathetic overactivity in the subject; and stimulating the saphenous nerve sufficient to have a therapeutic effect on overactive bladder if abnormal sympathetic activity is present; and/or stimulating the tibial nerve sufficient to have a therapeutic effect on overactive bladder if abnormal parasympathetic activity is present. In some embodiments, stimulating comprises only electrical transcutaneous stimulation. The stimulation can include inhibiting or exciting nerve activity of either or both of the saphenous nerve, tibial nerve, or other target nerves. Sympathetic and parasympathetic activity of a subject can include measuring HRV, such as via a wrist-worn device. Other parameters such as heart rate and electrodermal activity can be measured in addition or alternatively. HRV can be measured during a bladder filling procedure, such as urodynamic cystography, either prior to and/or after the initial stimulation. Also disclosed herein in some embodiments is a method for treating overactive bladder, that can include electrically stimulating a first nerve associated with bladder function; assessing at least one of sympathetic and parasympathetic activity of a subject and determining the presence or absence of sympathetic or parasympathetic overactivity in the subject; assessing symptomatology of overactive bladder; and adjusting the electrical stimulation based upon assessing the at least one of sympathetic and parasympathetic activity and the symptomatology of overactive bladder. Adjusting the electrical stimulation can include, for example, identifying sympathetic or parasympathetic overactivity in the patient, and adjusting the frequency of stimulation of the first nerve; and/or discontinuing electrical stimulation of the first nerve associated with bladder function; and initiating electrical stimulation of a second nerve associated with bladder function. In some embodiments, the method can also include delivering noninvasive transcranial direct current stimulation or noninvasive transcranial magnetic stimulation to the brain; and synchronizing the transcranial stimulation with the first electrical nerve stimulation signal to the first afferent lower extremity peripheral nerve, and/or delivering a priming stimulus prior to the first electrical stimulation signal, including delivering noninvasive transcranial direct current stimulation or noninvasive transcranial magnetic stimulation to the brain. The first peripheral nerve effector can be positioned below the knee of the patient, but above the ankle of the patient. Receiving an input relating to autonomic nervous system activity of the patient can include, for example, receiving data from a sensor that measures autonomic nervous system activity, heart rate variability, activity (e.g., number of steps taken and/or distance walked) and/or galvanic skin response of the patient. Heart rate variability data can be received from an optical sensor measuring blood flow characteristics and disposed proximate a vessel proximate a knee of the patient. An input can also include data relating to urinary symptoms, activity, and/or nocturia episodes of the patient.

In some embodiments, disclosed herein is a wearable device for transcutaneous stimulation of a first afferent lower extremity nerve for treating urinary symptoms in a patient. The device can include a controller; a first peripheral nerve effector, comprising at least one stimulation electrode configured to be positioned to transcutaneously modulate a first afferent lower extremity nerve; and a stimulator configured to deliver a first electrical stimulus to the first afferent lower extremity nerve through the first peripheral nerve effector to reduce urinary symptoms by modifying a brain or spinal cord autonomic feedback loop relating to bladder function and balancing sympathetic nerve and parasympathetic nerve activity. The device is in some embodiments not configured for implantation within the patient. The first electrical stimulus can include burst stimulation, such as alpha, delta, or theta burst stimulation, e.g., intermittent, intermediate, and/or continuous theta burst stimulation. The device can also include one or more biomedical sensors or data input sources configured to provide feedback information. The controller can include a processor and a memory for receiving the feedback information from the sensor that, when executed by the processor, cause the device to adjust one or more parameters of the first electrical stimulus based at least in part on the feedback information. The first electrical stimulation can include a stimulation parameter modulated within a range from a first lower predetermined value to a second higher predetermined value. The stimulation parameter can include one or more of, for example, pulse width, frequency, and amplitude. The first electrical stimulus can be stimulatory or inhibitory to the first afferent lower extremity peripheral nerve. The device can be further configured to deliver a priming electrical nerve stimulus prior to delivering the first electrical stimulus, such as a non-theta burst stimulus. The feedback information can include real-time feedback information. The first or second electrical stimulus could have, for example, a frequency of between about 5 Hz and about 30 Hz. The feedback information could include autonomic nervous system activity, heart rate variability, nocturia events of the patient, and/or patient sleep state.

In some embodiments, disclosed herein is a wearable system for treating urinary symptoms in a patient. The device can include any number of a first controller and a second controller configured to operably communicate with each other, the first controller and the second controller not in physical communication with each other; a first peripheral nerve effector, comprising at least one stimulation electrode configured to be positioned to transcutaneously modulate a first afferent nerve pathway associated with bladder function; a second peripheral nerve effector, comprising at least one stimulation electrode configured to be positioned to transcutaneously modulate the first afferent nerve pathway associated with bladder function; at least one input source configured to provide feedback information; and/or a stimulator configured to deliver the first electrical stimulus to a first afferent nerve pathway through the first peripheral nerve effector to reduce urinary symptoms by modifying a first brain or spinal cord autonomic feedback loop relating to bladder function; and deliver the second electrical stimulus to the first afferent nerve pathway through the second peripheral nerve effector to reduce urinary symptoms by modifying the first brain or spinal cord autonomic feedback loop relating to bladder function. Adjusting the one or more parameters of the first electrical stimulus and the second electrical stimulus can contribute to balancing sympathetic and parasympathetic nervous system activity. The first electrical stimulus and the second electrical stimulus can both include burst stimulation. The first controller and the second controller can each include a processor and a memory for receiving the real-time feedback information from the input source that, when executed by the processor, cause the device to adjust one or more parameters of the first electrical stimulus based at least in part on the feedback information and/or adjust one or more parameters of the second electrical stimulus based at least in part on the feedback information independent from the first electrical stimulus. The input source can include, for example, at least one biomedical sensor. Feedback information can include, for example, autonomic nervous system activity of the patient, heart rate variability information of the patient, nocturia events of the patient, patient sleep state, or patient eye blink reflex.

BRIEF DESCRIPTION OF THE DRAWINGS

FIGS. 5A-5C illustrate non-limiting embodiments of potential electrode placement locations for nerve stimulation.

FIGS. 6-7 illustrate views of stimulation devices with sticky electrodes, according to some embodiments of the invention.

FIGS. 11A-11E and 12A illustrate that systems and methods of peripheral nerve stimulation can be provided that target one, two, or more individual nerves.

FIGS. 17A-17F illustrate clinical data relating to tibial nerve stimulation, according to some embodiments of the invention.

FIG. 18B illustrates two stimulation sessions with a 10 minute interval between sessions; FIG. 18C shows two stimulation sessions with a 30 minute interval between sessions.

DETAILED DESCRIPTION

Figure 1:
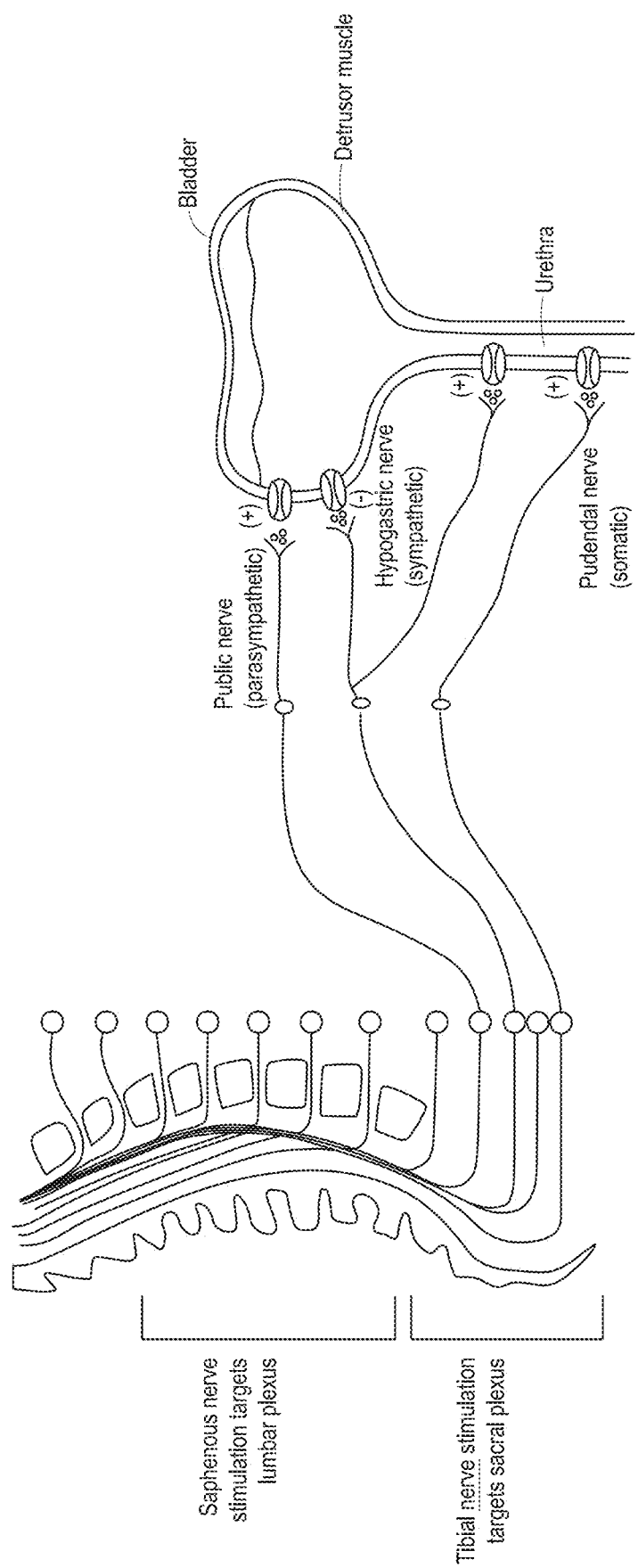
FIG. 1 illustrates non-limiting structures and pathways associated with bladder function.

As used herein, the terms "stimulating" and "stimulator" generally refer to delivery of a signal, stimulus, or impulse to neural tissue of the targeted region. The effect of such stimulation on neuronal activity is termed "modulation;" however, for simplicity, the terms "stimulating" and "modulating," and variants thereof, are sometimes used interchangeably herein. The effect of delivery of the signal to the neural tissue may be excitatory or inhibitory and may potentiate acute and/or long-term changes in neuronal activity. For example, the effect of "stimulating" or "modulating" a neural tissue may comprise one or more of the following effects: (a) depolarizing the neurons such that the neurons fire action potentials, (b) hyperpolarizing the neurons to inhibit action potentials and optionally anode break excitation following termination of a hyperpolarizing event, (c) depleting neurons ion stores to inhibit firing action potentials, (d) altering with sensory input, including proprioception, (e) influencing muscle contractions, (f) affecting changes in neurotransmitter release or uptake, or (g) inhibiting firing. "Sensory input" refers to receptors, nerves, and/or neurons that transmit sensory information to other nerves, the spinal cord, brain, or central nervous system. "Proprioception" refers to one's sensation of the relative position of one's own body parts or the effort being employed to move one's body part. Proprioception may otherwise be referred to as somatosensory, kinesthetic, or haptic sensation. A "proprioceptor" is a receptor providing proprioceptive information to the nervous system and includes stretch receptors in muscles, joints, ligaments, and tendons as well as receptors for pressure, temperature, light and sound. An "effector" is the mechanism by which the device modulates the target nerve. For example, the "effector" may be electrical stimulation of the nerve or mechanical stimulation of proprioceptors.

"Electrical stimulation" refers to the application of electrical signals to the soft-tissue and nerves of the targeted area. The "cloud" refers to a network of computers communication using real-time protocols such as the internet to analyze, display and interact with data across distributed devices.

Some forms of therapy for control of urinary symptoms include electrical neuromodulation, including transcutaneous and/or percutaneous peripheral nerve stimulation and/or implantable pudendal or sacral nerve stimulation. Neuromodulation of the urinary system can be highly effective in the control of lower urinary tract symptoms. Modulation of urinary reflexes can be accomplished in some embodiments by stimulation of lumbosacral afferent pathways. Sacral neuromodulation can include surgical placement of an implant at the level of the S3 sacral foramina and can be highly effective and durable but requires an invasive procedure. The stimulation can be performed continuously and in an open-loop. Sacral stimulation can lead to modulation of the micturition reflex at the spinal or supraspinal level. Although sacral nerve stimulation is considered relatively long-lasting, it is invasive and side effects include buttock, lower extremity or pelvic pain, lead site infection, and negative changes in urinary, bowel or sexual function. Device related complications include battery failure, lead migration, or loss of efficacy necessitating revision or explanation of the device.

Modulation of bladder dysfunction can also be achieved in some cases using intermittent tibial nerve stimulation. The acute effects of stimulation can include improvements in cystometry measures, including bladder capacity. Stimulation can be performed, for example, weekly with a percutaneous needle electrode in 30 minute sessions. As the stimulation is not continuous, there can be a carry-over effect. The effects of percutaneous tibial nerve stimulation can be maintained after, for example, 12 weeks, but a continued schedule of sessions can be required thereafter every month to maintain efficacy. Stimulation of the tibial nerve can lead to spinal root L4-S3 stimulation inhibiting bladder activity although it is unclear whether spinal reflex or brain networks are responsible for the effects. The presence of a carry-over effect after the period of stimulation suggests a plasticity mechanism either at the level of the spine or brain.

Transcutaneous stimulation of one, two, or more target nerves of interest, e.g., the saphenous nerve, and/or or tibial nerve stimulation can control urinary incontinence symptoms with varying levels of success. However, in some embodiments, transcutaneous stimulation can be preferred. The feasibility of home-based stimulation has been limited by device form factor and limited programming flexibility of current devices.

In some embodiments, more continuous stimulation at the level of the tibial and/or saphenous nerve can potentially improve the efficacy of peripheral nerve stimulation for conditions such as, for example, urinary incontinence. An implanted percutaneous tibial nerve stimulator can be efficacious and safe. Some embodiments can use frequencies of, for example, between about 1 kHz and about 100 kHz, 1 Hz and about 100 Hz, between about 1 Hz and about 50 Hz, between about 5 Hz and about 30 Hz, or between about 10 Hz and about 20 Hz stimulation for a specified period of time, such as about, at least about, or no more than about 20, 30, 40, 50 or 60 minutes at a sensory or sub-sensory threshold or below motor contraction threshold that is tolerable to the patient. Varying the regularity of stimulation and the frequency of the stimulation waveform may improve tolerance or efficacy in some cases. An increased frequency of stimulation may be more effective but could require a more chronic at-home portable system to provide continuous transcutaneous stimulation throughout the day.

Stimulating at intensities below the sensory threshold or with high frequencies (e.g., between about 1 kHz to about 100 kHz) can avoid the discomfort (tingling, numbness, pain) that can be associated with peripheral nerve stimulation. Because the exact electrode position, size and surface contact have a large effect on the stimulation level and the anatomical structures that receive the stimulation, the sensory threshold may need to be calibrated for each patient and even for each session. This calibration may be done by the user manually setting the stimulation parameters or otherwise indicating their sensory threshold. Another possible embodiment is for the device to automatically sweep through a range of stimulation parameters and the patient chooses the most comfortable set of parameter values. Another possible embodiment is for the patient to choose from among a set of previously chosen parameter values that provided effective and comfortable stimulation.

In some embodiments, disclosed herein are peripheral nerve stimulators to improve conditions including but not limited to urinary dysfunction. The stimulation can target one, two, three, or more nerves associated with bladder function. The nerves can include, for example, the tibial nerve or posterior tibial nerve, which can branch into the medial and lateral plantar nerve branches, and the calcaneal nerves. The saphenous nerve is the cutaneous branch of the femoral nerve. Other nerves include, for example, the pudendal nerve, pelvic nerve, dorsal genital nerve, external anal sphincter nerve, and the dorsal genital nerve, for example. In some embodiments, the tibial (e.g., posterior tibial) nerve can be stimulated transcutaneously in a manner similar to percutaneous tibial nerve stimulation but noninvasively and in a more prolonged manner. In some embodiments, systems and methods include only transcutaneous elements without any implanted and/or percutaneous components. In some embodiments, the nerve(s) to be stimulated are lower extremity peripheral afferent nerves only, and are not spinal nerves.

Not to be limited by theory, voluntary control of the bladder can be mediated in large part by the autonomic nervous system (ANS). The ANS maintains a balance which can be important to the normal functioning of the body's organs. For instance, the hypogastric nerve (sympathetic) and pelvic nerve (parasympathetic) both carry information about bladder fullness to the brain, and also work together to enable the relaxation-contraction mechanism that controls micturition. FIG. 1 illustrates non-limiting structures and pathways associated with bladder function.

Activation of the pontine micturition center (PMC) results in parasympathetic activation of the bladder. This in turn contracts muscles in the bladder and relaxes muscles in the urethra. Micturition commands cease when CNS structures including the periaqueductal gray (PAG) receive signals that the bladder is no longer full.

Inappropriate activation and inhibition of the parasympathetic and sympathetic systems can result in a sense of bladder fullness, urgency, sensory discomfort, and/or involuntary voiding. Peripheral stimulation that affects the activity of autonomic nerves can be used to modulate or interrupt micturition reflex circuits to correct abnormal bladder functioning. This modulation can be achieved by, for example, stimulation of the saphenous nerve, tibial nerve, or a combination of the two. In some embodiments, systems and methods use stimulation schemes designed to dephase, override or obscure the abnormal networks. In some embodiments, systems and methods use stimulation schemes designed to restore balance of sympathetic and parasympathetic activity of the micturition reflex loop. Advantageously, certain embodiments utilize transcutaneous afferent stimulation of one, two, or more peripheral nerves to modulate a brain or spinal pathway associated with bladder function, and/or an organ or target remote from the site(s) of stimulation.

Generally, sympathetic fibers originate in the T11 to L2 segments of the spinal cord, while parasympathetic fibers originate in the S2 to S4 spinal segments. The sympathetic fibers travel through the hypogastric nerve and inferior mesenteric ganglia, while the parasympathetic fibers travel in the pelvic nerves and plexus. In some cases, effective frequency band for this parasympathetic modulation can be, for example, around the frequency band of 10 to 20 Hz, while the frequency band sympathetic modulation can be, in some cases, as high as 30 Hz or as low as 5 Hz. Not to be limited by theory, in some cases the higher frequencies may offer benefit in comfort while the lower frequencies may offer benefit in better preservation.

In some embodiments, systems and methods involve stimulation parameters including frequency and spatial selectivity on the surface of the distal limb to selectively modulate and balance the sympathetic and parasympathetic system.

Not to be limited by theory, stimulation of a first target nerve, such as the saphenous nerve can provide sympathetic modulation of the bladder circuit. Specifically, electrical stimulation tuned to excite large myelinated fibers in a target nerve, e.g., the saphenous nerve can provide somatic afferent input to the lumbar plexus, mediating the sympathetic input to the bladder circuitry via the hypogastric nerve. Sympathetic nerves relax the detrusor muscle of the bladder by releasing norepinephrine, activating the β adrenergic receptors, and contract the intrinsic urethral sphincter, by activating the α-adrenergic receptors. Relaxing the bladder and contracting the intrinsic sphincters can give comfort during the filling and storage phases of the bladder cycle. Stimulation of a second target nerve, e.g., the tibial nerve can provide parasympathetic modulation of the bladder circuit. Specifically, electrical stimulation tuned to excite large myelinated fibers in the tibial nerve provides somatic afferent input to sacral plexus, the sacral micturition center, mediating parasympathetic input to the bladder circuitry via the pelvic nerves via release of cholinergic transmitters. There may also be input from the somatic efferents of the pelvic floor to the external urethral sphincter and modulates the afferent sensation of bladder fullness. Due to widely connected and circuit-based mechanisms of these circuits, all mechanisms described above can in some embodiments modulate the central cortical and pontine micturition centers which coordinate and time signals.

The system may run on a selection of pre-specified programs that vary stimulation parameters and target one or more nerves individually or in combination to improve symptoms of overactive bladder in a specific patient, e.g. whether their challenge is primarily daytime urinary urgency, nighttime waking (nocturia), or incontinence. Alternatively, the system may be closed loop on a number of parameters including: the subject's symptomatic history, including night waking events, or manually entered urination indicated on board the device or a secondary device; direct detection of sympathetic and parasympathetic tone in the bladder or general circuitry, including HRV and galvanic skin response; and/or closed-loop based on previous usage of a device.

In some embodiments, nerve stimulation can be synergistically combined with one, two, or more pharmacologic therapies for overactive bladder, including but not limited to an anti-cholinergic (e.g., oxybutynin, tolterodine, trospium, darifenacin, solifenancin, and/or fesoterodine), a beta-3 adrenergic (e.g., mirabegron), an anti-spasmodic (e.g., flavoxate), and/or an anti-depressant (e.g., a tricyclic antidepressant such as desipramine or imipramine), a hormone (such as an estrogen and/or progesterone), or botulinum toxin.

Figure 1A:
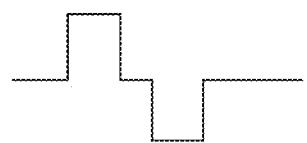
FIGS. 1A and 1B illustrate examples of stimulation waveforms, according to some embodiments of the invention.
Figure 1B:
Figure 1C:
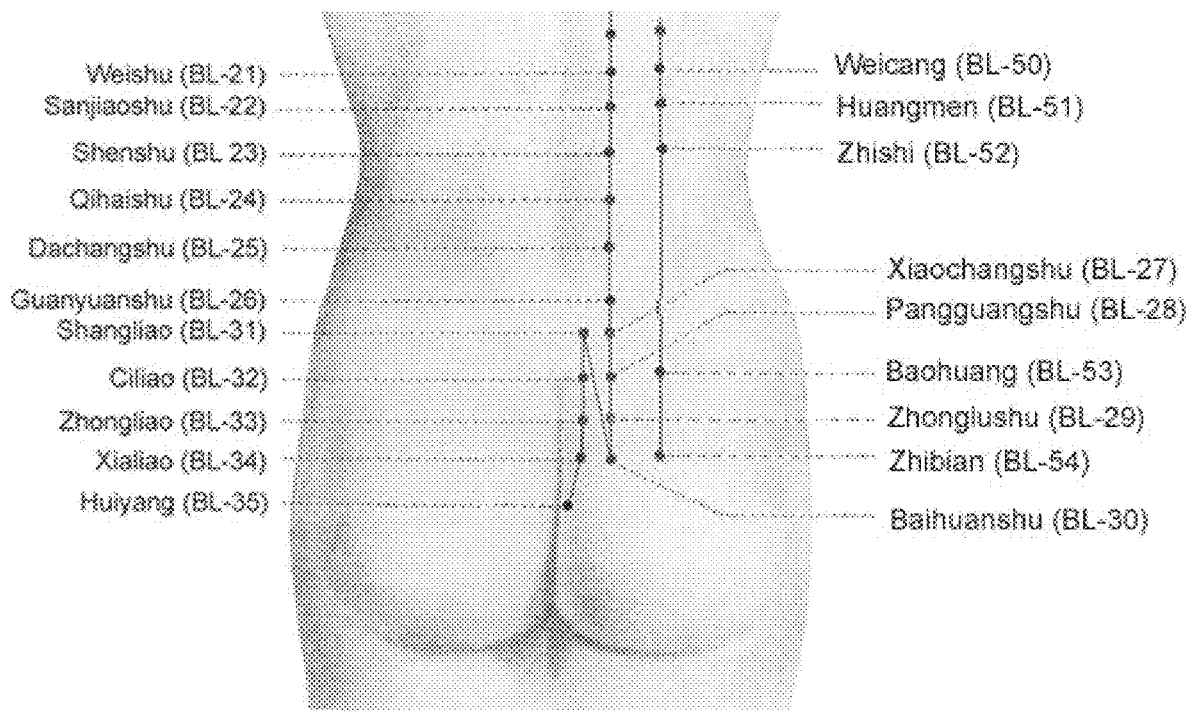
FIGS. 1C-1G illustrate non-limiting examples of potential acupuncture points that can be stimulated, in accordance with some embodiments of the invention.
Figure 1D:
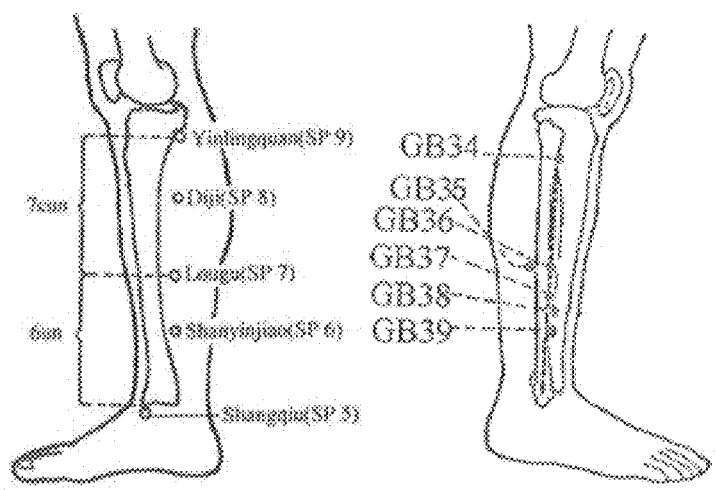
Figure 1E:
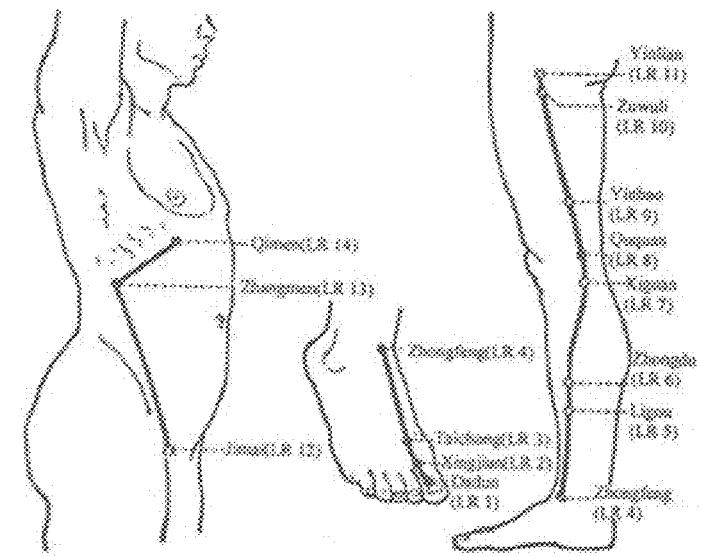
Figure 1F:
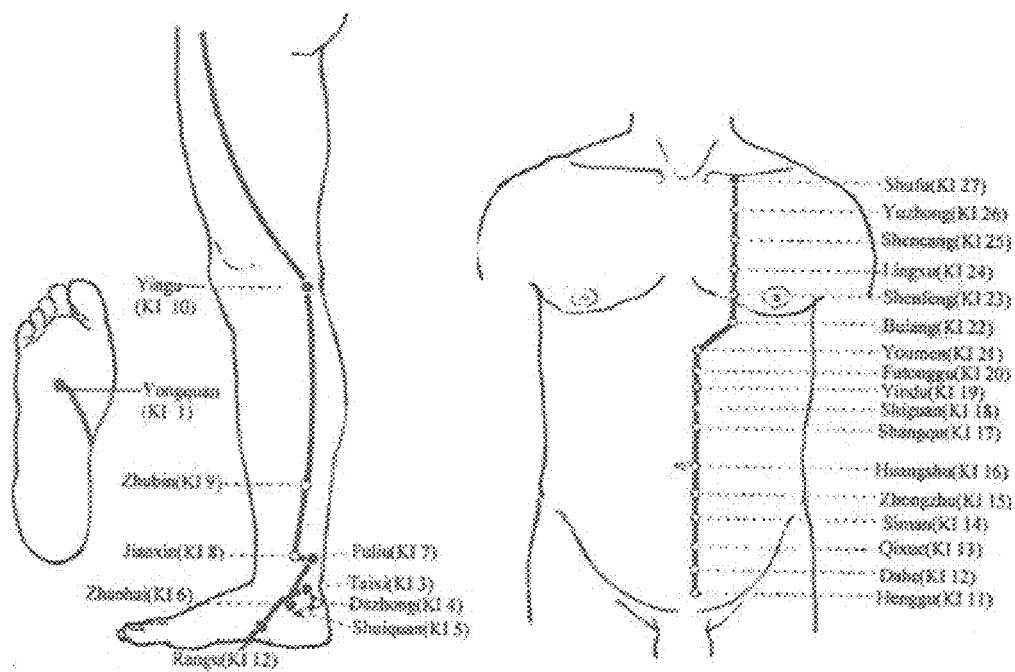
Figure 1G:
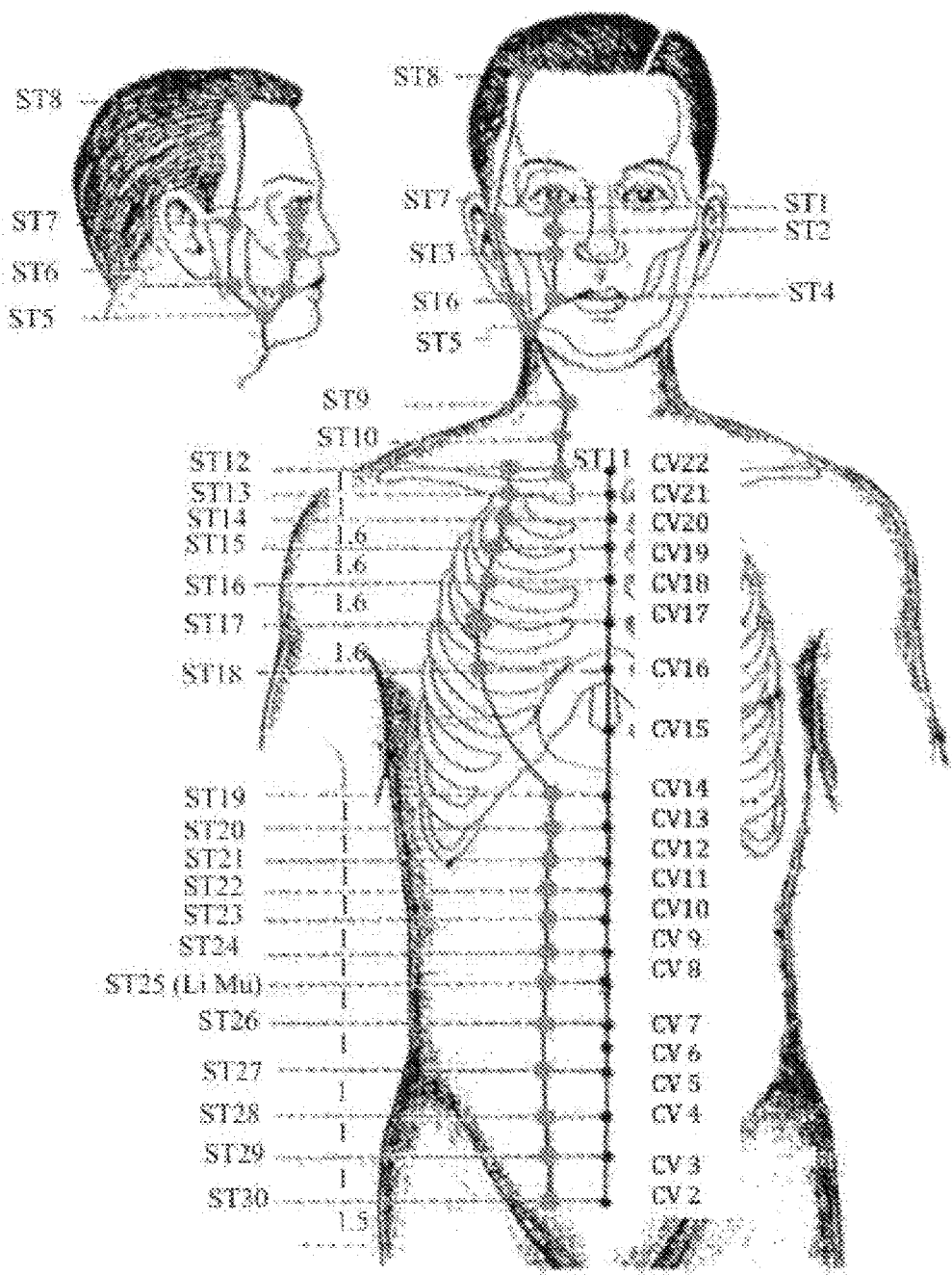

Use of chronic, noninvasive stimulation can involve certain waveform characteristics to excite sensory neurons in a comfortable manner. The frequency of stimulation used can be, for example, within the between about 1 Hz and about 500 Hz range (such as, for example, between about 5 Hz and about 30 Hz, such as between about 10 Hz and about 20 Hz) or between about 1 kHz and about 100 kHz to preferentially affect the proper targets. In some embodiments, the waveforms can be biphasic rectangular or balanced in charge in order to minimize irritation to the skin, such as illustrated schematically in FIG. 1A. In some embodiments, waveforms could also be asymmetric, especially in the case to stimulate one, two, three, or more nerves as described in, for example, PCT Pub. No. WO 2018/009680 published Jan. 11, 2018, which is incorporated by reference in its entirety. In some embodiments, waveform shapes and rising edges can be altered in order to increase patient comfort and tolerability to the treatment. In some embodiments, the waveforms can include higher frequency sine waves carried inside the rectangular signal as illustrated in FIG. 1B. An interval between the opposite-going waveforms can be adjusted to a value that allows for charge balance, while allowing the first waveform's excitatory effects to not be immediately negated by the second waveform, but balancing the charge at the interface to reduce skin irritation and improve comfort. In some cases, spacing between 0 microseconds to 300 microseconds has been effective. The waveform amplitude can be adjusted so that it is perceptible, above a minimum sensation threshold, but not intolerable to the patient.

In some embodiments, the effector can be excitatory to the nerve. In other embodiments, the effector can be inhibitory to the nerve. In some embodiments, the system can be used to excite the nerve during some portions of the treatment and inhibit the nerve during other portions of the treatment.

In some embodiments, waveforms including those described herein can be modified over time in order to minimize certain effects, such as habituation. One way of decreasing habituation is to modify the frequency, pulse width, amplitude, or burst pattern of the stimulation. For instance, randomizing or pseudo-randomizing parameters such as, for example, the frequency or pulse width can reduce habituation. Using a Gaussian distribution for randomization can be effective in some cases, and used in such waveforms as stochastic waveforms. Another way of reducing habituation is to the lower the frequency below a certain threshold, such as, for example, no more than about 60 Hz, 55 Hz, 50 Hz, 45 Hz, or 40 Hz, in which humans tend not to habituate.

Varying other parameters such as amplitude can be a way to improve waveform comfort. For example, the amplitude of the stimulation can be adjusted based on the threshold necessary to produce strong sensory perception and paresthesia without eliciting motor contraction. Excitation of muscles can lead to unpleasant cramping sensations in some embodiments. This amplitude could also be modulated throughout a session to be the appropriate, comfortable value depending a person's position or motion.

The stimulation waveforms described herein can be applied continuously to target nerves such as the tibial and/or saphenous nerves, for example, or can be provided in a manner that is adaptive in applying stimulation of various durations or by adjusting properties of the stimulation waveform, including but not limited to amplitude, frequency, and pulse width, in response to different inputs in the system. In some embodiments, the system could include closed loop control, using one or more signals measured by the device or feedback input into the device by the patient or physician to modulate the stimulation to improve efficacy. The signals or input could include, for example, any number of the following: sensors on-board the device or connected in the digital ecosystem; evaluation of autonomic function, reflex loop integrity, or excitability using heart rate variability, measuring muscle sympathetic nerve activity (MSNA), and/or measuring h-reflex by sending a stimulation signal and measure response with EMG. In some embodiments, the signals or input can also include sleep sensor sets, including but not limited to accelerometers, gyroscopes, infrared based motion sensors, and/or pressure sensors under a mattress, to measure night time motion as a measure of nocturia events. For example, patients may wear a stimulator while sleeping and therapy can be triggered by night time restlessness, which is an indicator of an upcoming nocturia event. A motion sensor set (e.g., accelerometer, IR based motion sensor, etc.) can measure rapid back and forth movement of legs typically seen when someone has a sense of urgency. An EEG headband could be used to measure different sleep states. Patient and/or physician input can provide feedback on the effectiveness of and/or satisfaction with the therapy into the device or into another connected device. Also, usage of the stimulation device can be tracked; and specific stimulation programs (e.g., a specified set of stimulation parameters) can be changed based on symptoms presented by the patient or outcomes of the therapy.

In some embodiments, a stimulator can be part of a system with sensors to assess the state of sleep and modulate stimulation based on the wearer's sleep state. Sensors could include motion sensors (e.g., body worn accelerometers and gyroscopes, or wireless motion tracking via video or infrared), temperature sensors to measure body temperature, pressure sensor under the mattress to measure movement, heart rate sensors to measure HRV, other sensors to measure sympathetic and parasympathetic activity, and/or EEG sensors to measure brain activity to assess the wearer's sleep state. For example, if nocturia events occur during slow wave sleep when parasympathetic activity can be elevated, stimulation parameters are modulated to affect parasympathetic activity, and vice-versa for sympathetic activity.

In some embodiments, a first stimulation frequency can be provided for short term benefit, and a second stimulation frequency different (e.g., higher or lower) from the first stimulation frequency can be provided for long-term benefit. For example, 10 Hz stimulation can provide a short term benefit and 20 Hz stimulation can provide a long term benefit in some cases. As one example, 10 Hz stimulation can be provided in an initial period with the therapy (e.g., 3 weeks) for acute therapy, then 20 Hz stimulation can be provided for long term maintenance or condition therapy, or vice versa depending on the desired clinical result. In some embodiments, particular sympathetic and/or parasympathetic nervous system targets and circuits can be specifically targeted to modulate upward or downward sympathetic and/or parasympathetic nervous system activity depending on the patient's underlying autonomic nervous system activity. Utilization of data and/or sensors directly or indirectly measuring sympathetic and/or parasympathetic nervous system activity as disclosed, for example, elsewhere herein can be utilized as closed loop feedback inputs into a hardware and/or software controller to modify stimulation parameters, including on a real-time basis.

In some embodiments, the therapy (e.g., stimulation) can be applied for about, at least about, or no more than about 5 minutes, 10 minutes, 15 minutes, 30 minutes, 45 minutes, 1 hour, 2 hours, 3 hours, 4 hours, 5 hours, 6 hours, or more a day. In some embodiments, the patient is treated nocturnally, such as during sleep, and/or during waking hours. The treatment can be repeated 1, 2, 3, 4, 5, or more times daily or weekly, every other day, every third day, weekly, or other interval depending on the desired clinical result.

In some embodiments, the responsiveness could be dependent on different times of day. For instance, the patient or physician (or algorithm) could pre-schedule different episodic treatment sessions throughout the day and the device could provide treatment stimulation at those different times of day. In one example, treatments are applied at regular or irregular intervals during the day at a frequency related to the typical amount of voiding. In the treatment of nocturia, stimulation could be timed to periodic intervals during a persons sleep. In some embodiments, stimulation schemes are applied to restore autonomic dysregulation based on natural diurnal patterns of sympathetic or parasympathetic activity. Treatment could also occur at irregular intervals that are human-entered or predicted by machine learning from previous days' voiding incidents. In some embodiments, a first frequency (e.g., 10 Hz or 20 Hz) therapy can be applied in the morning for acute day time relief, and a second different higher or lower frequency (e.g., 20 Hz or 10 Hz) therapy can be provided before bed for longer night time relief.

In some embodiments, the responsiveness could be dependent on activity. For instance in nocturia, a motion sensor such as an accelerometer or gyroscope could sense if a person is stirring, which could indicate a desired potential voiding. During that time, the device could turn on to provide appropriate stimulation. In some embodiments, the device could turn off once voiding is complete.

In some embodiments, the responsiveness of stimulation could be dependent on one, two, or more sensors housed in the device to collect, store, and analyze biological measures about the wearer including, but not limited to, motion (e.g., accelerometers, gyroscopes, magnetometer, bend sensors), ground reaction force or foot pressure (e.g., force sensors or pressure insoles), muscle activity (e.g., EMG), cardiovascular measures (e.g., heart rate, HRV), skin conductance (e.g., skin conductance response, galvanic skin response), respiratory rate, skin temperature, and sleep state (e.g., awake, light sleep, deep sleep, REM). Using standard statistical analysis techniques, such as a logistical regression or a Naïve Bayesian classifier, these biological measures can be analyzed to assess the wearer's activity state, such as sedentary versus active, level of stress and/or bladder fluid volume, and the like, which in turn, can serve as a predictor for increases in urinary urgency.

Sympathetic and parasympathetic activity can be measured through several methods, including microneurography (MSNA), catecholamine tests, heart rate, HRV, or galvanic skin response. HRV can provide a quick and effective approximation of autonomic activity in the body. HRV can be determined by analyzing the time intervals between heartbeats, also known as IRR intervals. Heart rate can be accurately captured, for example, through recording devices such as chest straps or finger sensors. The differences between successive RR intervals can provide a picture of one's heart health and autonomic activity. Generally speaking, healthier hearts have more variability between successive RR-intervals. This interbeat data can also be used to denote an individual's sympathetic and parasympathetic activity levels. Through frequency-domain analysis, heartbeat frequencies can be separated into distinct bands. High-frequency signals (~0.15-0.4 Hz) can almost exclusively reflect parasympathetic activity, and low-frequency signals (~0.04-0.15 Hz) can represent a mixture of sympathetic and parasympathetic activity. Therefore, taking the ratio of high frequency (HF) to low frequency (LF) signals can yield an approximation of one's sympathetic tone. In some embodiments, HRV can be analyzed, for example, under time-domain, geometric domain methods in addition to frequency domain methods. In some embodiments, increased heart rate variability can signify increased parasympathetic response and/or decreased sympathetic response. Decreased heart rate variability can signify decreased parasympathetic response and/or increased sympathetic response. In some embodiments, a system can sense an increase or decrease in HRV of about or more than about 5%, 10%, 15%, 20%, 25%, 30%, 35%, 40%, 45%, 50%, 75%, 100%, or more over a baseline value (or target desired HRV value) and institute a change in one, two, or more stimulation modality parameters accordingly. In some embodiments, the one, two, or more stimulation modalities can be configured to modulate, such as increase or decrease stimulation to one or more nerves (e.g., peripheral nerves) associated with the sympathetic and/or parasympathetic nervous system, and a response to therapy can be confirmed by sensing an increase or decrease in parasympathetic or sympathetic tone, including but not limited to increase or decrease in HRV, changes in high frequency content of HRV, and changes in the ratio of high frequency and low frequency content of HRV. In some embodiments, balance of parasympathetic and sympathetic activity of the bladder reflex loop can be assessed with frequency analysis of heart rate variability measured with pulsed plethysmography with an LED light source and optical sensor disposed in the device that measures fluctuations in light level due to blood flow that target one of the major blood vessels around the knee, which could include one or more of the following, femoral, popliteal, tibial, posterior tibial, anterior tibial, and/or descending genicular arteries or veins.

In some embodiments, a system or method for non-invasively measuring eye muscle movement and/or the blink reflex can be utilized as a biomarker (e.g., a biological marker that can be used to inform diagnosis of a disease state) of diagnosis of overactive bladder or other conditions, monitoring of the progression or efficacy of therapy of overactive bladder or other conditions, and/or be utilized as feedback parameters regarding closed-loop adjustment of therapy. Not to be limited by theory, the centers involved in the control of micturition, such as the medial and lateral regions of the pontine micturition center are in the reticular formation of pontine tegmentum and in close anatomical proximity to regions that control eye muscle movement and/or for coordinating the blink reflex. Thus, such biomarkers can be used to gauge functions that are either integrated in, or mediated by the pontine structures. For example, an increased blink latency time (such as about or at least about 1%, 2%, 3%, 4%, 5%, 6%, 7%, 8%, 9%, 10%, 15%, 20%, 25%, or more) compared to reference values can be in some cases associated with overactive bladder symptoms. In some embodiments, a patient's baseline eye muscle movement parameter such as blink time can be compared with parameters/times of the patient while on or after therapy for comparison. Some embodiments could involve, for example: video eye tracking or blinking (such as via a camera, including a web camera, tablet or smartphone camera, or a wearable device that includes a camera, e.g., headwear such as a cap, glasses such as a modified Google Glass, and the like); electro-oculography eye muscle recording based on the dipole of the eye; EMG of muscles on the head that control blinking, such as the orbicularis oculi and levator palpebrae superioris muscle; a system to induce a blink, such as a bright light or puff of air into the eye, and then measuring time to blink using a camera or EMG; and/or measurement of the blink reflex with an active stimulation signal, such as applied transcutaneously to the supraorbital nerve and recording of nerve activity of the orbicularis oculi.

In some embodiments, any form of stimulation as disclosed herein can be utilized to apply stimulation to one, two, or more acupuncture points. In some embodiments, the acupuncture points to be stimulated could include any one, two, three, four, five, six, seven, eight, nine, ten, or any other number of the following: BL18 (Ganshu), BL23 (Shenshu), BL27 (Xiaochangshu); BL28 (Pangguangshu); BL32 (Ciliao); BL33 (Zhongliao); BL53 (Baohuang); CV2 (Qugu); CV3 (Zhongji); CV4 (Guanyuan); CV5 (Shinen); CV6 (Qihai); GB34 (Yanglingquan); KI7 (Fuliu); KI10 (Yingu); LR1 (Dadun); LR2 (Xingjian); LR8 (Quan); N-BW-38 (Xiajiaoshu); SP6 (Sanyinjiao); SP9 (Yinlingquan); and/or ST28 (Shuidao). In some embodiments, the points to be stimulated include BL18, BL23, BL28, and CV2. In some embodiments, the points to be stimulated include ST28, SP6, BL23, BL28, BL32, BL53, CV3, and N-BW-38. In some embodiments, the points to be stimulated include SP6, BL23, BL27, BL28, BL33, and CV4. In some embodiments, the points to be stimulated include SP9, LR1, LR2, CV4, and CV6. In some embodiments, the points to be stimulated include SP6, SP9, BL23, CV3, and CV6. In some embodiments, the points to be stimulated include SP9 and GB34. In some embodiments, the points to be stimulated include SP9, KI7, KI10, and LR8. In some embodiments, the point to be stimulated is either CV5 alone or BL39 alone, or a combination thereof. Other permutations of stimulation points are also possible, depending on the desired clinical result. FIGS. 1C-1G illustrate non-limiting examples of potential acupuncture points that can be stimulated, in accordance with some embodiments of the invention.

A large source of error in optical measurements of heart rate is motion artifacts due to relative motion between the optical sensor and the blood vessel being measures. In some embodiments, the optical heart rate sensor has an adhesive on the side of housing that contacts the wearer's skin to reduce relative motion between the sensor and the target blood vessel.

In some embodiments, one, two, or more additional sensors are disposed in the device, including electrical sensors in contact with the wearer's skin to measure cardiac activity or pressure sensors to measure changes in blood vessels, to be used in combination with an optical sensor to improve the fidelity of heart rate measurement.

In some embodiments, the system and device have memory and a processor to extract RR intervals from sensor data, calculate variability of RR intervals, transform data into frequency domain, and calculate high frequency signals, low frequency signals, and the ration of the high frequency and low frequency signals.

In some embodiments, the heart rate sensor can store collected data for specified time period to gather adequate date for heart rate variability calculation. Specified time period can range in some cases from 1-60 seconds, and may extend to 10 minutes or more.

In some embodiments, electrodermal activity, also known as galvanic skin response or skin conductance response, for example, can be measured using sensors, such as electrodes. Galvanic skin response is the change of the electrical resistance of the skin caused by emotional stress, and measurable with, e.g., a sensitive galvanometer. Not to be limited by theory, skin resistance varies with the state of sweat glands in the skin. Sweating is controlled by the sympathetic nervous system, and skin conductance can be an indication of psychological or physiological arousal. If the sympathetic nervous system is highly aroused, then sweat gland activity also increases, which in turn increases skin conductance. In this way, skin conductance can be a measure of emotional and sympathetic responses, which can be measured, and the feedback data can be sent to the controller, which will in turn modulate stimulation to, for example, decrease sympathetic nervous system activity. Other non-limiting parameters associated with sympathetic and/or parasympathetic nervous system activity that can be sensed include, for example, sweating during particular times of the day and/or night, sleep states as detected, for example, by an EEG headband (to determine when sympathetic and/or parasympathetic activity is particularly high or low, and potentially correlating a sleep state such as stage 1, 2, 3, 4, or REM with nocturia), and/or motion. In some embodiments, a diagnostic and/or combination diagnostic/stimulation device can be configured to measure a person's heart rate and galvanic skin response for improved estimation of the person's autonomic activity. In some embodiments, a wearable device, such as a wrist-worn device can include both electrodermal activity (EDA) sensors and optical heart rate sensors. This combination of data can in some embodiments advantageously and synergistically provide improved estimation of sympathetic and parasympathetic activity than a single measure alone. In some embodiments, the system can include multiple sensors to measure electrodermal activity in conjunction with heart rate and HRV. Data from the multiple sensors can be analyzed by a hardware or software processor and combined to provide a more accurate estimation of sympathetic and/or parasympathetic activity. In some embodiments, the EDA and HR sensors can be disposed in a wrist-worn device that communicates via a wired or wireless connection to the stimulator or to send data to a centralized remote server (e.g., the cloud). Stimulation parameters, nerve target locations (e.g., tibial and/or saphenous nerves for example) or dosing regimen (e.g., duration or frequency of stimulation sessions) could be adjusted based on estimations of sympathetic and/or parasympathetic activity. Adjustments could be made in real-time, or in subsequent stimulation sessions. In some embodiments, stimulation frequency can be adjusted to either increase or decrease autonomic activity modulated by a single specific nerve, or multiple nerves. For example, in some embodiments, relatively low frequency stimulation of a target nerve (e.g., below a threshold value, e.g., about 5 Hz) can potentially inhibit the nerve and thus decreases sympathetic activity, while higher frequency stimulation (e.g., above a threshold value, e.g., about 5 Hz) can potentially excite the nerve and thus increases sympathetic activity. The same effect can occur with the same or other target nerves to regulate parasympathetic activity. In other words, in some embodiments, relatively low frequency stimulation of the target nerve (e.g., below a threshold value, e.g., about 5 Hz) can potentially inhibit the nerve and thus decreases parasympathetic activity, while higher frequency stimulation (e.g., above a threshold value, e.g., about 5 Hz) can potentially excite the nerve and thus increases parasympathetic activity. Not to be limited by theory, depending on the stimulation parameters for example, in some cases stimulating the target nerve can increase or decrease either sympathetic activity, parasympathetic activity, or both. In some embodiments, stimulation of the saphenous nerve can affect sympathetic activity, and stimulation of the tibial nerve can affect parasympathetic activity.

The device could also be responsive to number of episodes of symptoms, including overactive bladder. If more episodes occur in one day, treatment can be increased by increasing the amplitude of the stimulation, duration of the stimulation, or number of treatment sessions, for example.

The number of episodes of symptoms such as overactive bladder could be detected in various ways to control the stimulation applied by system and devices. In some embodiments, the patient can enter events related to symptoms of overactive bladder, including but not limited to bladder voiding events, urgency event, or incontinence events on a mobile device. In some embodiments, location services on the device, such as GPS, can detect when the person has entered a building or bathroom.

Figure 2:
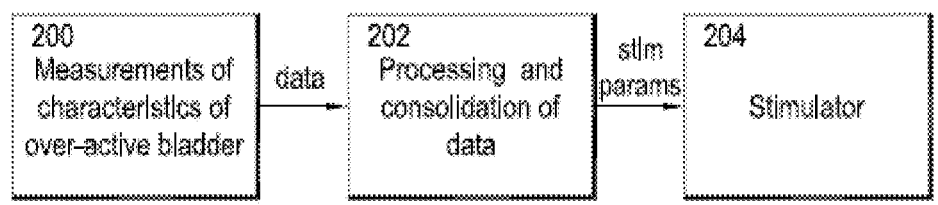
FIG. 2 schematically illustrates a flow chart incorporating a stimulation protocol, according to some embodiments of the invention.

Information regarding bladder voiding can be combined in some embodiments with an understanding of the amount of fluid a person has consumed in order to better apply a desired amount of treatment. For example, in days where more beverages were consumed by an individual, more bladder voiding would be expected. FIG. 2 schematically illustrates a flow chart incorporating a stimulation protocol, according to some embodiments of the invention. The times, amounts, and types of beverages ingested by a patient over the day can be recorded manually or electronically, such as in a software application, as shown in box 200. Knowing when and what was consumed can be used to predict when and how much a person's bladder should be emptied and the amount of treatment can be applied accordingly. The information regarding the processing time of a certain amount of liquid in the human body could be used to anticipate through literature studies with additional information from the patient (such as gender, weight, and height, and potentially measuring bladder size using an initial pelvic ultrasound procedure). This processing and consolidation of data (shown in box 202) to anticipate the amount and timing of treatment necessary can be done within a single device or utilizing another separate device, for instance a mobile phone. In this manner, stimulation 204 can be applied accordingly based on the number of episodes a person experiences.

One method of recording the times and types of beverages consumed is through a journal or diary, for example on a smartphone, tablet, or other device. Another method of achieving this is to use a device such as a smart cup that identifies the types and amounts of beverages consumed through the day and syncs this information to the system or device. This information can advantageously be an automatic journal of the amount of liquids consumed through the day.

Figure 2A:
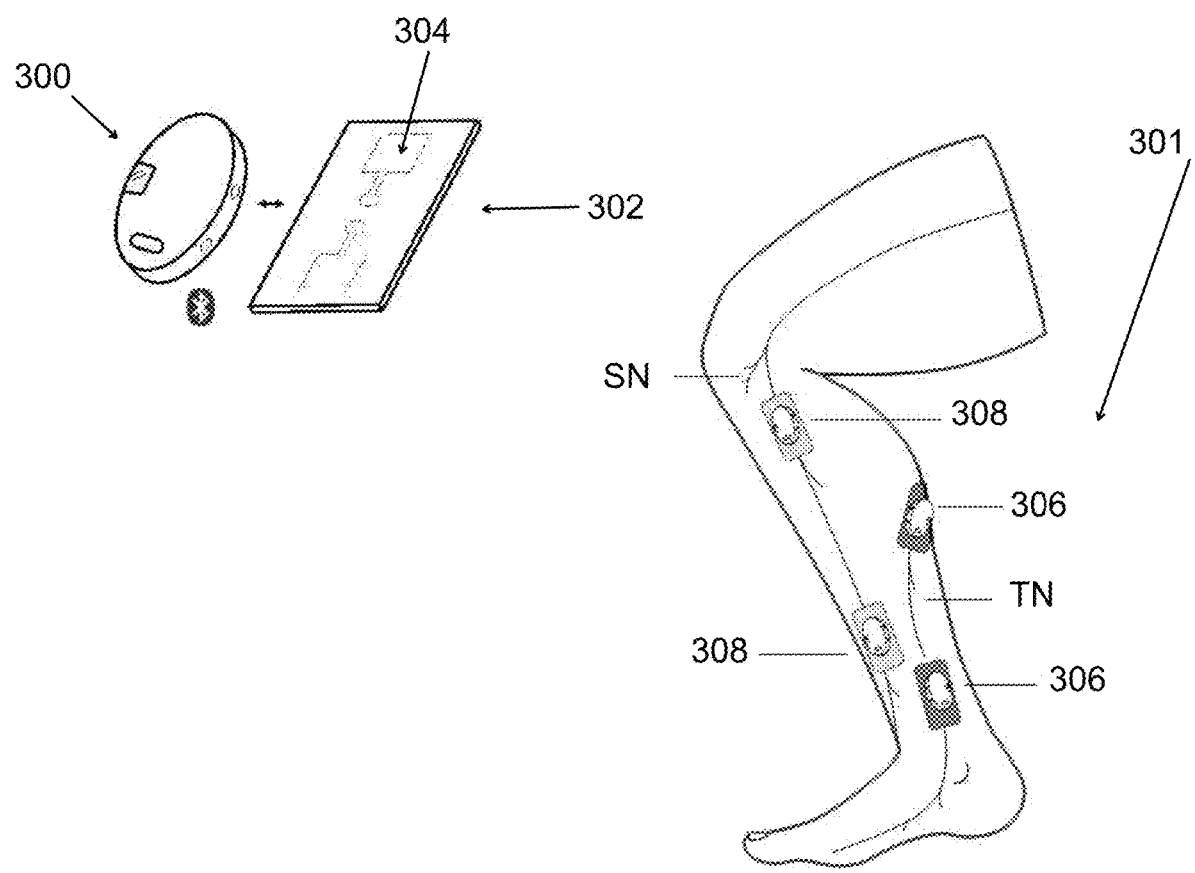
FIG. 2A schematically illustrates a stimulation system with a plurality of stimulator housings that can include or be operably connected to a patch having electrodes and a skin-contacting surface.

Bladder control and comfort require a delicate balance of sympathetic, parasympathetic, somatic efferent and afferent innervation of the bladder reflex circuits. In some embodiments, a variable frequency stimulator in electrical connection with three or more electrodes to target at least two nerves that provide sympathetic, parasympathetic and somatic input into the bladder reflex circuits. In some embodiments, the device is disposed in a knee strap fitted just below the knee with a fastening mechanism to hold the device securely on the body. In some embodiments, the electrodes, constructed from an adhesive hydrogel, are disposed in the housing of the device allowing the device to adhere to the wearer's skin. In some embodiments, a system can include a plurality of stimulators that communicate with each other wirelessly and provided a synchronized continuous or patterned stimulation. In some embodiments, multiple stimulators may be in electrical connection with multiple electrode pairs to stimulate multiple nerves simultaneously. Each stimulator in the system can communicate with each other via a wired or wireless connection. Multiple stimulators can provide synchronized stimulation to the multiple nerves. Stimulation may be, for example, burst, offset, or alternating between the multiple nerves. FIG. 2A schematically illustrates a stimulation system 301 with a plurality of stimulator housings 300 that can include or be operably connected to a patch 302 having electrodes 304 and a skin-contacting surface. Each individual stimulator 306 (shown positioned to stimulate the tibial nerve TN), or stimulator 308 (shown positioned to stimulate the saphenous nerve SN) can be placed, for example, transcutaneously below the knee and/or above the ankle as illustrated. The stimulators can be placed sufficient to stimulate the saphenous and/or tibial nerves. The stimulators can be placed in some cases between the knee and the ankle, such as in the proximal calf (such as within the most 25% proximal section of the calf, or between the 25% and 50% most proximal section of the calf), distal calf (such as the most 25% distal section of the calf or between the 25% and 50% most distal section of the calf), or combinations thereof. The stimulators can be physically discrete for each other, or combined into a single housing such as a calf band or other form factor as described elsewhere herein.

Figure 2B:
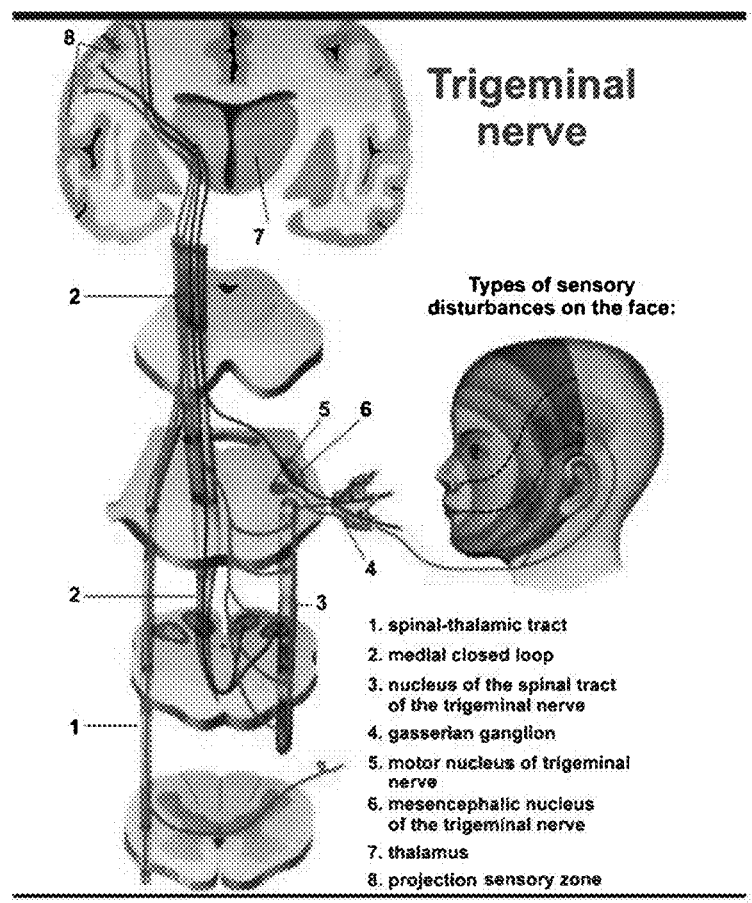
FIG. 2B schematically illustrates trigeminal nerve pathways.

In some embodiments, systems and methods can stimulate a plurality of nerves associated with bladder function, including but not limited to peripheral nerves in different anatomical locations. For example, stimulation could include one or more nerve targets on an extremity or extremities of a patient, and one or more nerve targets on the head of a patient. Some embodiments can involve stimulation of saphenous, tibial nerves, and/or other nerves as disclosed elsewhere herein in coordination with pontine nuclei stimulation via peripheral nerve targets in order to control centers involved in micturition. The stimulation of the saphenous, tibial, and/or other nerves could be simultaneous, overlapping, or at different times with respect to that of the stimulation of the pontine micturition center, such as at intervals disclosed elsewhere herein. The centers involved in the control of micturition, e.g., the medial and lateral regions of the pontine micturition center are in the reticular formation of pontine tegmentum which lies in close anatomical proximity to regions innervated by the trigeminal and facial nerve. FIG. 2B schematically illustrates trigeminal nerve pathways, including the spinal-thalamic tract; medial closed loop; nucleus of the spinal tract of the trigeminal nerve; gasserian ganglion; motor nucleus of the trigeminal nerve; mesencephalic nucleus of the trigeminal nerve; thalamus; and the projection sensory zone. Stimulation of the trigeminal and/or facial nerve, such as transcutaneously or percutaneously for example, to effect neuromodulation of the micturition centers can provide additional physiological control of these centers that are dysregulated in overactive bladder for synergistic and unexpectedly beneficial clinical results in some cases. In some embodiments, one, two, or more branches of the trigeminal nerve (e.g., the ophthalmic nerve (V1), the maxillary nerve (V2), and/or the mandibular nerve (V3)) are stimulated. In some embodiments, instead of or in addition, one, two, or more branches of the facial nerve (e.g., posterior auricular nerve, temporal branch, zygomatic branch, buccal branch, marginal mandibular branch, and/or cervical branch) can be stimulated to modulate the control centers involved with micturition.

Figure 3:
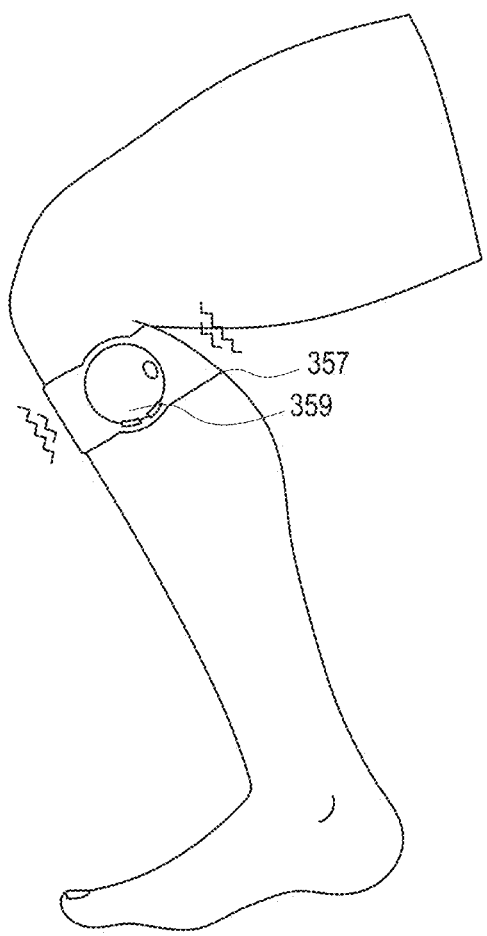
FIG. 3 illustrates a calf band stimulator configured to be positioned proximate the knee, according to some embodiments of the invention.
Figure 4B:
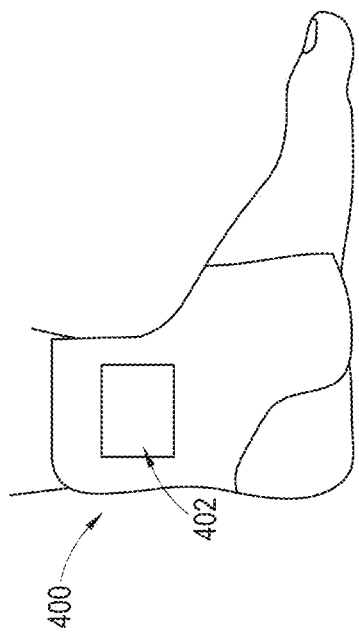
FIGS. 4A-4B illustrate ankle stimulators, according to some embodiments of the invention.
Figure 4A:
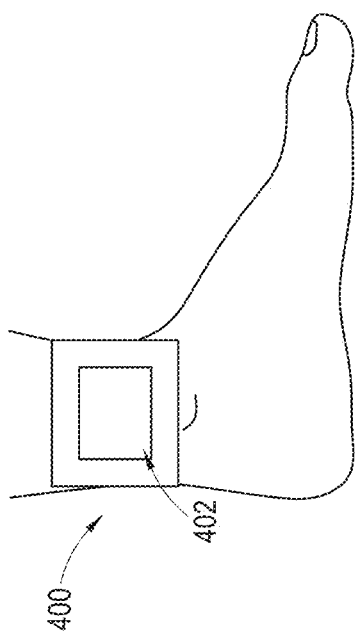

In some embodiments, as shown schematically in FIG. 3, the nerve stimulator can be designed like a calf band 357 having a stimulator housing 359 attached thereto and configured to be positioned just distal to the knee for stimulating the tibial nerve and the saphenous nerve transcutaneously. As illustrated in FIGS. 4A-4B, the nerve stimulator can include an ankle brace or anklet 400 with a stimulator box 402 (shown in FIG. 4A) or an ankle brace (shown in FIG. 4B). This for factor could also be extended to a sock, shoe, boot, or stocking for example. These form factors can be advantageous in some cases, as they are compact and do not necessarily interfere with gait. The electrodes can be integrated into a garment in the form of conductive polymers or silver fabrics, for example. In some embodiments, dry electrodes can be utilized, such as dry electrodes that include a conductive backing layer (e.g., a metal foil material, such as disposed on a flexible polymer substrate) and a skin contact layer disposed on the conductive backing layer, that can include for example a polymer, plastic, or rubber material, and a conductive filler material (e.g., powder, fine particulate material, metal, carbon, mixtures thereof, or porous material treated with a conductive coating) dispersed substantially evenly throughout the silicone, plastic, or rubber material. In some embodiments, the skin contact layer has a skin facing surface that is not coated with a hydrogel or liquid. In some embodiments, the dry electrodes can be as disclosed in U.S. Prov. App. No. 62/432,519, filed on Dec. 9, 2016, hereby incorporated by reference in its entirety.

In some embodiments, the weave of the brace or sock could be designed to provide tight pressure at the knee, calf, ankle, or other desired region of the device, similar to the weave of commonly found anklet socks. Electrodes can also be made from, for example, conventional hydrogels. In some cases, a clasp or fastening element such as Velcro may be needed because with sticky electrodes, the device cannot be easily slid on the foot. In some embodiments, the, e.g., knee, calf, ankle brace or anklet embodiments can be extended to electrode positions that are on the top (dorsal) or bottom (ventral) surfaces of the foot. In some cases, a sock with electrodes on the sole of the foot can be used with connectivity through the sock to an electronics module located near the ankle.

FIGS. 5A-5C illustrate non-limiting embodiments of potential electrode placement locations for nerve stimulation. The sensor systems, including those disclosed herein can communicate via wires or wirelessly to the stimulator 502. Placement of the electrodes of the tibial stimulator could vary with electrodes 500 placed along the tibial nerve (FIG. 5A), at the bottom of the foot (FIG. 5C), or on either side of the ankle or attached to a stimulator (FIG. 5B).

In some embodiments if the electrodes 606 are sticky, as shown in the embodiment of FIGS. 6-7, a device 600 in the form of a bandage can be made, which circumferentially or non-circumferentially envelop a portion of a body part, such as an extremity. The strip can be any shape, including an annular, square, rectangular, triangular, or other shape. In some cases, the electronics can be located inside a removable housing 602 that can be removably attached at site 604 from the entire device 600 when the disposable is thrown away. FIG. 6 is a bottom view, while FIG. 7 is a top view of the device 600.

Figure 8:
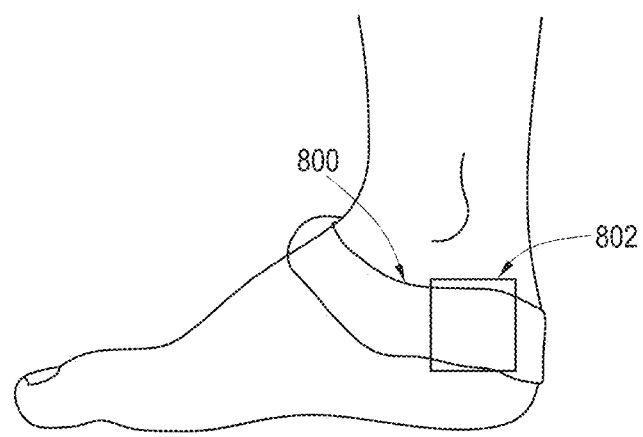
FIG. 8 illustrates a thin, bandage-like electrode that can be attached to the patient, according to some embodiments of the invention.

In another embodiment, as illustrated in FIG. 8, a thin, bandage-like electrode 802 can be attached to the patient. Power can be coupled from a battery source that is loosely wrapped around the target body region, such as the knee or ankle for example, like a knee band, thigh band, calf band, an anklet 800 or sock, or located on the side of the shoe in the general vicinity of the electrode. In some embodiments, power can be delivered wirelessly to the electrode 802, such as via inductive charging. This configuration can be advantageous, in some embodiments, in that the disposable can be made very thin, increasing the comfort of the skin interface even if the disposable is very sticky (this is analogous to an adhesive bandage). This embodiment can also be adapted for use if the electrode bandages are placed on the bottom of the foot. In some cases, the electronics could be located/clipped on the top of a shoe or in the sole of the shoe. In some embodiments, the electronics housing can be in direct electrical connection with a sticky, hydrogel patch that is removable and disposable after stimulation sessions. The patch may last for, for example, about, at least about, or no more than about one session, one day, or up to 2 weeks or more. In some embodiments, the patch may contain passive electronic components, including capacitors or resistors, or active electronic components, such as memory or RFD tags, to uniquely identify the type of patch attached to the stimulator, for example, a patch for specific nerve targets such as the saphenous nerve or the tibial nerve, or a particular stimulation waveform, such as about 10 Hz or about 20 Hz, or a combination thereof.

Several peripheral nerves in addition to, or instead of the tibial nerve can serve as targets for urinary neuromodulation, including the pudendal and dorsal genital nerve, with acute and/or chronic effects on bladder function in animal and human experimental studies. Saphenous nerve stimulation can acutely or chronically reduce bladder hyperexcitability. The saphenous nerve is a purely sensory nerve that innervates the skin on the medial lower leg. Its proximity to the skin surface makes it an advantageous target in some embodiments for transcutaneous stimulation. Selective stimulation of the saphenous nerve can in some embodiments advantageously reduce overactive bladder symptoms. In some embodiments, peripheral nerves can be independently targeted with specific same or differing frequencies to prove acute or chronic relief of symptoms of overactive bladder, and/or to alter sympathetic and/or parasympathetic activity.

The effects of peripheral nerve stimulation on bladder function may occur only during the period of active stimulation in some embodiments, or may outlast the stimulation period after stimulation has ceased. Different mechanisms such as the modulation of urinary reflexes or induction of brain and/or spinal plasticity can be triggered using systems and methods as disclosed herein. Furthermore, in some cases the onset of the effects of stimulation may occur acutely or only after several stimulation sessions in a chronic manner. For example, the effect of transcutaneous or percutaneous tibial nerve stimulation on patient related outcomes is estimated in some embodiments at 4-6 weeks after the initiation of weekly stimulation sessions. Depending on the underlying mechanisms and the time course of beneficial effects, stimulation may require delivery in a continuous fashion such as in sacral nerve stimulation, in discrete scheduled sessions or in an on-demand, conditional manner. Conditional stimulation may either rely on patient control to identify the sense of urinary urge or automated detection of an involuntary detrusor contraction (IDC) which is responsible for urgency symptoms or evolution to frank incontinence.

Conditional stimulation of the dorsal genital nerve and/or pudendal nerve can be advantageous in some embodiments. Alternatively or in addition, continuous stimulation can be utilized to control bladder symptoms. The advantages of conditional stimulation in some embodiments can include customization of symptom control, improved battery life, and reduction of the risk of habituation with continuous stimulation. A patient controlled conditional stimulation device for overactive bladder may be effective for suppressing urge symptoms prior to the progression to incontinence.

The stimulation frequency can be varied depending on the desired clinical result. In some embodiments, a relatively higher frequency, such as between about 10 Hz and about 33 Hz, between about 10 Hz and about 30 Hz, between about 10 Hz and about 20 Hz, or between about 20 Hz and about 33 Hz, or about or at least about 10 Hz, 15 Hz, 20 Hz, 25 Hz, 30 Hz, 33 Hz, 35 Hz, or more can be used. The stimulation frequency can also be tailored to the specific nerve targeted. In some embodiments, lower stimulation rates such as 2 Hz can have an excitatory effect on bladder function and worsen incontinence. However, in some embodiments, a frequency of about or no more than about 10 Hz, 9 Hz, 8 Hz, 7 Hz, 6 Hz, 5 Hz, 4 Hz, 3 Hz, 2 Hz, or 1 Hz can be utilized. In some embodiments, the stimulation frequency could be in the kHz range, such as, for example, between about 1 kHz and about 100 kHz, such as between about 10 kHz and about 50 kHz. The stimulation could be regular, irregular, or random in some embodiments. In some embodiments, a frequency or a plurality of frequencies for one, two, or more nerves could be selected from, for example, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 Hz. In some embodiments, two or more of the same or different frequencies or frequency ranges can be applied to the same or different target nerves.

The exact location of stimulation in the lower leg can vary depending on the desired target. For example, the tibial nerve may be stimulated at the level of the ankle or behind the knee. As the saphenous nerve territory is over the medial lower leg, stimulation of the nerve may be achieved at the ankle or closer to the knee in some cases.

In some embodiments, stimulation of the saphenous nerve can be used instead of or in conjunction with tibial nerve stimulation to treat overactive bladder and/or urinary incontinence. The saphenous nerve runs through the upper leg, descends along the medial side of the knee, descends along the tibial side of the lower leg and divides into two branches, a branch that continues to descend along the tibia that extends to the ankle and a branch that passes in front of the ankle and extends along the medial side of the foot.

In some embodiments, a stimulator worn around the ankle or lower leg or knee or upper leg can be used to stimulate the saphenous nerve and, optionally, also the tibial nerve. In other embodiments, the stimulator can be worn around any other part of the leg or foot in order to stimulate the saphenous nerve at other locations. The electrode(s) of the stimulator can be placed proximate or over the saphenous nerve.

In some embodiments, the stimulation can be electrical and be provided transcutaneously using an electrode placed on the patient's skin. In some embodiments, the stimulation of the saphenous nerve can be patient activated. In some embodiments, the stimulation of the saphenous nerve can be automated and/or patient activated. In some embodiments, the stimulation of the saphenous nerve can be solely patient activated, meaning the stimulation is only provided while the patient is awake. If stimulation while the patient is asleep is desired, an automated stimulation regimen can be provided.

Figure 9:
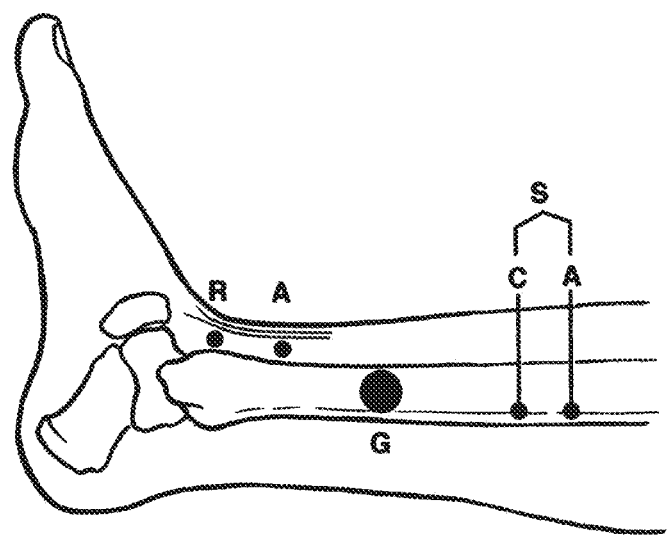
FIG. 9 illustrates an embodiment of a distal saphenous nerve sensing and/or stimulation technique.

FIG. 9 illustrates an embodiment of a distal saphenous nerve sensing and/or stimulation technique. In some embodiments, the therapy can be performed in a supine, upright, or sitting position. In some embodiments, a bar electrode (e.g., 3 cm) can be used. A reference electrode (R) can be positioned slightly anterior to the highest prominence of the medial malleolus, between the malleolus and the tendon of the tibialis anterior. The active electrode (A) can be positioned proximal and slightly medial to the tibialis anterior tendon. A return, e.g., ground electrode (G) can be placed, for example, between the recording electrodes and the cathode. With regard to the stimulation point (S), the cathode (C) can be placed, for example, 14 cm proximal to the active electrode deep to the medial border of the tibia. The anode (A) can be, for example, proximal. In some embodiments, the device settings could include any of the following: Sensitivity—2-5 µV/division, Low frequency filter—20 Hz, High frequency filter—2 kHz, Sweep speed—1 msec/division. In some embodiments, the L3 and L4 nerve roots, through the posterior division of the lumbosacral plexus, can be tested. In some embodiments, sensing and its associated components such as the reference electrode (R) may not be required.

Figure 10:
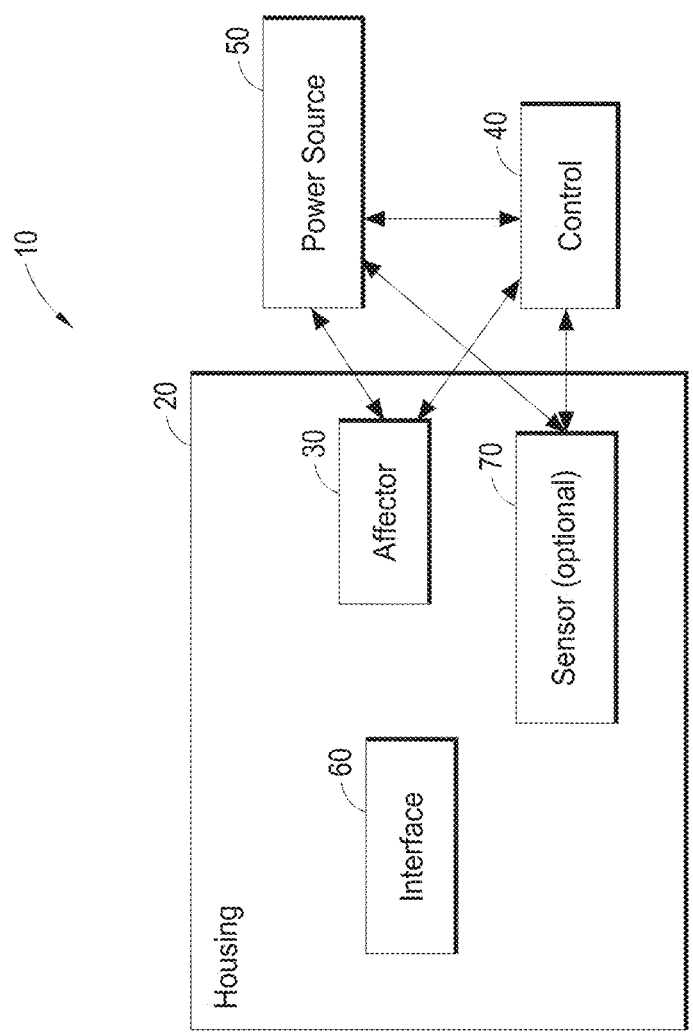
FIG. 10 illustrates a stimulation device including a housing, according to some embodiments of the invention.

In some embodiments, a device for stimulating one, two, or more nerves is illustrated schematically in FIG. 10. The device 10 can include a housing 20 and one, two or more effectors 30, power sources 50, and/or controls 40. In some embodiments, the device further includes one or more sensors 70. The effectors can include a pulse generator and electrodes for delivering electrical stimulation, and/or can be a mechanical stimulator for delivering mechanical stimulation, such as vibratory stimulation, for example. The sensors can include, for example, accelerometers, gyroscopes, and electrodes to measure electrical activity including nerve activity and muscle activity.

Figure 10A:
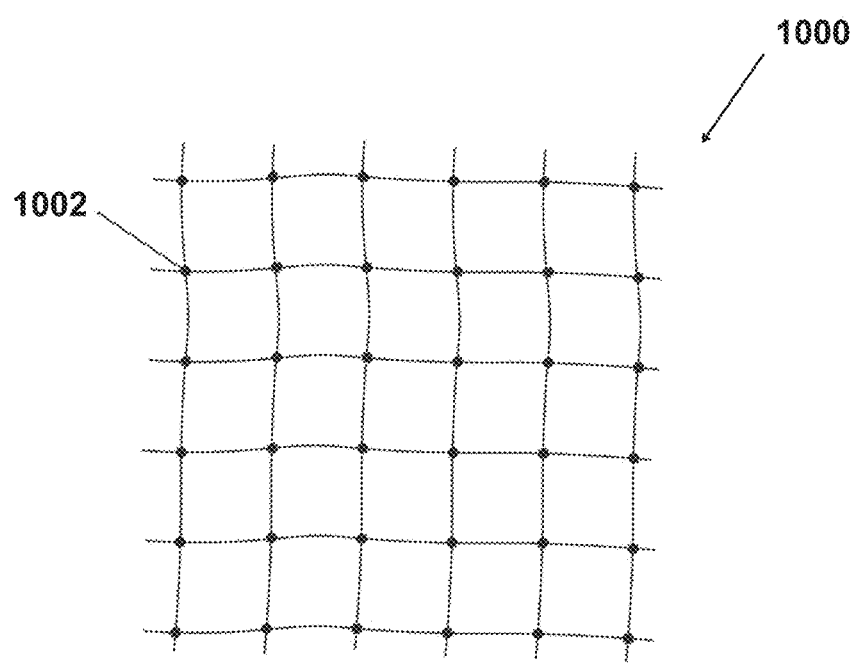
FIG. 10A illustrates an embodiment of an electrode array with elements that can be individually addressable.

In some embodiments, as illustrated in FIG. 10A, the device can include a 2D or 3D array of electrodes 1000 such that the stimulation may be targeted. The elements 1002 may be individually addressable such that the location of stimulation can be adjusted on-the-fly or for each session, such as electronic referencing. Alternatively, the elements may be configured for an individual user, such as a mechanical configuration in which the electrode connections are cut or spliced to customize the device.

Figure 10B:
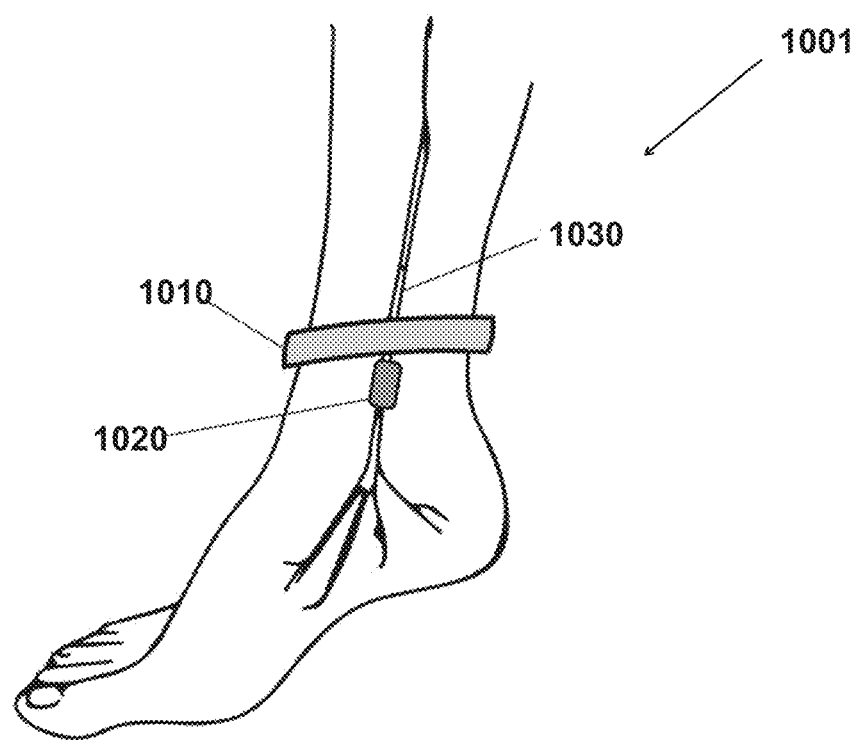
FIG. 10B illustrates an embodiment of a stimulation system including a wearable device on the ankle or other desired anatomical location, as well as an implanted stimulation electrode around a target nerve.
Figure 11E:
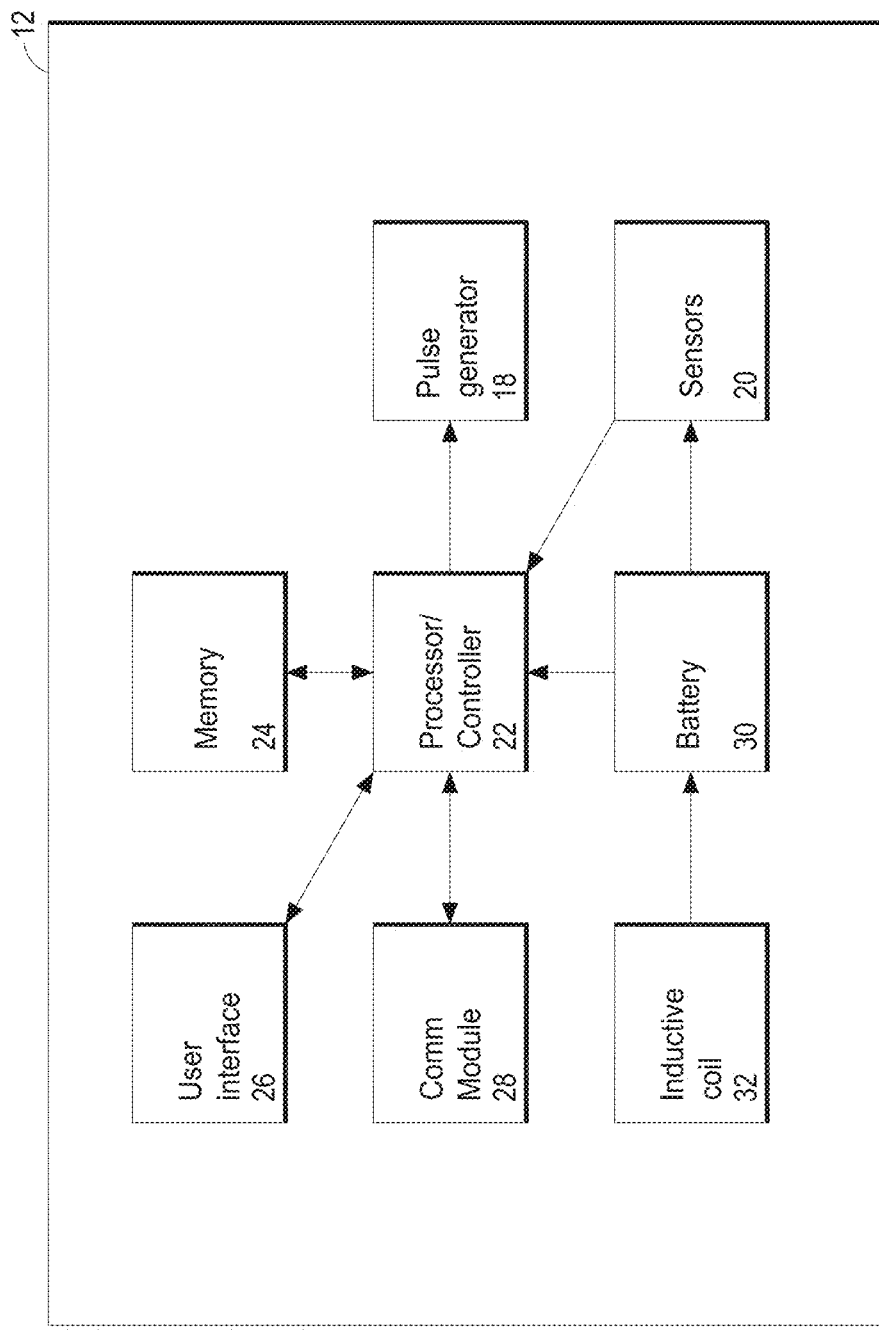

FIG. 10B illustrates an embodiment of a stimulation system 1001 including a wearable device 1010 on the ankle or other desired anatomical location, as well as an implanted stimulation electrode 1020 around a target nerve 1030, such as the tibial nerve for example. In another embodiment, the wearable device may be a component of a stimulation system including subcutaneous, transcutaneous, and/or percutaneous components. For example, the wearable device may communicate with an implanted stimulation device to power and control the device. Additionally, the implantable electrode can be powered by a rechargeable battery housed within the implant and recharged wirelessly from an external power source or the wearable device. Alternatively, the wearable may contain a guiding array used to direct the location of percutaneous needles either in a patient-directed or healthcare setting.

In some embodiments, an implanted electrode that stimulates the nerve can be powered by an external stimulation unit, and the stimulation pulse is directly coupled to the electrode and nerve using capacitive or inductive coupling. In some embodiments, the wearable device can communicate with an external computer or device (e.g., tablet, smartphone, smartwatch, or custom base station) to store data. Communication between the wearable device and external device can be a direct, physical connection, or with a wireless communication connection such as Bluetooth, Wi-Fi, Zigbee, GSM, or cellular for example. In some embodiments, the system communicates with an external, portable computational device, such as a smartphone via an app, or other mobile digital interaction. The device may be used to track information of relevant events either user-entered or automatically captured from biological sensors, such as the time since the last urination and fluid intake, or biometric data predicting upcoming episodes of urinary incontinence or urinary urgency. This information may be used to close the loop to adjust stimulation parameters (waveforms, amplitude, on/off) or suggest user behaviors.

In some embodiments, the wearable device can have a GPS or similar device to track the location and assess activity of the wearer. GPS measures can be combined with mapping or location systems to determine context of the wearer's activity (e.g., gym versus office) or determine changes in elevation during specific activities, such as running or cycling.

In some embodiments, the wearable device can track parameters about stimulation provided by the stimulation unit, including time of stimulation, duration of the stimulation session, and power used by the stimulation unit. This data can be stored on memory in the wearable device, processed by the wearable device, and/or transmitted to an external computing device.

The stimulation unit can use switches or electrical sensor to detect connection of electrodes: (1) to ensure proper and unique electrodes are being installed (e.g., not using a different or incorrect type of electrode) communicating a unique code, for example via RFID, (2) to regulate the number of uses for each electrode to prevent over use, and/or (3) to prevent the usage of the device without an electrode to prevent small shock.

In some embodiments, a system may include features to increase skin comfort. One solution is to use a high frequency carrier (e.g., kHz such as 1 kHz or greater) wave over the low frequency beats (10 to 200 Hz), or to position electrodes such that the interaction of two waveforms combines to produce a low frequency beat.

In some embodiments, systems and methods of peripheral nerve stimulation can be provided that target one, two, or more individual nerves as illustrated in FIGS. 11A-11E. In some embodiments, the system 10 can that allows customization and optimization of transcutaneous electrical treatment to an individual. In particular, the device 10 described is for electrical stimulation of one, two, or more nerves. For example, a two electrode embodiment can be used to stimulate the tibial and/or saphenous nerve. Targeting these specific nerves and utilizing appropriately customized stimulation can in some embodiments result in more effective therapy. In some embodiments, the target nerves can include nerves in the leg, e.g., the tibial and/or saphenous nerve, which can be used to treat overactive bladder. In some embodiments, the device 10 can be configured to be worn on the leg, knee, or ankle and can be formed from a housing 12 and a band 14 or sleeve. In some embodiments, electronics and sensors located in a housing 12 can measure indications of bladder fullness or other symptoms of overactive bladder, as described herein. The electronics can include, for example, a pulse generator, a controller, and one, two, or more sensors such as an accelerometer and/or gyroscope and/or electrodes for measuring nerve activity. Electrical contacts and/or traces in the band 14 and/or housing 12 transmit the stimulation waveform from the pulse generator to the electrodes 16, which can be disposable. The location of the contacts in the band 12 can be arranged such that specific nerves are targeted, such as the tibial and/or saphenous nerve, or others including those disclosed herein. The housing 12 also can have a digital display screen to provide feedback about the stimulation and sensor data to the wearer of the device.

In some embodiments, disclosed herein is a dual nerve stimulator with the entire device or a portion thereof configured to be positioned just below the knee to target the saphenous and tibial nerves, including sensors for measuring slow changes in heart rate variability to assess autonomic dysregulation (e.g., to balance sympathetic and parasympathetic activity), and/or accelerometry for measuring overall activity, where the nerve targeted and the frequency of stimulation are controlled based on sensor data. Stimulation of each of the target nerves can be turned on or off independently, and the stimulation frequency can be adjusted independently to provide acute or chronic relief of symptoms due to a condition such as overactive bladder, as needed.

In some embodiments, the treatment device 10 can be a wearable device including an electronics box or housing 12 containing the stimulator or pulse generator 18, sensors 20, and other associated electronics such as a controller or processor 22 for executing instructions, memory 24 for storing instructions, a user interface 26 which can include a display and buttons, a communications module 28, a battery 30 that can be rechargeable, and optionally an inductive coil 32 for charging the battery 30, and the like. The device 10 can also include, for example, a band or sleeve to hold all the components together and securely fasten the device around the leg, knee, foot, or ankle of an individual. The device can also include, for example, a pair of electrodes on the band or sleeve.

Figure 12:
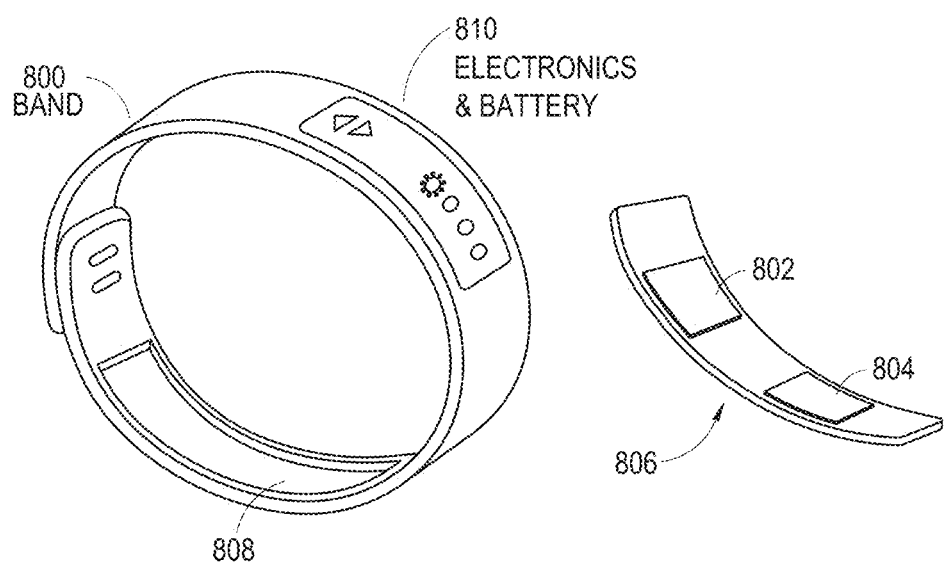
FIGS. 12 and 13 show that the electrodes can be disposed on a wearable band (or sleeve) that can be circumferential or non-circumferential, and worn around the ankle, knee, leg, or other body part according to some embodiments of the invention.
Figure 13:
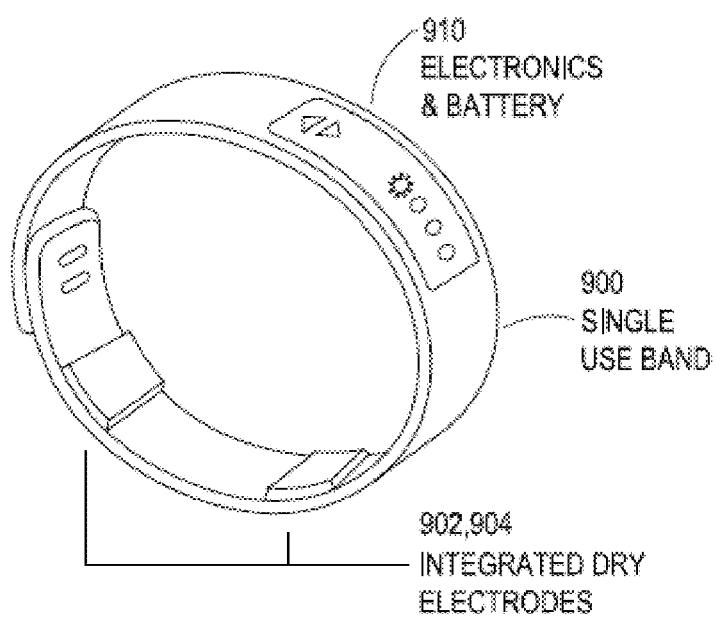

Additional system and device embodiments are shown in FIGS. 12 and 13, which show that the electrodes can be disposed on a wearable band (or sleeve) that can be circumferential or non-circumferential, and worn around the ankle, knee, leg, or other body part. The wearable band may include a removable/detachable controller as further described in International Application No. PCT/US2016/37080, titled SYSTEMS AND METHOD FOR PERIPHERAL NERVE STIMULATION TO TREAT TREMOR WITH DETACHABLE THERAPY AND MONITORING UNITS, which is hereby incorporated by reference in its entirety for all purposes. As shown, the wearable bands have two electrodes which can be used to stimulate up to two nerves. However, other embodiments can have N electrodes to stimulate up to N nerves, or N+1 electrodes to stimulate N nerves (e.g., 2 electrodes to stimulate up to 1 nerve; 3 electrodes to stimulate 2 nerves; or 4 electrodes to stimulate 3 nerves).

FIG. 12 illustrates a wearable band 800 with disposable electrodes 802, 804. The disposable electrodes 802, 804 can be coated or covered with an electrically conductive hydrogel and may be disposed on a strip 806 that can be removably attached to the wearable band 800, which may have a receptacle 808 for receiving the strip 806. The strip 806 and the band 800 can have electrical contacts and a flexible circuit so that the electrodes are electrically connected to the controller 810. To accommodate various body part sizes, the disposable strip 806 can be provided with a variety of electrode spacings. This allows one band size to accommodate users with different body part sizes. Since hydrogels can dry out, hydrogel coated electrodes may be more suitable for use with removable electrodes, as shown in FIG. 12, that can be disposed and replaced on a regular basis, such as every 1, 2, 3, 4, 5, 6, or 7 days.

Figure 12A:
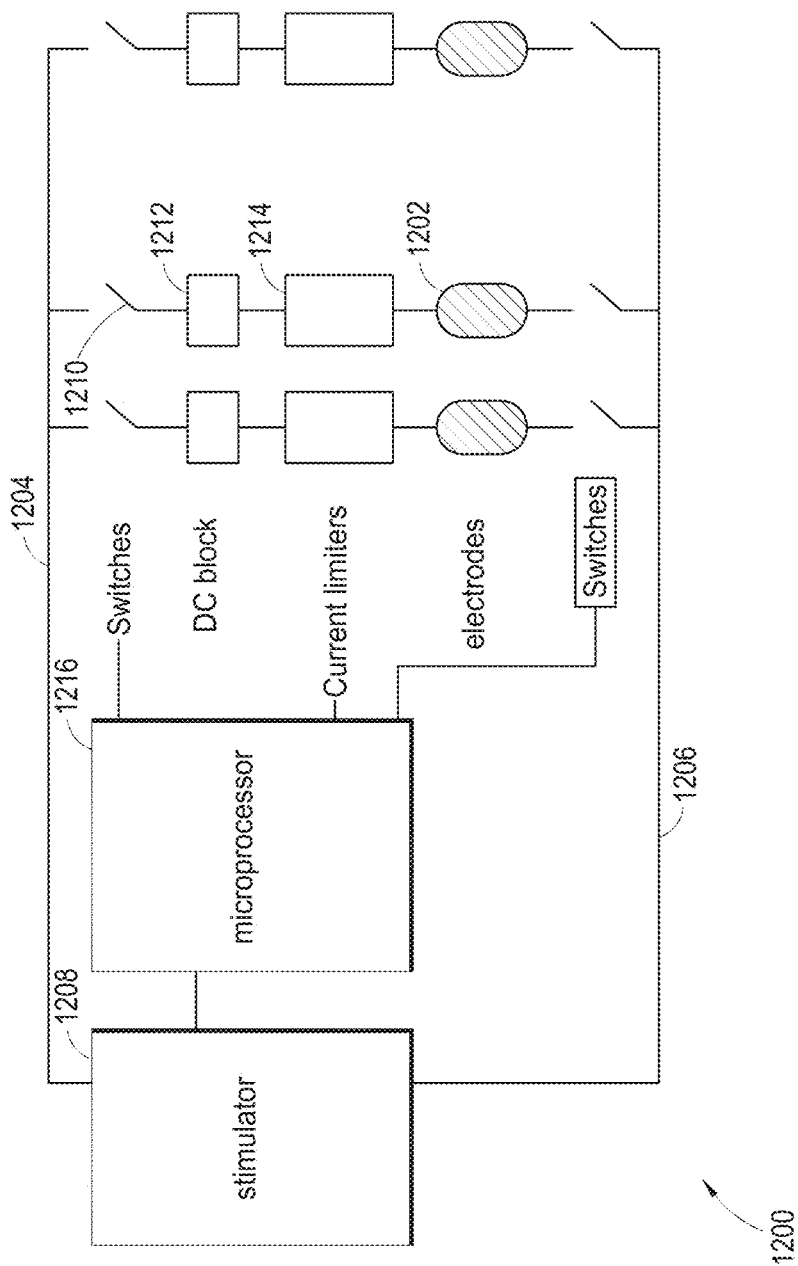

In some embodiments, stimulating three or more electrodes can be used to stimulate two or more nerves. In some embodiments as shown in FIG. 12A, the electronics and electrical circuit 1200 used to drive the array can include an adaptable switch that allows each individual electrode 1202 to be connected to either one of the two contacts 1204, 1206 of the stimulator 1208 at a given time by opening or closing switches 1210 in each channel. Each channel can include a DC blocking circuit 1212, as charge balance can be important to prevent skin irritation and burns, and also be individually current limited by current IO limiters 1214 in order to prevent current surges that could cause injury or discomfort. This current limitation can be set to a predetermined tolerability threshold for a particular patient or group of patients.

There are many transistor circuits or components like polyfuses to limit or shutdown the current to a particular node. These circuits and its components, such as the stimulator, switches, and current limiters, can be controlled and/or be programmable by a microprocessor 1216 in real-time. The 15 switch matrix allows multiple electrodes to be connected to the same stimulator contacts at a given time for maximum flexibility. In addition, electrodes can be switched between the positive and negative contacts of the stimulator to produce a bipolar pulse.

FIG. 13 shows an embodiment of a wearable band 900 with integrated electrodes 902, 904. The integrated electrodes 902, 904 can be dry electrodes in electrical communication with a detachable controller 910 through a flexible circuit embedded in the band. In some cases, dry electrodes may be more suitable for longer term use electrodes that can be used for months, such as at least 1, 2, or 3 months, before the band needs to be replaced. In some embodiments, the band may be a single use band that can be used for a relatively long period of time before replacement.

In some embodiments, disclosed herein are systems and methods for stimulating a plurality of nerves for the treatment of conditions including but not limited to overactive bladder. Stimulation of 2, 3, or more nerves, such as the saphenous and tibial nerve could be used for the treatment of conditions such as overactive bladder. Dual nerve stimulation can in some cases synergistically increase the effectiveness of therapy by combining synergistically the effects of, for example, saphenous and tibial nerve stimulation. In some embodiments, including those disclosed in connection with FIGS. 14 and 15 below, the system can be configured to independently control stimulation of a first target nerve (including stimulation parameters such as frequency and others listed herein) and a second target nerve respectively. In other words, the first target nerve and the second target nerve can be stimulated with either the same or different parameters, and can be stimulated simultaneously or in alternating or other fashion. In some embodiments, the stimulation systems can include a plurality of independent stimulation circuits, or a common circuit with a controller configured to switch stimulation parameters for one, two, or more nerves.

Figure 14:
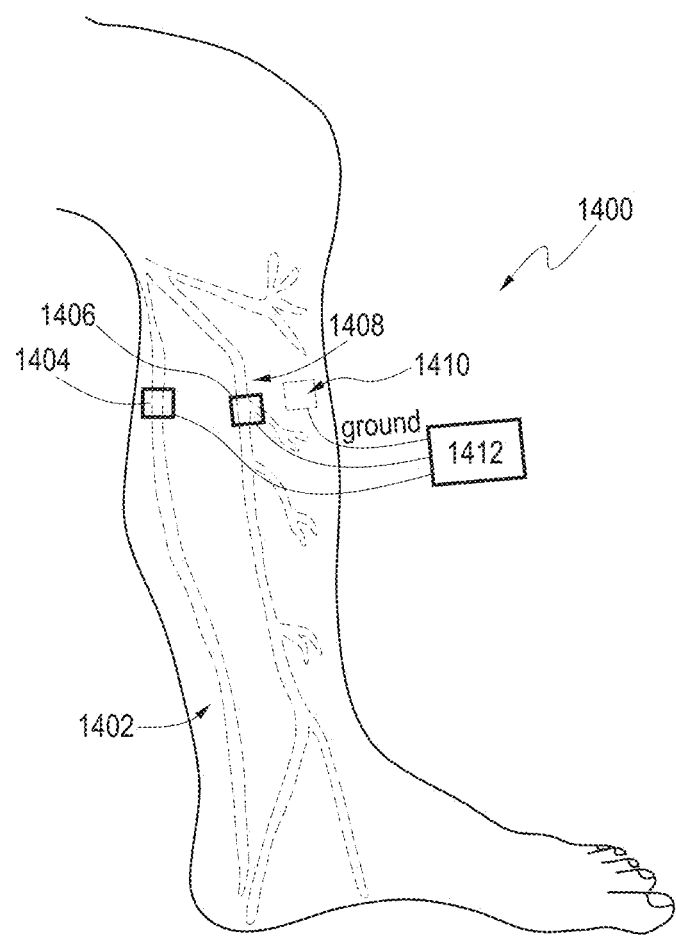
FIGS. 14 and 15 illustrate embodiments of stimulation systems with at least three electrodes that can be configured to independently stimulate a plurality of nerves.

In some embodiments, as illustrated schematically in FIG. 14, a system 1400 can utilize three electrodes: a first electrode 1404 positioned over a first nerve, e.g., the tibial nerve 1402, a second electrode 1406 positioned over a second nerve, e.g., the saphenous nerve 1408, and a third electrode 1410 positioned, for example, on the outer side of the leg, opposite to the first two electrodes 1404, 1406. This third electrode 1410 would serve as a common cathode for the other two electrodes 1404, 1406. The three electrodes 1404, 1406, 1410 can be oriented in such a way that the electric fields between each of the first two electrodes 1404, 1406 and the common cathode 1410 pass through the tibial nerve 1402 and saphenous nerve 1408, respectively.

Figure 15:
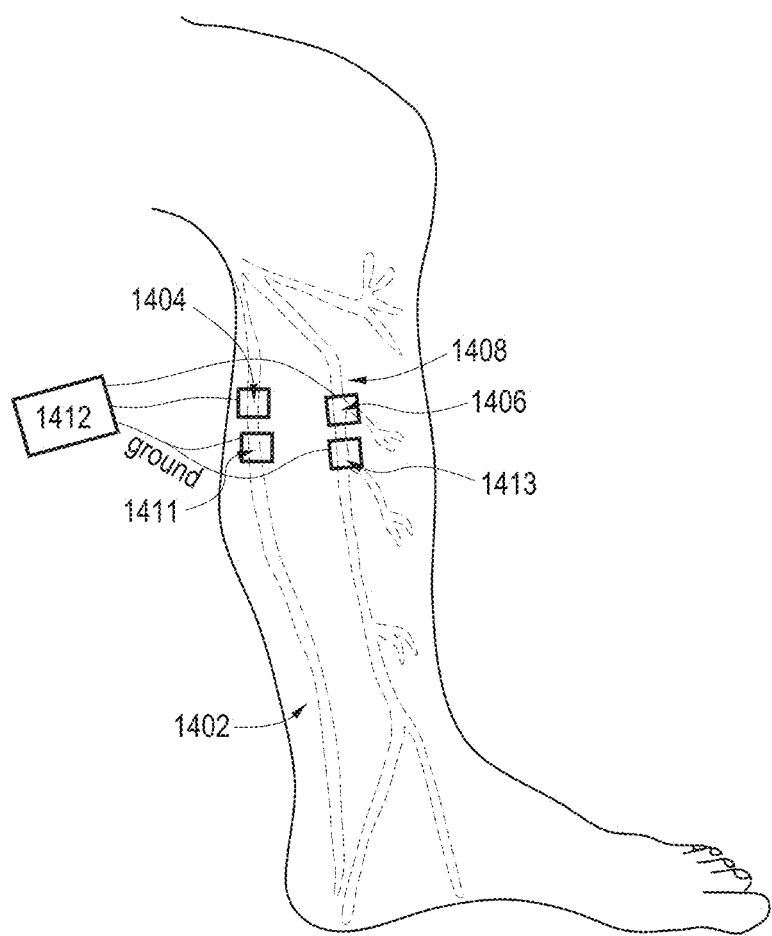

Another possible configuration shown in FIG. 15 utilizes four electrodes. Similar to the embodiment illustrated in FIG. 14, three channels are used: a first targeting the tibial nerve 1402, a second targeting the saphenous nerve 1408, and one acting as a common cathode 1410. However, the cathode in the electronics can be split between two common electrodes 1411, 1413, each serving as a cathode electrode for the other two electrodes 1404, 1406. Thus, a first electrode 1404 is positioned over the tibial nerve 1402 with a first cathode electrode 1411 positioned directly below it and a second electrode 1406 is positioned over the saphenous nerve 1408 with a second common electrode 1413 positioned directly below it. Each electrode pair 1404, 1411 and 1406, 1413 can be oriented in such a way that the electric field between the two electrodes (the electrode over the nerve and its respective common electrode) passes through the intended nerve (e.g., tibial or saphenous).

Figure 16A:
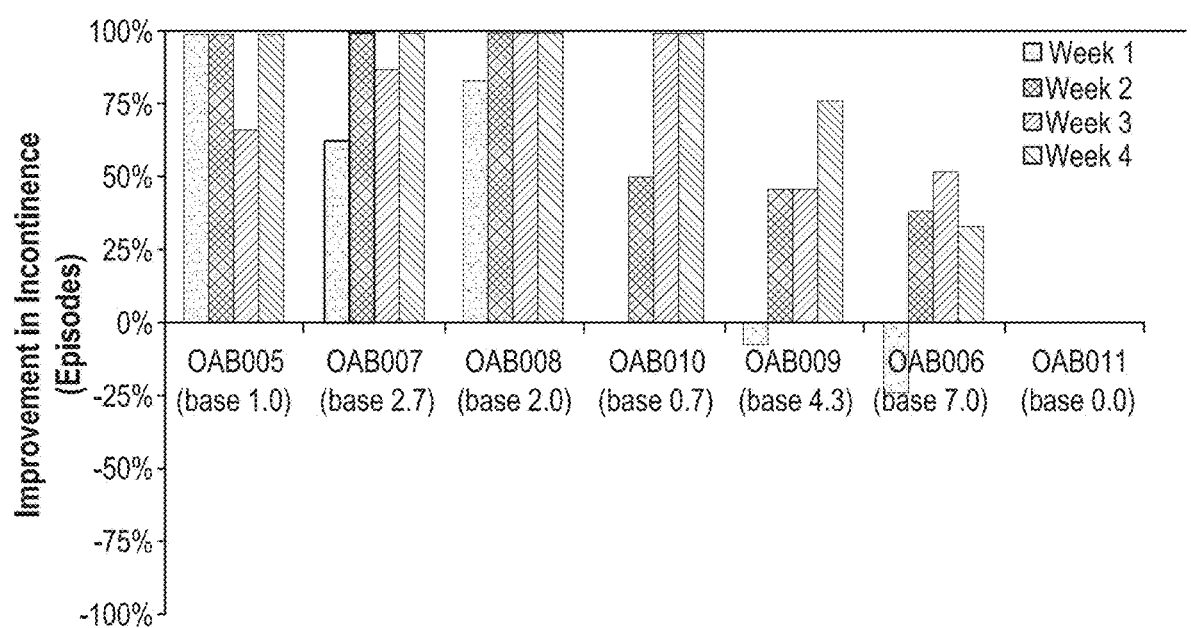
FIGS. 16A-16C illustrate clinical data relating to saphenous nerve stimulation, according to some embodiments of the invention.
Figure 16B:
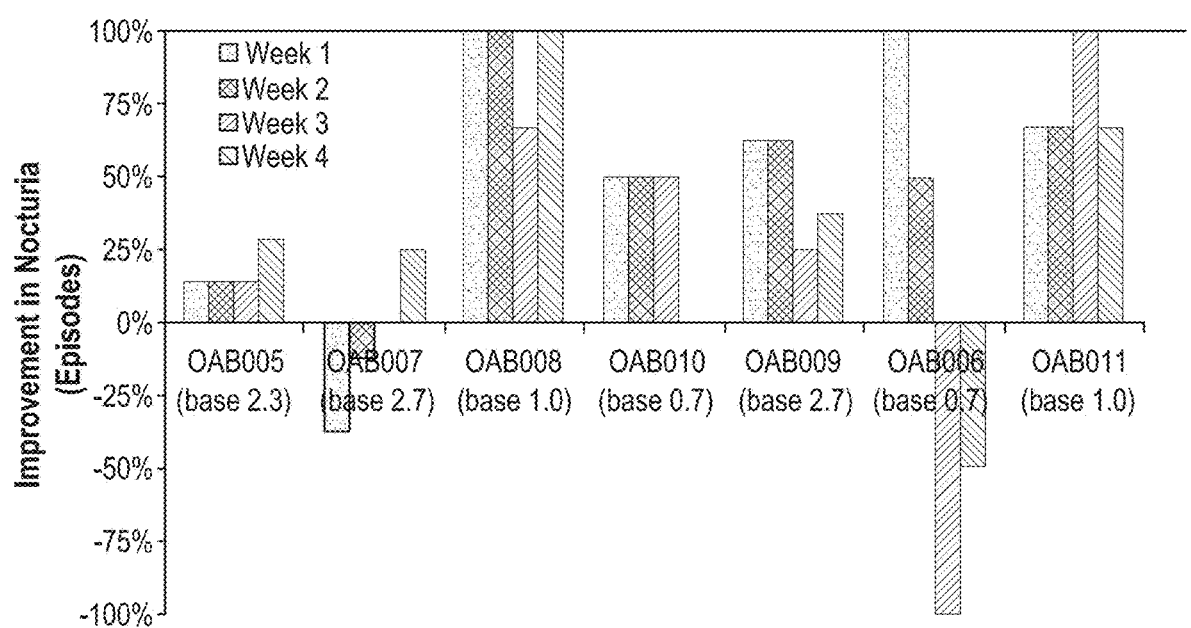
Figure 16C:
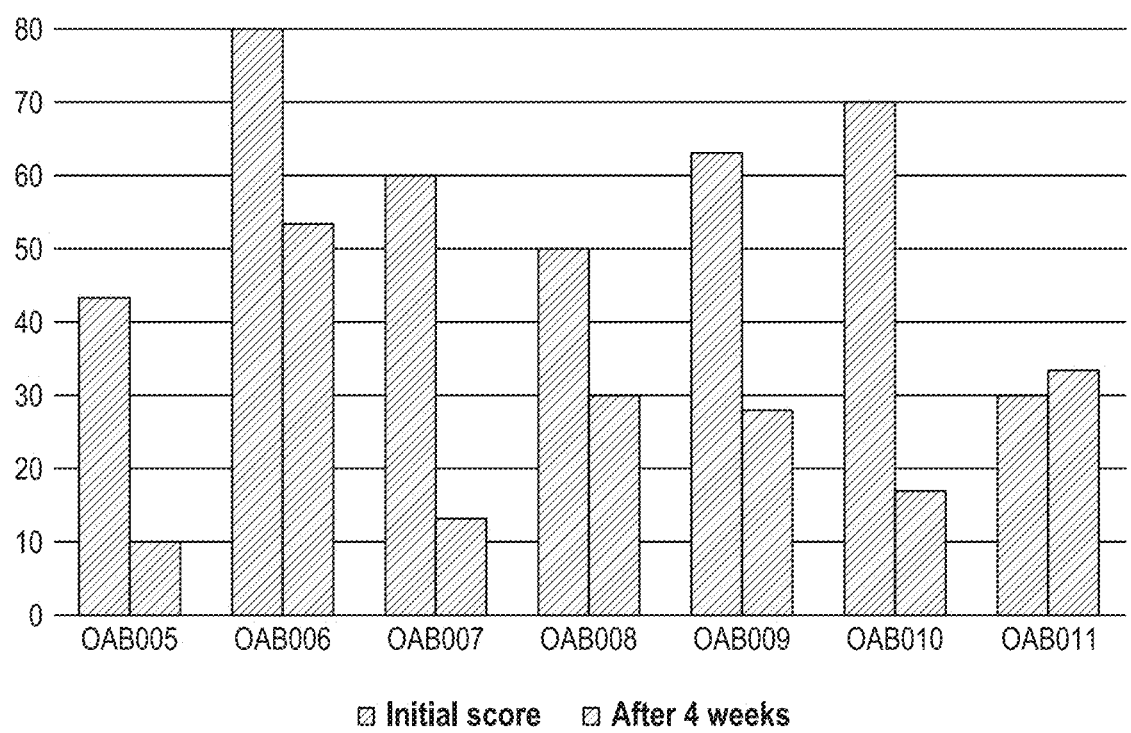

A 4 week proof of concept (POC) study of transcutaneous saphenous nerve stimulation was performed, and 7 subjects were enrolled. Eligibility was confirmed using industry-standard OAB-V8 screen and a week of baseline data. The subjects were treated with 60 minutes of daily saphenous nerve stimulation. Data collected included a weekly 3-day voiding diary, and ICIQ-SF and OAB-Q patient assessments at a 4 week appointment. The study data is shown in FIGS. 16A-16C. FIG. 16A illustrates bar graphs showing that patients responded after 1 week of daily therapy, faster than the 4 week response reported for percutaneous stimulation. All subjects improved, and 4 subjects with mild to moderate incontinence experienced near-complete alleviation of incontinence. FIG. 16B illustrates that nocturia generally improved as well. FIG. 16C shows results of the OAB-q scale, an established scale for quality of life in overactive bladder, and demonstrates clinically significant (e.g., 10 point or more) improvement in quality of life.

Figures 17C, 17D:
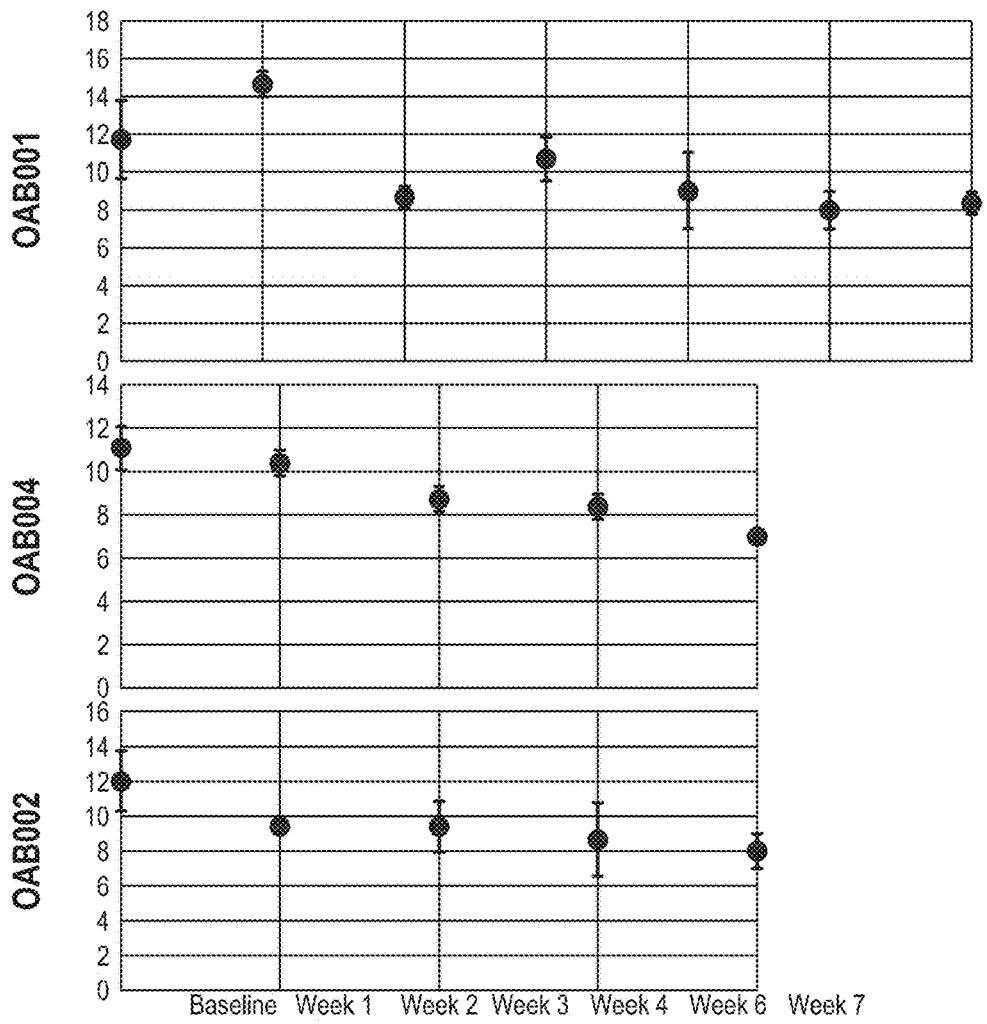
Figure 17E:
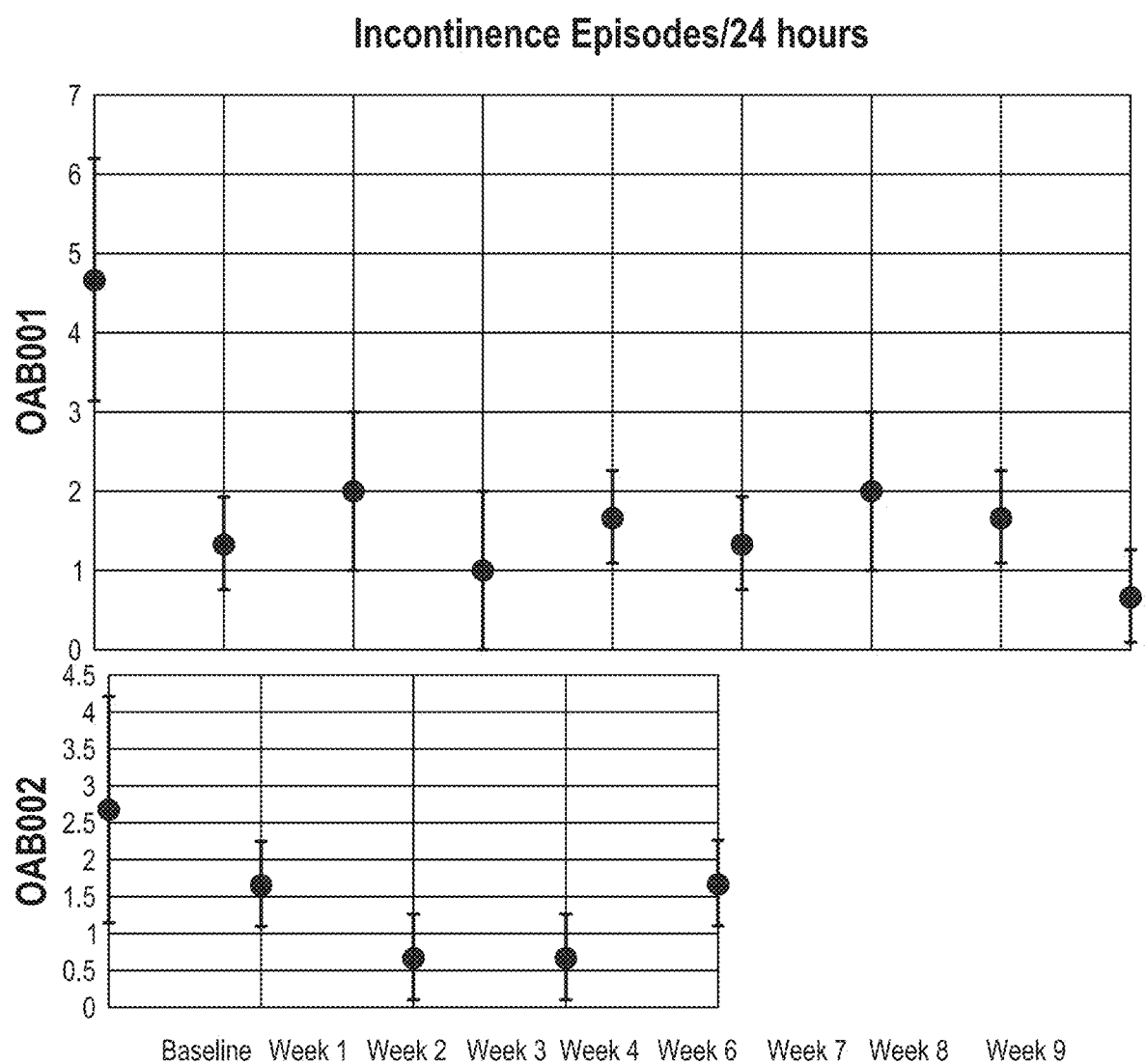
Figure 17F:
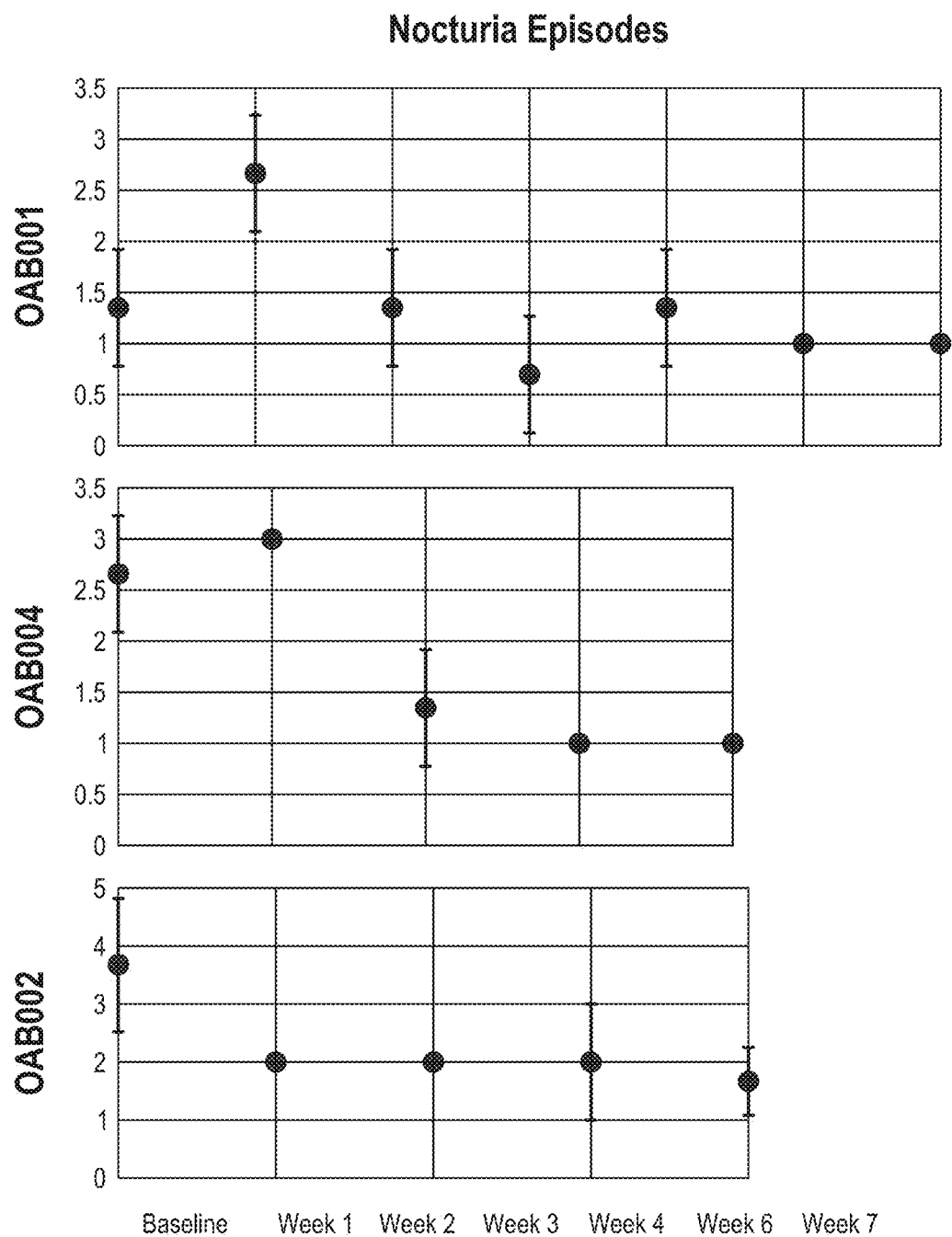

A 4 week proof of concept (POC) study of transcutaneous tibial nerve stimulation was performed, and 4 subjects were enrolled. Eligibility was confirmed using industry-standard OAB-V8 screen and a week of baseline data. The subjects were treated with 60 minutes of daily tibial nerve stimulation. Data collected included frequency, incontinence, and nocturia data. The study data is shown in FIGS. 17A-17F. FIG. 17A illustrates a table of subject baseline parameters, including OAB-V8 score, frequency, incontinence, and nocturia rates in 24 hours. FIG. 17B illustrates a table of responder rates for nocturia, incontinence, and frequency. FIG. 17C illustrates a table of improvement in urinary parameters, including frequency, incontinence, and nocturia. As illustrated in the graphs of FIGS. 17D, 17E, and 17F, urinary frequency episodes per 24 hours, incontinence episodes per 24 hours, and nocturia episodes per 24 hours generally improved with stimulation.

As noted above, HRV can have a direct relationship with sympathetic and parasympathetic activity. Not to be limited by theory, sympathetic and parasympathetic activity can be abnormal in subjects with overactive bladder, which is a dysregulation of the bladder reflex loop controlled by the autonomic nervous system. In subjects with OAB, the parasympathetic nerves (e.g., pelvic nerves) can cause the detrusor to contract due to elevated activity after voiding. This parasympathetic overactivity can cause the bladder to contract again before it is full. In subjects with OAB, sympathetic activity can be elevated when the bladder is full, leading to sensory urgency. Sympathetic overactivity can be associated with OAB without detrusor muscle overactivity, and parasympathetic overactivity can be associated with OAB with detrusor muscle overactivity.

HRV measurements in subjects with OAB can be significantly different during bladder filling and voiding compared to controls. Through frequency-domain analysis, heartbeat frequencies can be separated into distinct bands. High-frequency signals (between about 0.15 Hz and about 0.4 Hz) can almost exclusively reflect parasympathetic activity, and low-frequency signals (between about 0.04 Hz and about 0.15 Hz) can represent a mixture of sympathetic and parasympathetic activity. In some embodiments, taking the ratio of high frequency (HF) to low frequency (LF) signals yields an approximation of one's sympathetic tone. Very low frequency (VLF) signals (between about 0.004 Hz and about 0.040 Hz) can also be evaluated to assess parasympathetic activity. The total power of HRV in the frequency domain can also be evaluated to assess autonomic activity.

Sympathetic and parasympathetic functions can also be evaluated, for example, by analyzing mean normal-to-normal intervals, e.g., all intervals between adjacent QRS complexes of measured cardiac rhythm, including the number of interval differences of successive NN intervals greater than 50 milliseconds; square root of the mean squared differences of successive NN intervals, and standard deviation of the NN intervals.

In some embodiments, sympathetic activity can also be assessed using more traditional techniques, such as measuring blood pressure changes before release and before starting a hand grip exercise, or measuring blood pressure changes before and after immersing the hand in a bath of cold water (e.g., cold pressor test). Parasympathetic activity can be assessed by measuring heart rate response during deep breathing, or heart rate response to standing from lying or seated position (orthostatics). Both sympathetic and parasympathetic activity can be assessed during the Valsalva maneuver (e.g., blowing into a mercury manometer and maintaining a pressure of about or at least about 40 mmHg), or orthostatic heart rate response (e.g., to standing from lying or seated position).

Additional specific examples of methodologies that can treat a disorder relating to bladder dysfunction by restoring balance to sympathetic and parasympathetic nervous system activity, including but not limited to reducing sympathetic and/or parasympathetic nervous system activation relating to neural bladder circuits, are disclosed herein.

Figure 17G:
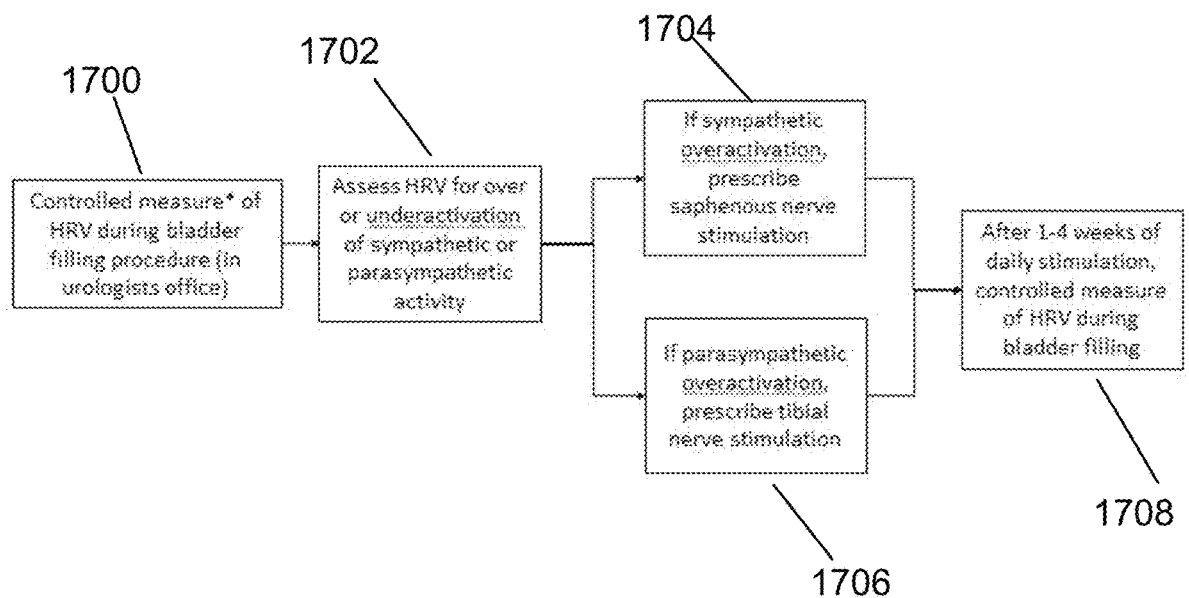
FIGS. 17G-17I illustrate flow charts relating to therapeutic methods involving stimulation for treating bladder disorders, according to some embodiments of the invention.

FIG. 17G illustrates a flow chart of an example of a therapeutic protocol for treating OAB or another bladder disorder, according to some embodiments of the invention. In some embodiments, sympathetic and parasympathetic activity can be assessed during a bladder filling cycle using sensors that measure heart rate and heart rate variability (box 1700). The controlled measurement could be using urodynamic cystography or a procedure where the subject voids, then consumes fluid at a specific rate until voiding is necessary. Heart rate and HRV can be measured in various ways, including an optical sensor in a wrist worn device, a chest strap or patch that measures changes in electrical activity, a pulse oximeter worn on the finger, and the like (box 1702). Sympathetic and parasympathetic activity can also be measured using electrodermal activity sensors as described elsewhere herein. In some embodiments, a single device can include both an optical heart rate sensor and electrodermal activity sensors to improve the estimation of sympathetic and parasympathetic activity. If sympathetic overactivation is identified (e.g., from HRV and/or other autonomic measurements), saphenous nerve stimulation can be initiated (e.g., saphenous nerve stimulation alone without tibial nerve stimulation)(box 1704). If parasympathetic overactivation is identified, tibial nerve stimulation can be initiated (e.g., tibial nerve stimulation alone without saphenous nerve stimulation)(box 1706). After a period of stimulation, such as daily after 1-4 weeks of stimulation for example, another controlled measure of autonomic bladder function (e.g., controlled measure of HRV during bladder filling) can be performed (box 1708).

Figure 17H:
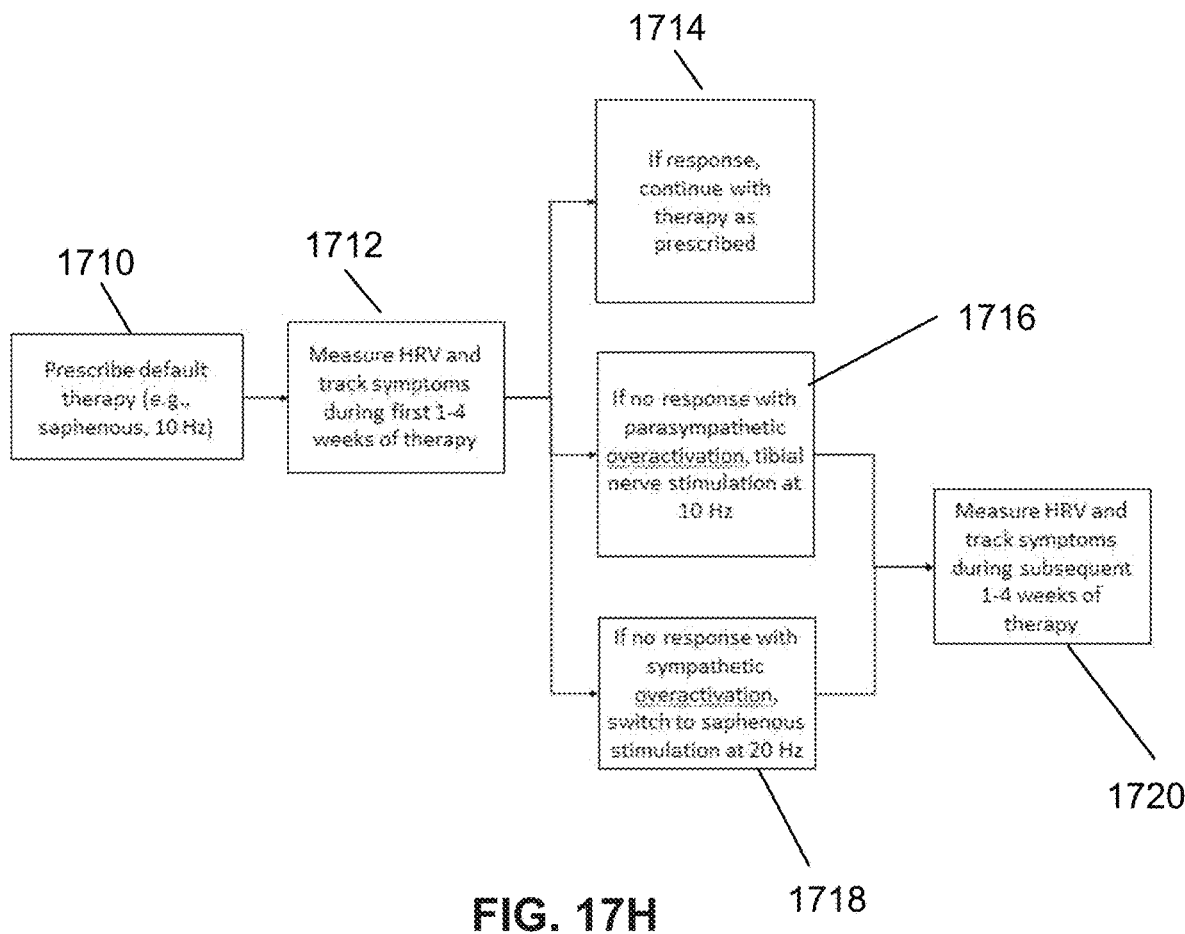
Figure 17I:
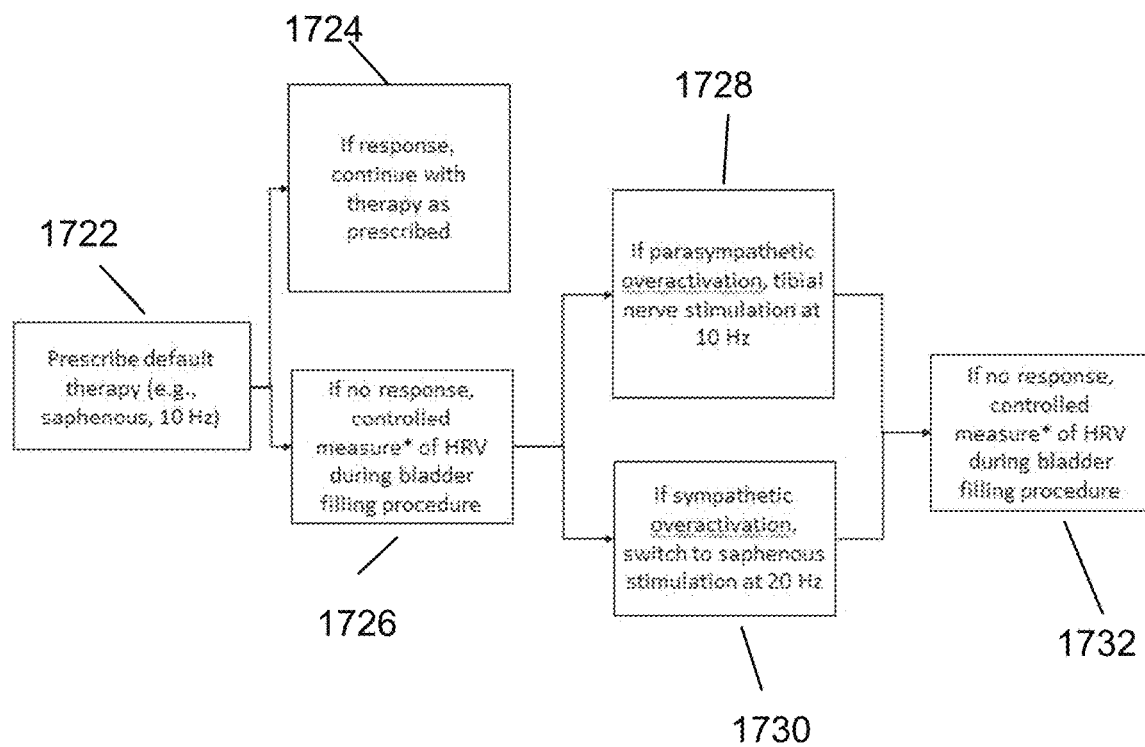

In some embodiments, sympathetic and parasympathetic activity are assessed prior to initial stimulation to select specific nerve targets, stimulation waveforms, stimulator parameters, or dosing of stimulation (e.g., time of day, duration of stimulation, number of times per day or week). In other embodiments, a default stimulation is applied in a trial fashion, and only if a person does not respond to treatment is sympathetic and parasympathetic activity assessed, as illustrated in FIG. 17H and FIG. 17I. As shown in a non-limiting flow chart algorithm of FIG. 17H, a default therapy can be prescribed, e.g., saphenous stimulation at 10 Hz (box 1710). HRV and symptoms can be tracked during the first 1-4 weeks of therapy (box 1712). If an appropriate response to therapy is achieved, therapy can be continued as prescribed (box 1714). If there is no response or an insufficient response to therapy and parasympathetic overactivation is found, the initial therapy could be discontinued, and/or tibial nerve stimulation at 10 Hz for example could be added (box 1716). If there is no response to therapy and sympathetic overactivation is found, therapy can be changed to saphenous nerve stimulation at a different frequency (e.g., 20 Hz)(box 1718). HRV and symptoms can be tracked during the subsequent 1-4 weeks of therapy (box 1720). As shown in another non-limiting flow chart algorithm of FIG. 17I, a default therapy can be prescribed, e.g., saphenous stimulation at 10 Hz (box 1722). If an appropriate response to therapy is achieved, therapy can be continued as prescribed (box 1724). If there is no response to therapy or an insufficient response, a controlled measure of HRV can be performed during a bladder filling procedure (box 1726). If parasympathetic overactivation is found, the initial therapy could be discontinued, and/or tibial nerve stimulation at 10 Hz for example could be added (box 1728). If there is no response to therapy and sympathetic overactivation is found, therapy can be changed to saphenous nerve stimulation at a different frequency (e.g., 20 Hz)(box 1730). If there continues to be no response or an insufficient response to therapy, a controlled measure of HRV can be performed during a bladder filling procedure (box 1732). In some embodiments, sympathetic and parasympathetic activity are assessed over a single day or over multiple days during an initial period of treatment to measure any changes in autonomic activity. In some embodiments, bladder symptoms may be tracked by the patient, either manually or on paper, onboard the stimulation device, or on an external computing device such as a smartphone, tablet, laptop, etc. to be correlated with parameters, such as HRV and changes in autonomic activity, for example.

In some embodiments, if a person does not respond to therapy, a number of parameters can be altered to modify therapy, including but not limited to increasing or decreasing, or otherwise changing any number of the following: duration of session (e.g., 20-120 minutes); number of sessions per day or week (e.g., 2 times per day to 3 times per week); time of day or night of stimulation; stimulation frequency; bursting or other stimulation pattern (including bursting frequency); nerve target (e.g., saphenous or tibial); and/or stimulation amplitude.

Figure 17J:
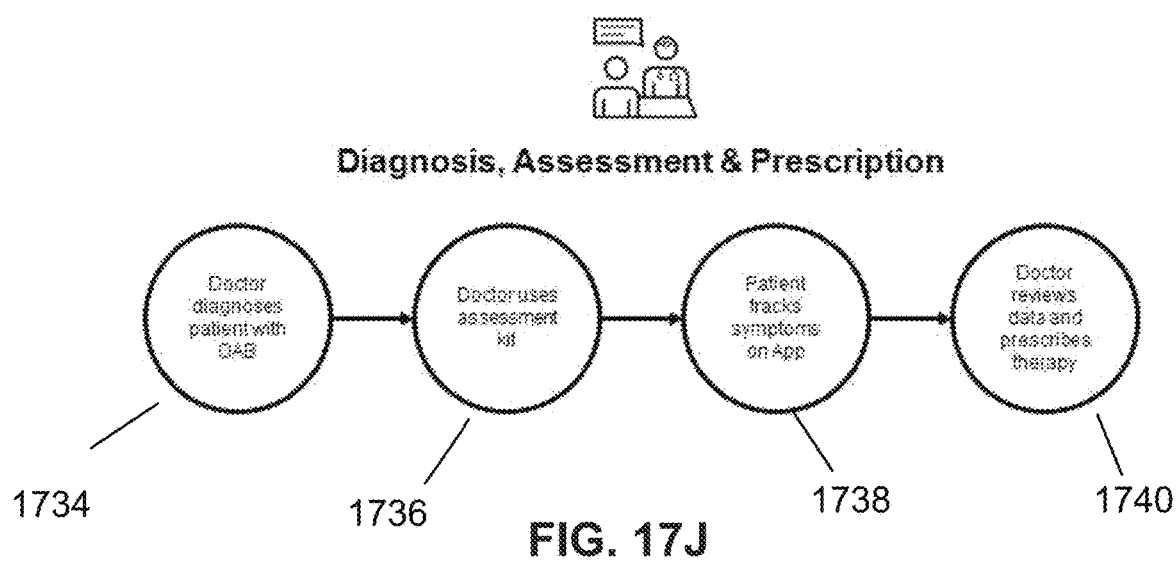
FIGS. 17J-17K illustrate flow charts and diagrams relating to diagnosis, assessment, and prescription of an overactive bladder therapy, according to some embodiments of the invention.
Figure 17K:
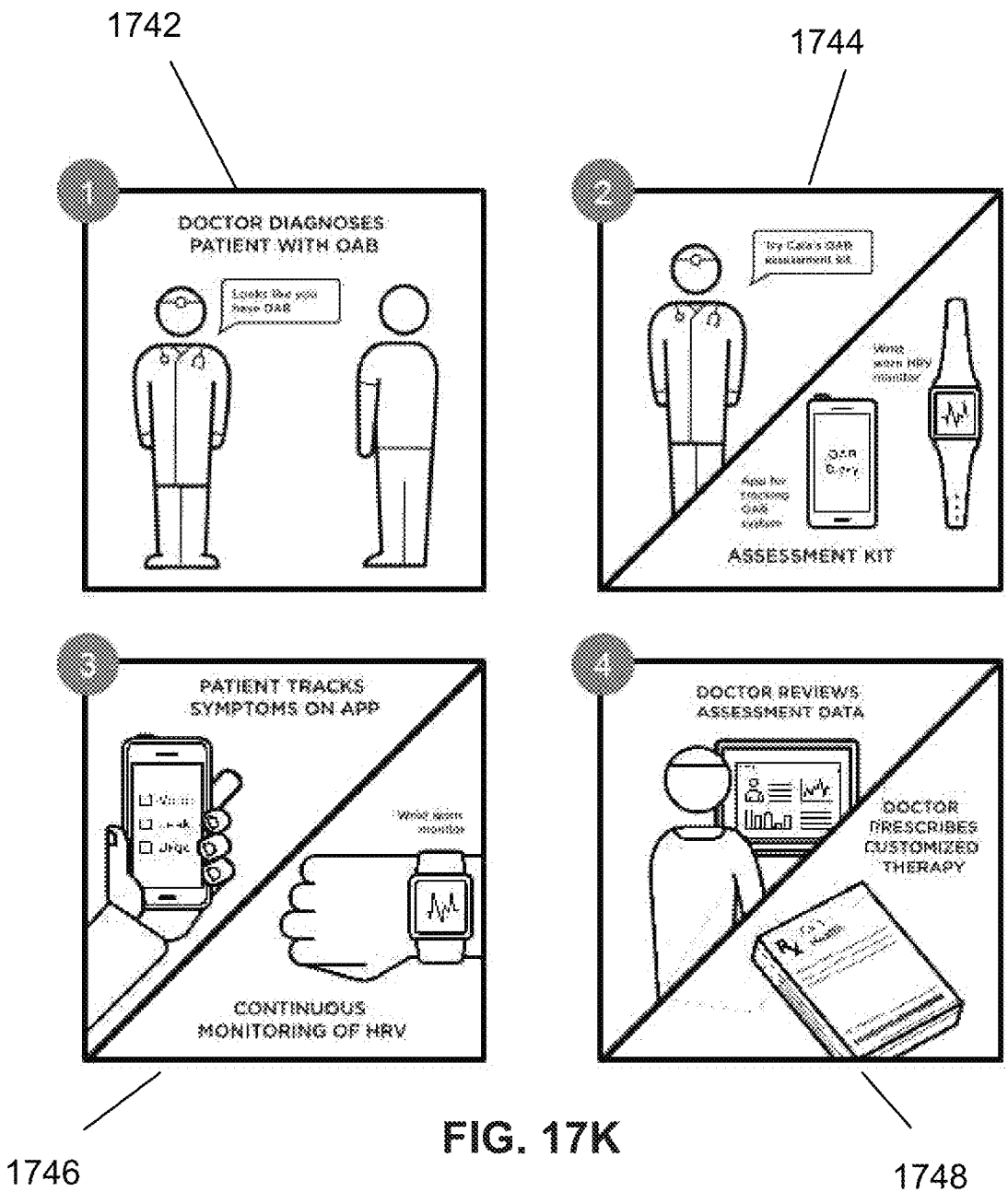

FIGS. 17J-17K schematically illustrates a diagnosis, assessment, and prescription flow chart for a subject with OAB, according to some embodiments of the invention. A physician can diagnose a subject with OAB (box 1734, 1742), and then utilize an assessment kit (box 1736, 1744), which can include an autonomic nervous system activity monitoring device, such as a continuous or intermittent wrist-worn HRV monitor for example, and an application for tracking bladder function, that can include symptom and voiding diaries, fluid intake, and other functionality entered by the patient (box 1738, 1746). The physician can review the assessment data and prescribe customized therapy based on the assessment data (box 1740, 1748).

Figure 17L:
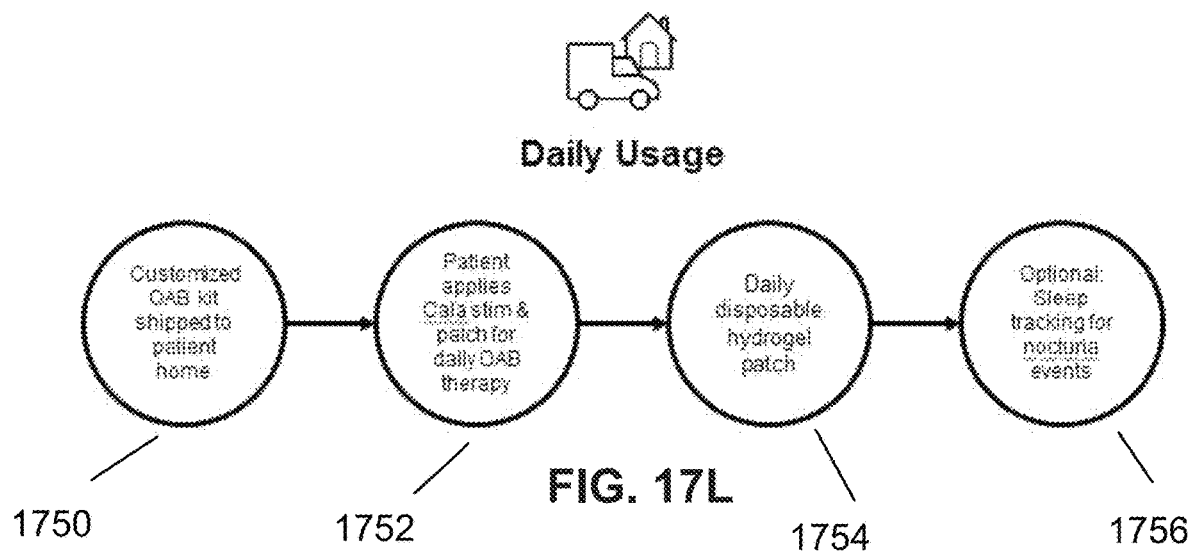
FIGS. 17L-17M illustrate flow charts and diagrams relating to usage of a customized overactive bladder treatment kit by a subject, according to some embodiments of the invention.
Figure 17M:
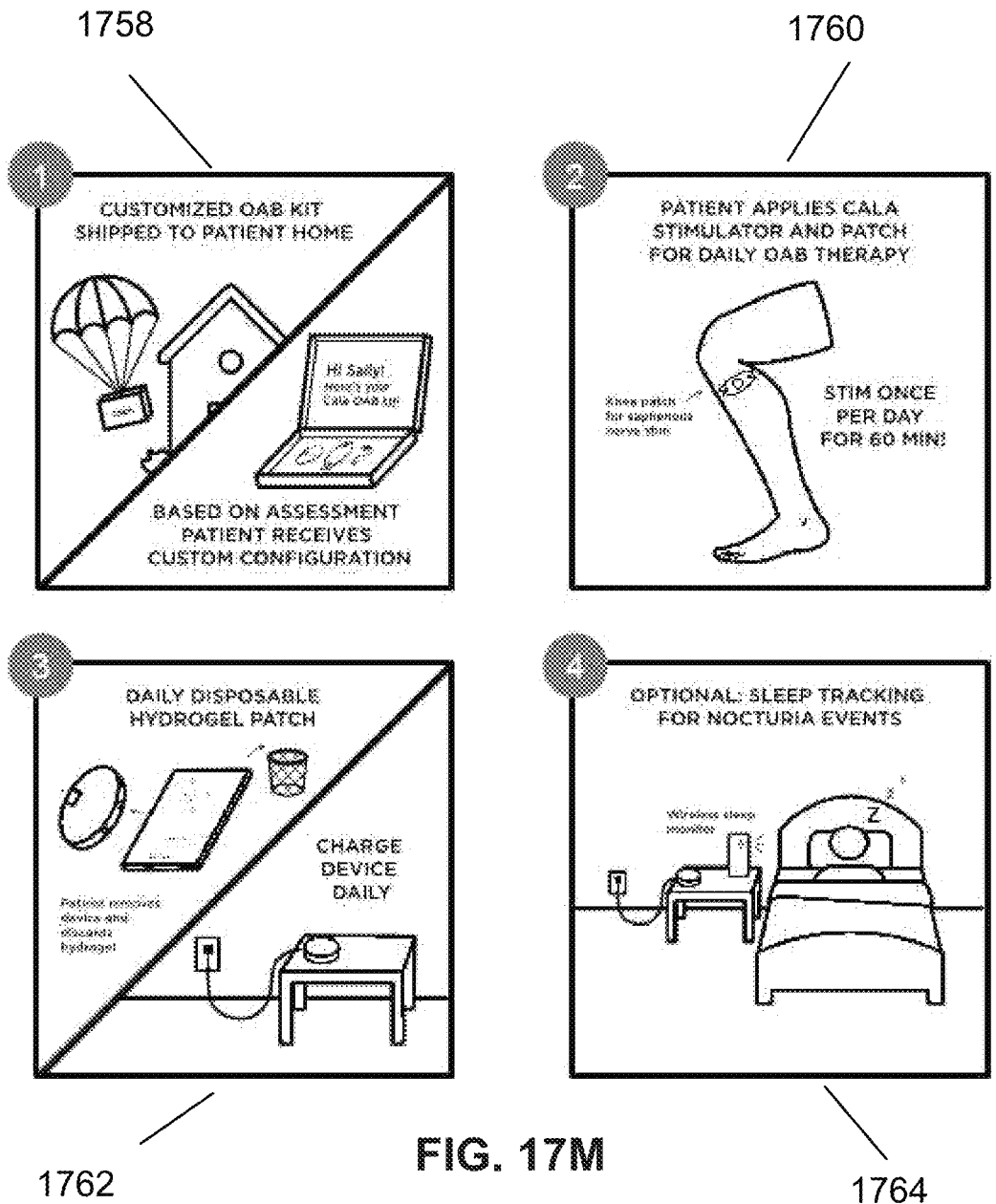

FIGS. 17L-17M schematically illustrate a flow chart for daily usage of a subject with OAB, according to some embodiments of the invention. A customized therapy kit can be shipped to a subject, such as based on information received from the flow chart in FIGS. 17J-17K for example (box 1750, 1758). The patient can apply a wearable stimulation device which can include a patch for periodic, e.g., daily, therapy (box 1752, 1760). The stimulation device can include one, two, or more daily disposable hydrogel or other patches (box 1754, 1762), and can have a power source, such as a battery that the user can charge periodically. In some embodiments, the system can include a sleep tracking device, such as a wireless sleep monitor, for example for tracking nocturia events (box 1756, 1764).

In some embodiments, disclosed herein are wearable systems and methods that can utilize transcutaneous sensory stimulation in the form of a burst pattern, e.g., a theta burst pattern to improve the symptoms of overactive bladder and a variety of other conditions, including but not limited to those disclosed herein. Noninvasive peripheral nerve theta burst stimulation may be effective in driving cortical or spinal plasticity to reduce symptoms and improve an individual's quality of life.

In some embodiments, the stimulation involves patterns of electromagnetic stimulation of peripheral nerves. The patterned stimulation could be a bursting stimulation, such as an on/off pattern that repeats at regular intervals (e.g., on for 10 ms, off for 20 ms, etc.), or non-burst patterned stimulation that can be more complex in some embodiments, such as a stochastic pattern or a sinusoidal envelope for example. The electromagnetic stimulation could include, for example, electrical energy, mechanical energy (e.g., vibration), magnetic energy, ultrasound energy, radiofrequency energy, thermal energy, light energy (such as infrared or ultraviolet energy for example), and/or microwave energy, or combinations thereof. In some embodiments, the stimulation is limited to only electrical energy (e.g., no magnetic or other types of energy are applied). The peripheral stimulation could include transcutaneous, percutaneous, and/or implanted stimulation.

In some embodiments, the stimulation involves noninvasive transcutaneous electrical patterned or burst stimulation of peripheral nerves, including afferent and/or efferent nerves. Not to be limited by theory, but burst stimulation of peripheral nerves can unexpectedly result in one or more of the following compared with conventional or continuous stimulation: greater efficacy; greater plasticity; increased tolerance or tolerability; reduced effects of habituation; increased comfort; and/or reduced treatment time required to achieve the same beneficial effects. Burst stimulation of peripheral nerves, including afferent nerves, can in some cases deliver a more efficacious therapy by remotely accelerating plasticity of one or more central nervous system (e.g., brain and/or spinal cord) circuits, in other words creating plasticity in neural circuits for a period of time that is far longer than the duration of the stimulation session, such as, for example, about or at least about 6 hours, 12 hours, 24 hours, 2 days, 3 days, 4 days, 5 days, 6 days, 7 days, 2 weeks, 3 weeks, 1 month, 2 months, 3 months, 4 months, 5 months, 6 months, 9 months, 12 months, 18 months, 24 months, 36 months, or even longer. Peripheral stimulation in some cases can be more convenient and comfortable for the user than central stimulation (e.g., transcranial stimulation and/or spinal stimulation) and can be more suitable for home and ambulatory use.

In some embodiments, the burst stimulation includes theta burst stimulation. Theta burst stimulation (TBS) is a patterned form of repetitive stimulation that uses high frequency pulses separated by varying inter-burst intervals. Originally used for the induction of long term potentiation in hippocampal learning and memory research, theta burst stimulation in the form of repetitive magnetic stimulation (rTMS) has been demonstrated to noninvasively induce plasticity in humans in the motor, sensory and visual cortex. Depending on various parameters including the duration and continuity of stimulation, a long term potentiation or depression (LTP/LTD) like effect can be observed which are surrogate measures of synaptic efficacy. The number of sessions and the spacing interval between individual sessions of stimulation can also have an effect on the duration of the induced response. The level of muscle relaxation before or during stimulation can also affect the resulting direction or amplitude of plasticity induction suggesting that homeostatic mechanisms are in place that adjust the threshold for plasticity depending on prior synaptic activity. The effective modulation of nervous system plasticity demonstrated with theta burst stimulation can have great potential for the treatment of various neurologic disorders, and can have an effect on other central neural circuits.

Figure 18A:
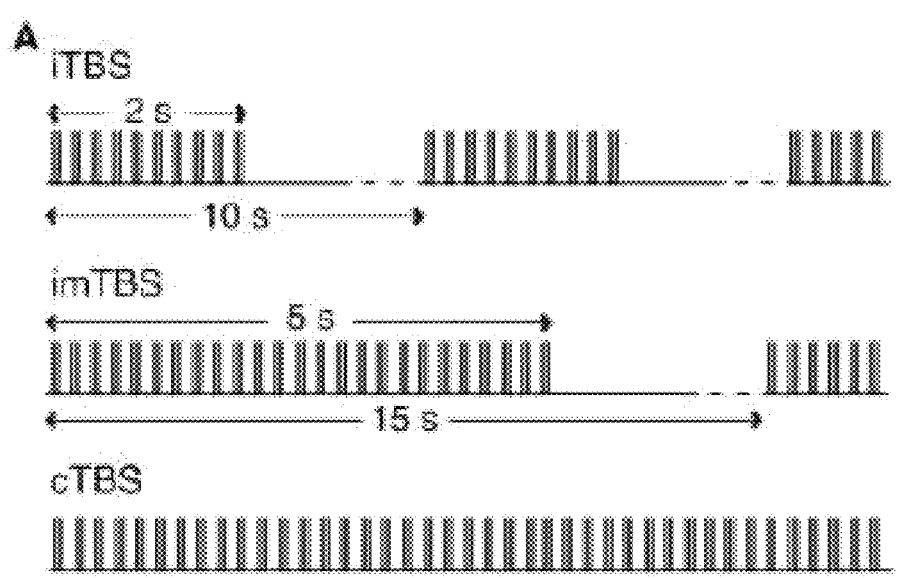
FIG. 18A illustrates non-limiting examples of intermittent theta burst stimulation (iTBS), continuous theta burst stimulation (cTBS), and intermediate theta burst stimulation (imTBS).

In some embodiments, theta burst stimulation can take the form of intermittent theta burst stimulation (iTBS), continuous theta burst stimulation (cTBS), and intermediate theta burst stimulation (imTBS). Non-limiting examples of iTBS, cTBS, and imTBS are illustrated in FIG. 18A. Each illustrate examples of TBS including a burst of 3 stimuli at 50 Hz (20 ms between each stimulus) which was repeated at inter-burst intervals of 200 ms (5 Hz). In the iTBS example pattern, an about 2 second train of TBS is repeated about every 10 seconds for a total of 190 seconds (600 pulses). In the imTBS example pattern, an about 10 second train of TBS is repeated every 15 seconds for a total of 11 seconds (600 pulses). In the cTBS pattern, a 40 second train of uninterrupted TBS is given (600 pulses). The burst pattern (or a combination of two or more burst patterns) can be selected depending on the desired clinical result. In some cases, cTBS can be inhibitory, iTBS can be excitatory, and imTBS can be neither excitatory nor inhibitory, but this may be varied depending on the parameters. In some embodiments, inhibitory stimulation of a first nerve (e.g., the saphenous or tibial nerves) can be used alone or in combination with excitatory stimulation of a second nerve (e.g., the saphenous or tibial nerves), such as to restore or improve sympathetic and parasympathetic balance. In some embodiments, inhibitory or excitatory stimulation of a nerve can be controlled by adjusting frequency or pulse width of the stimulation waveform.

In some embodiments, each burst can include a plurality of stimuli, such as about or at least about 2, 3, 4, 5, 6, 7, 8, 9, 10, 11, 12, 13, 14, 15, 16, 17, 18, 19, 20, 30, 40, 50, 60, 70, 80, 90, 100, or more stimuli. Each burst can have the same, or a variable number of stimuli.

In some embodiments, the intraburst frequency could be about or at least about 10 Hz, 20 Hz, 30 Hz, 40 Hz, 50 Hz, 100 Hz, 250 Hz, 500 Hz, 1 kHz, or more. In some embodiments, intraburst frequency could vary between about 10 Hz and about 20 kHz. Intraburst frequency can also be varied in a random or pseudorandom fashion during the burst to reduce habituation and/or increase comfort. In other embodiments, the intraburst frequency can be between about 10 Hz and about 250 Hz, between about 50 Hz and about 150 Hz, between about 10 Hz and about 100 Hz, between about 100 Hz and about 150 Hz, between about 50 Hz and about 250 Hz, or between about 50 Hz to about 1000 Hz, in order to maximize tremor reduction, improve comfort, reduce habituation, and/or reduce power consumption of the electrical stimulator device.

In some embodiments, the interburst frequency can be between about 1 Hz to about 20 Hz, such as between about 4 Hz (250 ms between the start of each burst) and about 12 Hz (83 ms), such as between about 4 Hz (250 ms) and about 8 Hz (142 ms) which is generally accepted as the theta band frequency, including about 5 Hz (200 ms), or in some embodiments between about 3.5 Hz and about 7.5 Hz, or between about 6 Hz and about 10 Hz.

In some embodiments, the inter-session frequency can be between about 1 minute and about 12 hours, such as between about 5 minutes and about 120 minutes, between about 5 minutes and about 60 minutes, between about 10 minutes and about 30 minutes, about 5, 10, 15, 20, 25, 30, 35, 40, 45, 50, 55, 60, 75, 90, 120, 180, 240, 300, 360, 420, 480, 540, 600, 660, or 720 minutes, or ranges incorporating any two of the aforementioned values.

In some embodiments, a repetitive patterned stimulation known as quadripulse stimulation could be used, which includes four pulses at a short interval frequency (interstimulus interval of 1.5 ms) repeated at about 0.2 Hz for a period of time, such as about 30 minutes. Quadripulse stimulation has been shown to induce prolonged plasticity. Variation of the intraburst frequency using this paradigm can influence the direction of induced plasticity. These repetitive small pulses could be anywhere between 2-10 pulses or more.

Other burst patterns other than theta burst stimulation can also be used, instead or in addition. Some non-limiting examples include delta (0-4 Hz), alpha (8-12 Hz), beta (12-30 Hz), and gamma (30-100 Hz) inter-burst frequencies. In some embodiments, peripheral burst stimulation can include a sinusoidal, square, rectangular, triangular, sawtooth, or other waveform.

In some embodiments, burst transcutaneous peripheral electrical stimulation can be preferred in some cases over burst transcutaneous peripheral magnetic stimulation. In some cases transcutaneous peripheral electrical stimulation can be advantageous because magnetic theta burst can require more power and/or be a heavier device. Electrical stimulation can advantageously provide ambulatory home use, and a more precise stimulation of targeted nerves by controlling flow of current between electrodes or by using a percutaneous needle. In some embodiments, stimulation can be provided at a fixed bursting frequency without measuring for/adjusting for a measured frequency of a physiologic or pathologic parameter or symptom associated with a subject.

Figure 18B:
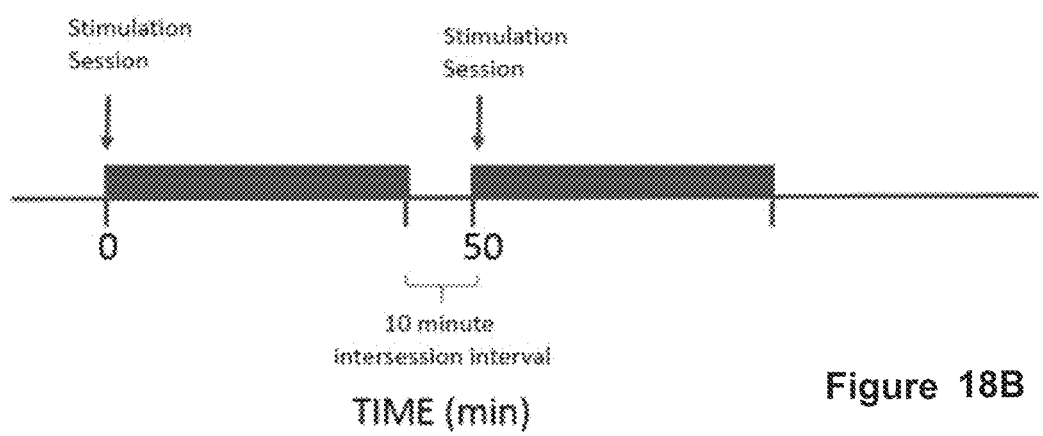
FIGS. 18B and 18C illustrate two potential non-limiting variations in timing of stimulations sessions that vary intersession interval.
Figure 18C:
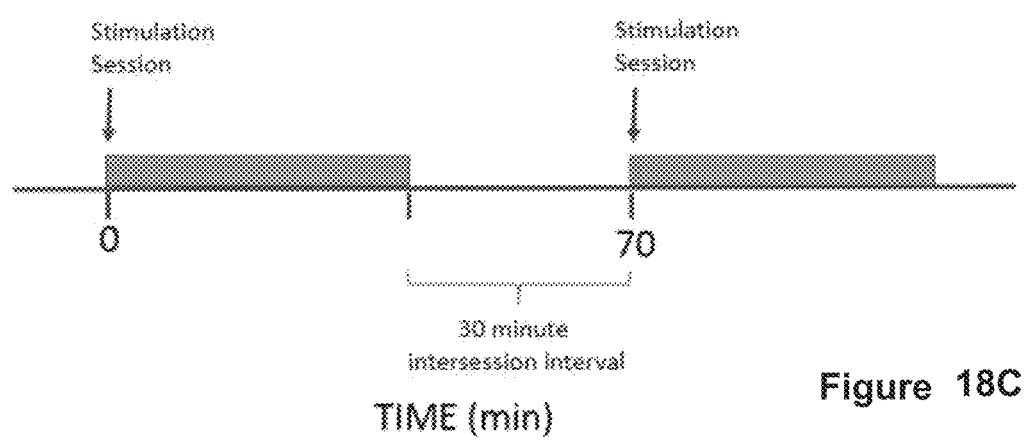

In one embodiment, the timing of individual sessions of stimulation can be varied in order to prolong the duration of plasticity, as illustrated in FIGS. 18B and 18C. The intersession interval could be between a lower threshold of approximately 1 minute and an upper threshold of approximately 24 hours. Theta burst stimulation intersession interval variation can have a significant effect of varying the spacing intervals between stimulation sessions. Prolongation of the duration of symptom improvement may improve the tolerability of chronic repetitive stimulation. In some embodiments, the intersession interval can be randomized between a lower threshold and an upper threshold. In some embodiments, the intersession interval can increase from a lower threshold or value to an upper threshold or value. In some embodiments, the intersession interval can decrease from an upper threshold or value to a lower threshold or value. In some embodiments, the intersession interval can be varied according to a predetermined algorithm or schedule. In some embodiments, the intersession interval can be varied based on feedback based on data from an accelerometer or electromyography. In some embodiments, the intersession interval can be varied based upon feedback based on tracking symptoms and/or measures of autonomic activity (e.g., HRV, EDA). The interval could also be optimized using machine learning algorithms, such as deep learning, naïve Bayesian networks, neural networks, and/or crowdsourced or otherwise aggregated datasets from multiple users with data (e.g., device usage, symptom tracking, autonomic activity) stored on a remote centralized server (e.g., the cloud).

Figure 19:
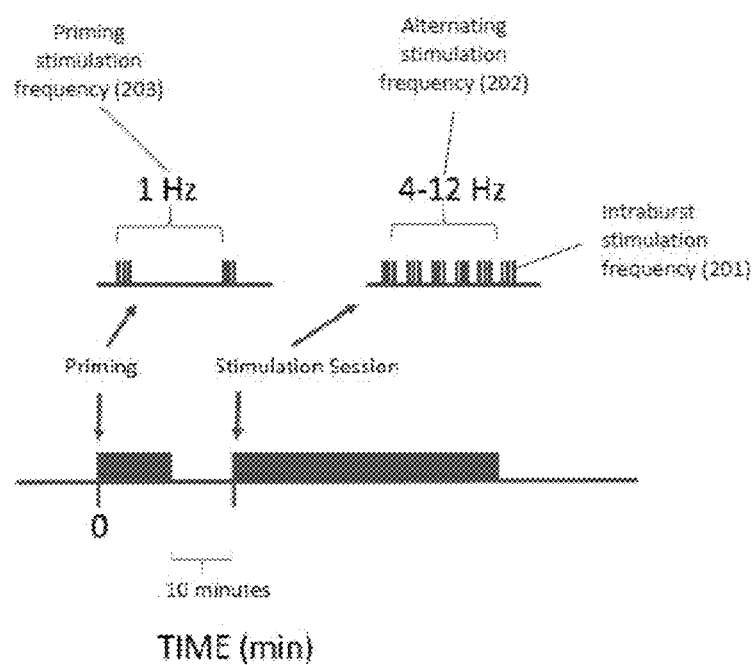
FIG. 19 illustrates an embodiment of a priming stimulation session applied just prior to the theta burst stimulation or other peripheral nerve stimulation paradigm to induce plastic effects in the central nervous system. This illustration is of a single example of a priming stimulation session, as the priming protocol may vary in intensity (e.g., stimulation amplitude), stimulation frequency, duration of stimulation, and duration interval between the priming session and stimulation session.

The effects of an individual stimulation session may be modulated by a priming stimulation session, an example of which is illustrated in FIG. 19. Prior history of synaptic activity may influence the response to a plasticity inducing paradigm according to the Bienenstock-Cooper-Munro (BCM) theory. A priming protocol may vary stimulation waveform parameters, including intensity (e.g., stimulation amplitude), stimulation frequency, duration of stimulation, and/or duration interval between the priming session and stimulation session with subsequent variation in the effects on a subsequent theta burst stimulation session. Waveform parameters may be varied in such a way that are comfortable or increase comfort, as previously described in U.S. Application No. 62/208,965. Repetitive peripheral nerve stimulation at fixed frequencies may have effects on neural circuit excitability (e.g., motor cortical or spinal reflex circuits) depending on whether the frequency is low (3-10 Hz) or higher (50-200 Hz or more). Depending on the desired effect on brain excitability with burst stimulation, e.g., theta burst, an initial priming session using, e.g., fixed frequency stimulation may allow for controlling the direction or level of plastic effects. In some embodiments, each stimulation session may be preceded by a priming session. In some embodiments, the priming sessions may precede only some but not all of the stimulation sessions, such as every other stimulation session. In some embodiments, the priming session may be delivered based on feedback from a sensor, such as an accelerometer, gyroscope, electromyography, HRV monitor, or EDA sensor. For instance, duration of the priming sessions may increase if the amount of sympathetic activity measured by the sensors is more or less than the average sympathetic activity through the day. The duration of the priming session may be up to as long as the stimulation session duration, or about, at least about, or no more than about 10%, 20%, 30%, 40%, 50%, 60%, 70%, 80%, or 90% or the duration of the stimulation session. In some embodiments, the intraburst frequency of stimulation (201) could be varied to conserve power or improve the efficacy of stimulation. The intraburst frequency can be, for example, as disclosed elsewhere herein.

In some embodiments, disclosed herein are devices for burst peripheral stimulation of one, two, or more nerves according to some embodiments of the invention. The devices can include a housing and one, two or more effectors, power sources, and/or controls. In some embodiments, the device further includes one or more sensors. The effectors can include a pulse generator and electrodes for delivering electrical stimulation, and/or can be a mechanical stimulator for delivering mechanical stimulation, such as vibratory stimulation, for example. The stimulation can be, for example, burst/patterned electrical stimulation as disclosed elsewhere herein. The sensors can include, for example, accelerometers, gyroscopes, and electrodes to measure electrical activity including nerve activity and muscle activity.

In some embodiments, electrical peripheral nerve burst stimulation can be utilized to stimulate one, two, or more nerves associated with bladder function, and unexpectedly effectively create plasticity in bladder neural circuits. In some embodiments, the peripheral nerve could be one or more of the saphenous nerve and/or the tibial nerves, for example. Such systems and methods can be combined with, or modified for use with systems and methods in PCT App. No. PCT/US2017/014431 filed on Jan. 20, 2017, which is hereby incorporated by reference in its entirety.

In some embodiments, disclosed is a method of treating urinary symptoms in a patient with transcutaneous stimulation of a nerve, such as the saphenous nerve or the tibial nerve. The method can include positioning a first peripheral nerve effector on the patient's skin to stimulate the saphenous nerve of the patient, delivering a first burst (e.g., theta burst) electrical nerve stimulation signal transcutaneously to the saphenous nerve through the first peripheral nerve effector, and receiving an input relating to autonomic nervous system activity of the patient to create a plastic effect and modulate a neural network associated with the bladder. The input can be used to modify the stimulation waveform or other parameters, such as the location, timing, frequency, amplitude, and the like as disclosed elsewhere herein. In some embodiments, the method does not utilize any implantable components, and only involves transcutaneous stimulation.

In some embodiments, disclosed herein is a method involving dual transcutaneous electrical burst stimulation of a saphenous nerve and a tibial nerve. The method can include positioning a first peripheral nerve effector on the patient's skin to stimulate the saphenous nerve of the patient; positioning a second peripheral nerve effector on the patient's skin to stimulate the tibial nerve of the patient; delivering a first burst electrical nerve stimulation signal transcutaneously to the saphenous nerve through the first peripheral nerve effector; delivering a second burst electrical nerve stimulation signal transcutaneously to the tibial nerve through the second peripheral nerve effector; receiving an input relating to autonomic nervous system activity of the patient; and modifying at least one brain or spinal cord autonomic feedback loop relating to bladder function with plasticity based on the input to balance parasympathetic and sympathetic nervous system activity of the patient. In some embodiments, patterned, such as burst stimulation, can be applied to one, two, or more nerves. Not to be limited by theory, each discrete nerve can modulate a different aspect of a physiologic reflex loop (e.g., the tibial nerve can modulate the parasympathetic reflex loop, and the saphenous nerve can modulate the sympathetic reflex loop).

In some embodiments, the weave of the brace or sock could be designed to provide tight pressure at the knee, calf, ankle, or other desired region of the device, similar to the weave of commonly found anklet socks. Electrodes can also be made from, for example, conventional hydrogels. In some cases, a clasp or fastening element such as Velcro may be needed because with sticky electrodes, the device cannot be easily slid on the foot. In some embodiments, the, e.g., knee, calf, ankle brace or anklet embodiments can be extended to electrode positions that are on the top (dorsal) or bottom (ventral) surfaces of the foot. In some cases, a sock with electrodes on the sole of the foot can be used with connectivity through the sock to an electronics module located near the ankle.

Combination Therapy

In some embodiments, burst peripheral nerve stimulation can be paired/combined with central nervous system stimulation for unexpectedly synergistic effects. For example, burst peripheral nerve stimulation can be combined with a noninvasive brain stimulation device or an invasive brain stimulation device, and can also include a feedback device, e.g., sensors, and a controller to synchronize stimulation between the peripheral nerve stimulation device and the central nervous system stimulation device.

Figure 19A:
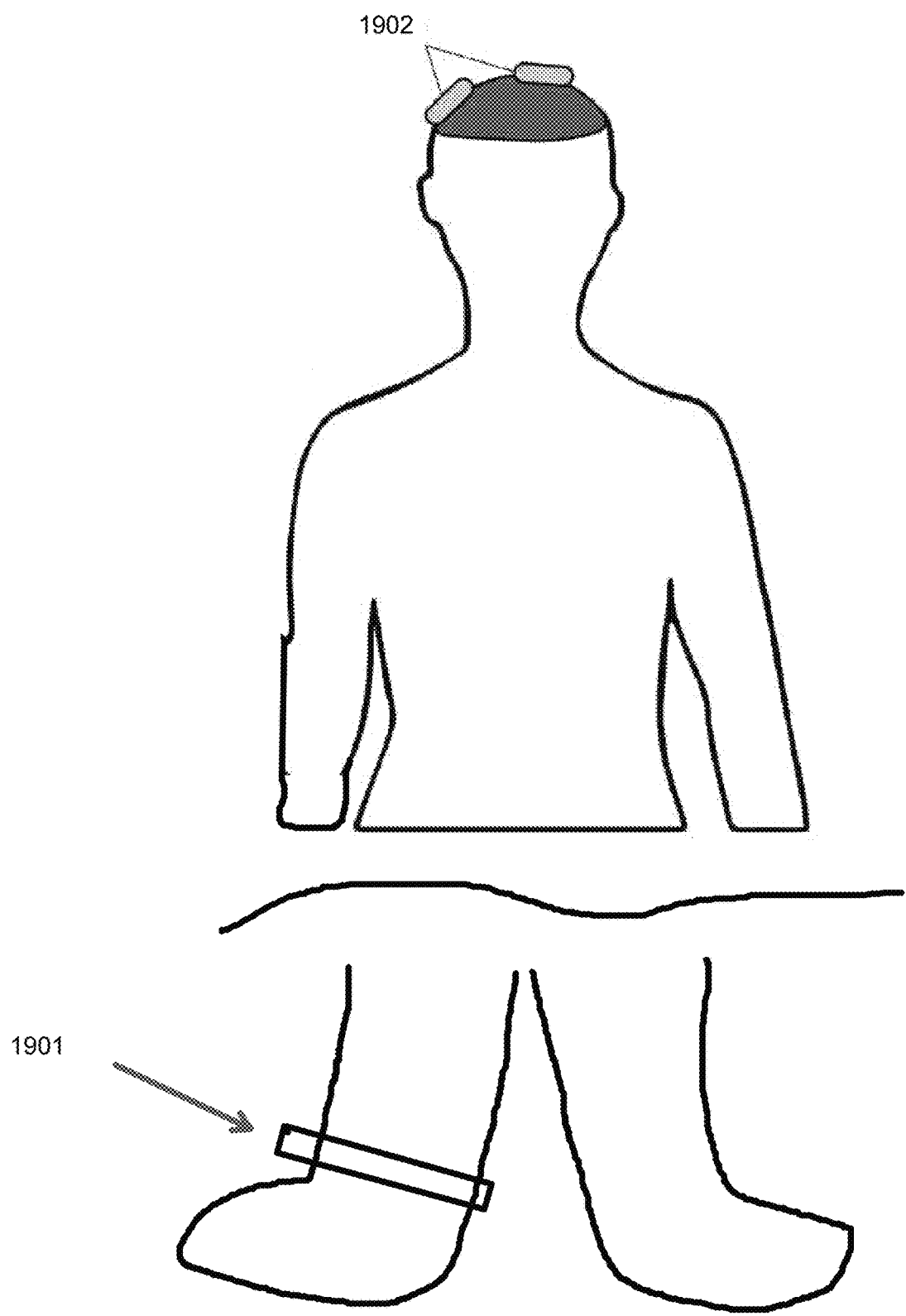
FIG. 19A illustrates an embodiment of a system that applies noninvasive transcranial stimulation in combination with theta burst stimulation of the peripheral nerves. In this embodiment, the transcranial stimulator is in wireless communication with the peripheral nerve stimulator. The peripheral nerve stimulator can be on the lower extremity as shown, or another location.

In another embodiment, the system may include a noninvasive transcranial stimulator using transcranial alternating cranial stimulation (TACS) in the form of a hat, cap, headband having electrodes 1902, for example in combination with a peripheral stimulator 1901 in another location, such as the lower extremity, as illustrated in FIG. 19A (or at the knee, calf, ankle, foot, or other desired location). Not to be limited by theory, transcranial alternating current stimulation can interfere with ongoing cortical rhythms and either synchronize or desynchronize oscillations in the brain. The range of frequencies that can be used is wide and can vary from low frequencies (about 1-2 Hz to up to about 5 kHz). By driving the oscillation of the brain with TACS at a set frequency such as the alpha frequency (8-12 Hz) or other frequencies as disclosed herein, the timing of the stimulation pulses of the peripheral nerve stimulator can be synchronized with oscillatory activity in the brain, and enhance the induction of plasticity. The peripheral nerve stimulator may also be in other locations, such as the fingers or wrists, with various form factors to stimulate various nerves for different conditions, as described in PCT Application No. PCT/US2016/045038, U.S. Pat. No. 9,452,287, and U.S. Pub. No. 2017/0157398, hereby incorporated by reference in their entireties.

In a further embodiment, a transcranial direct current stimulation (tDCS) or transcranial magnetic stimulation (TMS) can be applied to alter the excitability of the brain and modulate the efficacy of plasticity induction. Transcranial direct current stimulation uses weak electrical currents (roughly 1-2 mA) over the scalp and has been shown to affect underlying cortical network excitability. Additionally, electrical or magnetic stimulation of the spinal cord or spinal cord neural circuits can be applied to alter excitability of central neural circuits not in the brain, such as central pattern generators. Other CNS stimulation devices including optical, ultrasound, and the like can also be utilized.

In some embodiments, pulse width of an electrical stimulation waveform can be modified in order to stimulate the nerve fibers that affect that particular region or nucleus of the brain that is affected by or associated with the disease. Amplitude in the peripheral system may also be modified in order to select the right nerve type, according to the proper stimulation duration curves.

In some embodiments, the transcranial stimulator and the peripheral stimulator may communicate with wired or wireless communication in order to synchronize the timing of different stimulations in the central and peripheral systems. In some cases, the TACs may be activated prior to peripheral stimulation in order to synchronize the oscillation, for instance. Then the peripheral theta burst stimulation, in combination with the TACs, would altering the neural circuit dynamics associated with overactive bladder or another disorder.

In another embodiment, a theta burst stimulation pattern could be applied with an nerve stimulation implant to deeper nerves, such as the sacral or pudendal nerve, in order to improve symptoms associated with overactive bladder, stress urinary incontinence, lower urinary tract symptoms, or other bladder diseases.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. The methods disclosed herein include certain actions taken by a practitioner; however, they can also include any third-party instruction of those actions, either expressly or by implication. For example, actions such as "stimulating a peripheral nerve" includes "instructing the stimulating of a peripheral nerve." Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating urinary symptoms in a patient with dual transcutaneous stimulation of a first afferent lower extremity nerve and a second afferent lower extremity nerve, comprising:
    positioning a first peripheral nerve effector on the patient's skin to stimulate the first afferent lower extremity nerve of the patient;
    positioning a second peripheral nerve effector on the patient's skin to stimulate the second afferent lower extremity nerve of the patient;
    delivering a first electrical nerve stimulation signal transcutaneously to the first afferent lower extremity nerve through the first peripheral nerve effector;
    delivering a second electrical nerve stimulation signal transcutaneously to the second afferent lower extremity nerve through the second peripheral nerve effector;
    receiving an input relating to autonomic nervous system activity of the patient; and
    modifying at least one brain or spinal cord autonomic feedback loop relating to bladder function based on the input to balance parasympathetic and sympathetic nervous system activity of the patient,
    wherein the method does not utilize any implantable components, and only involves transcutaneous stimulation,
    wherein the first electrical stimulation signal and the second electrical stimulation signal comprise burst electrical stimulation signals, wherein the burst electrical stimulation signals induce neural plasticity.

2. The method of claim 1, wherein the burst stimulation signals comprises alpha, delta, or theta burst stimulation.

3. The method of claim 1, wherein the burst stimulation signals comprises theta burst stimulation.

4. The method of claim 1, wherein the burst stimulation signals comprise continuous, intermittent, or intermediate theta burst stimulation.

5. The method of claim 1, wherein the first electrical stimulation comprises a stimulation parameter modulated within a range from a first lower predetermined value to a second higher predetermined value, wherein the stimulation parameter is selected from the group consisting of pulse width, frequency, and amplitude.

6. The method of claim 1, wherein the first electrical stimulation comprises a randomized stimulation parameter selected from the group consisting of: pulse width, frequency, and amplitude.

7. The method of claim 1, wherein the first electrical stimulation signal is stimulatory to the first afferent lower extremity peripheral nerve.

8. The method of claim 1, wherein the first electrical stimulation signal is inhibitory to the first afferent lower extremity peripheral nerve.

9. The method of claim 1, wherein the first electrical stimulation signal is stimulatory to the first afferent lower extremity peripheral nerve, and the second electrical stimulatory signal is inhibitory to the second afferent lower extremity peripheral nerve.

10. The method of claim 1, further comprising delivering a priming electrical nerve stimulation signal prior to the first electrical stimulation signal, wherein the priming electrical nerve stimulation signal is a non-theta burst stimulation signal.

11. The method of claim 1, further comprising alternating the first electrical nerve stimulation signal to the first afferent lower extremity peripheral nerve and the second peripheral nerve signal to the second afferent lower extremity peripheral nerve.

12. The method of claim 1, wherein the first afferent lower extremity peripheral nerve is one of the saphenous nerve and a tibial nerve, and the method treats overactive bladder, nocturia, or stress incontinence of the user.

13. The method of claim 1, wherein the first afferent lower extremity peripheral nerve and the second afferent lower extremity peripheral nerve is selected from the group consisting of: a saphenous nerve and a tibial nerve, and the method reduces overactive bladder, nocturia, or stress incontinence of the user.

14. A wearable device for dual transcutaneous stimulation of a first afferent lower extremity nerve and a second afferent lower extremity nerve and for treating urinary symptoms in a patient, the device comprising:
    a controller;
    a first peripheral nerve effector, comprising at least one stimulation electrode configured to be positioned to transcutaneously modulate the saphenous nerve;
    a second peripheral nerve effector, comprising at least one stimulation electrode configured to be positioned to transcutaneously modulate the tibial nerve; and
    at least one biomedical sensor or data input source configured to provide feedback information;
    wherein the controller comprises a processor and a memory for receiving the feedback information from the sensor that, when executed by the processor, cause the device to:
    adjust one or more parameters of a first electrical stimulus and a second electrical stimulus based at least in part on the feedback information; and
    deliver the first electrical stimulus to the first afferent lower extremity nerve through the first peripheral nerve effector and deliver the second electrical stimulus to the second afferent lower extremity nerve through the second peripheral nerve effector to reduce urinary symptoms by modifying a brain or spinal cord autonomic feedback loop relating to bladder function and balancing sympathetic nerve and parasympathetic nerve activity,
    wherein the device is not configured for implantation within the patient,
    wherein the first electrical stimulus and the second electrical stimulus both comprise burst stimulation.

15. The wearable device of claim 14, wherein the burst stimulation comprises theta burst stimulation.

16. The wearable device of claim 14, wherein the first peripheral nerve effector is not physically connected to the second peripheral nerve effector.

17. A method of treating urinary symptoms in a patient with transcutaneous stimulation of an afferent lower extremity nerve, comprising:
    positioning a first peripheral nerve effector on the patient's skin to stimulate the afferent lower extremity nerve of the patient;
    delivering a first electrical nerve stimulation signal transcutaneously to the afferent lower extremity nerve through the first peripheral nerve effector;
    receiving an input relating to autonomic nervous system activity of the patient; and
    modifying at least one brain or spinal cord autonomic feedback loop relating to bladder function based on the input to balance parasympathetic and sympathetic nervous system activity of the patient, wherein the method does not utilize any implantable components, and only involves transcutaneous stimulation, wherein the first electrical stimulation signal comprises burst electrical stimulation signals, wherein the burst electrical stimulation signals induce neural plasticity.

18. The method of claim 17, wherein the burst stimulation signals comprises alpha, delta, or theta burst stimulation.

19. The method of claim 17, wherein the burst stimulation signals comprises theta burst stimulation.

* * * * *